United States Patent
Lukhtanov et al.

(10) Patent No.: US 10,890,529 B2
(45) Date of Patent: Jan. 12, 2021

(54) DUPLEX STABILIZING FLUORESCENCE QUENCHERS FOR NUCLEIC ACID PROBES

(71) Applicant: ELITechGroup, Inc., Logan, UT (US)

(72) Inventors: Eugeny A. Lukhtanov, Bothell, WA (US); Noah Scarr, Seattle, WA (US)

(73) Assignee: ELITECHGROUP, INC., Logan, UT (US)

( * ) Notice: Subject to any disclaimer, the term of this patent is extended or adjusted under 35 U.S.C. 154(b) by 0 days.

(21) Appl. No.: 16/788,588

(22) Filed: Feb. 12, 2020

(65) Prior Publication Data

US 2020/0173924 A1 Jun. 4, 2020

Related U.S. Application Data

(62) Division of application No. 16/057,016, filed on Aug. 7, 2018.

(60) Provisional application No. 62/546,965, filed on Aug. 17, 2017.

(51) Int. Cl.
| | |
|---|---|
| C07D 403/10 | (2006.01) |
| C07D 487/04 | (2006.01) |
| C07H 21/04 | (2006.01) |
| C08L 77/02 | (2006.01) |
| C12Q 1/6832 | (2018.01) |
| G01N 21/64 | (2006.01) |

(52) U.S. Cl.
CPC ....... G01N 21/6428 (2013.01); C07D 403/10 (2013.01); C07D 487/04 (2013.01); C07H 21/04 (2013.01); C08L 77/02 (2013.01); C12Q 1/6832 (2013.01); *G01N 2021/6432* (2013.01); *G01N 2021/6439* (2013.01)

(58) Field of Classification Search
CPC ....... G01N 21/6428; G01N 2021/6432; G01N 2021/6439; C07D 403/10; C07D 487/04; C07H 21/04; C08L 77/02; C12Q 1/6832
See application file for complete search history.

(56) References Cited

U.S. PATENT DOCUMENTS 6,274,728 B1 * 8/2001 Hall-Goulle ........... B41M 5/385
106/493

FOREIGN PATENT DOCUMENTS

| DE | 3232390 A1 * | 3/1983 | ........... C09B 29/366 |
|---|---|---|---|
| JP | 08238845 | 9/1996 | |
| WO | 02/099141 | 12/2002 | |
| WO | 03/062445 | 7/2003 | |
| WO | WO-03062445 A2 * | 7/2003 | ............ C07F 9/2408 |

OTHER PUBLICATIONS

Notification of Transmittal of the International Search Report and the Written Opinion dated Nov. 12, 2018 from the International Search Authority—The European Patent Office—for International Application No. PCT/US2018/045548, 15 pages.
Lukhtanov, et al., "Novel DNA probes with low background and high hybridization-triggered fluorescence", Nucleic Acids Research, 2007, vol. 35, No. 5, 14 pages.
Notification of Transmittal of the International Preliminary Report on Patentability containing the Written Opinion from the International Search Authority—The European Patent Office—dated Feb. 27, 2020 from the International Bureau of WIPO for International Application No. PCT/US2018/045548, 7 pages.

* cited by examiner

*Primary Examiner* — Amanda L. Aguirre
(74) *Attorney, Agent, or Firm* — Jackson Walker LLP

(57) ABSTRACT

Diaryl-azo derivatives are efficient fluorescence quenchers as well as nucleic acid duplex-stabilizing agents and are useful in oligonucleotide conjugates and probes. The oligonucleotide-quencher conjugates may be used in detection methods for nucleic acid targets.

10 Claims, 30 Drawing Sheets

Specification includes a Sequence Listing.

Main peak (tR=15.28 min) structure

FIG. 4A

| Modification ID | ~~~C(O)-Ar³-N(R¹)~~~ₙ | ~~~C(O)-Ar¹-N=N-Ar²~~~ | λ_max (nm) |
|---|---|---|---|
| 473 | (structure) | (structure) | 454 |
| 475 | (structure) | (structure) | 486 |
| 476 | (structure) | (structure) | 599 |
| 477 | (structure) | (structure) | 549 |
| 479 | (structure) | (structure) | 526 |
| 481 | (structure) | (structure) | 556 |

| Modification ID |  |  | λ$_{max}$ (nm) |
|---|---|---|---|
| 483 |  |  | 475 |
| 484 |  |  | 452 |
| 485 |  |  | 453 |
| 486 |  |  | 600 |
| 487 |  |  | 475 |
| 488 | none |  | 468 |

| Modification ID | [—C(O)—Ar³—N(R¹)—]ₙ | —C(O)—Ar¹—N=N—Ar² | λmax (nm) |
|---|---|---|---|
| 489 | none |  | 449 |
| 490 |  |  | 482 |
| 77 | None |  | 554 |
| Dabcyl | None |  | 470 |
| 79 |  |  | 550 |

FIG. 4D

| Modification ID | ~~C(=O)-Ar³-N(R¹)~~ₙ | ~~C(=O)-Ar¹-N=N-Ar²~~ | λ_max (nm) |
|---|---|---|---|
| 44 | None | (benzothiazole-azo-julolidine structure) | 600 |

Main peak (tR=14.33 min) structure

Main peak (tR=14.46 min) structure

Main peak (tR= 14.77 min) structure

| Name | Sequence (5'-3') | SEQ ID NO: | 5' | 3' |
|------|------------------|------------|------|------|
| KPC | G*CAGGTTCCGGTTTTG | 1 | 6-FAM | DSQ |
| KPC-C | TCAAAACCGGAACCTGCT | 3 | None | None |
| IC | G*ACCACGTACCGCATTG | 2 | AP525 | DSQ |
| IC-C | TCAATGCGGTACGTGGTCT | 4 | None | None |

SEQUENCE LISTING

<160> NUMBER OF SEQ ID NOS: 25

<210> SEQ ID NO 1
<211> LENGTH: 16
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (1)..(1)

```
<223> OTHER INFORMATION: n is Super G, 4-hydroxy-6-amino
      pyrazolopyrimidine
<220> FEATURE:
<221> NAME/KEY: misc_feature
<222> LOCATION: (1)..(1)
<223> OTHER INFORMATION: n is a, c, g, or t

<400> SEQUENCE: 1
ncaggttccg gttttg                                                       16

<210> SEQ ID NO 2
<211> LENGTH: 17
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (1)..(1)
<223> OTHER INFORMATION: n is Super G, 4-hydroxy-6-amino
      pyrazolopyrimidine
<220> FEATURE:
<221> NAME/KEY: misc_feature
<222> LOCATION: (1)..(1)
<223> OTHER INFORMATION: n is a, c, g, or t

<400> SEQUENCE: 2
naccacgtac cgcattg                                                      17

<210> SEQ ID NO 3
<211> LENGTH: 18
<212> TYPE: DNA
<213> ORGANISM: Artificial Sequence
<220> FEATURE:
<223> OTHER INFORMATION: probe complement

<400> SEQUENCE: 3
tcaaaaccgg aacctgct                                                     18

<210> SEQ ID NO 4
<211> LENGTH: 19
<212> TYPE: DNA
<213> ORGANISM: Artificial Sequence
<220> FEATURE:
<223> OTHER INFORMATION: probe complement

<400> SEQUENCE: 4
tcaatgcggt acgtggtct                                                    19

<210> SEQ ID NO 5
<211> LENGTH: 10
<212> TYPE: DNA
<213> ORGANISM: Artificial Sequence
<220> FEATURE:
<223> OTHER INFORMATION: complement

<400> SEQUENCE: 5
aaaaaaaacc                                                              10

<210> SEQ ID NO 6
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 6
```
acacaagcta ca                                                          12

<210> SEQ ID NO 7
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 7
ttatatgcca cg                                                          12

<210> SEQ ID NO 8
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 8
tacactggac at                                                          12

<210> SEQ ID NO 9
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 9
cagagcttac at                                                          12

<210> SEQ ID NO 10
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 10
gctctgttaa gt                                                          12

<210> SEQ ID NO 11
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 11
gaaaacaccg tc                                                          12

<210> SEQ ID NO 12
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 12
tcctgagtca ac                                                          12

```
<210> SEQ ID NO 13
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 13
cgctaaatcc tg                                                              12

<210> SEQ ID NO 14
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 14
tgttctaccg ag                                                              12

<210> SEQ ID NO 15
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 15
cgaaataccc tg                                                              12

<210> SEQ ID NO 16
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 16
cagagcttac at                                                              12

<210> SEQ ID NO 17
<211> LENGTH: 12
<212> TYPE: DNA
<213> ORGANISM: Artificial Sequence
<220> FEATURE:
<223> OTHER INFORMATION: experimental sequence for testing duplex
      stability

<400> SEQUENCE: 17
tcctgagtca ac                                                              12

<210> SEQ ID NO 18
<211> LENGTH: 29
<212> TYPE: DNA
<213> ORGANISM: Artificial Sequence
<220> FEATURE:
<223> OTHER INFORMATION: KPC primer

<400> SEQUENCE: 18
aataaatcat aagcagactg ggcagtcgg                                            29
```

-continued

```
<210> SEQ ID NO 19
<211> LENGTH: 29
<212> TYPE: DNA
<213> ORGANISM: Artificial Sequence
<220> FEATURE:
<223> OTHER INFORMATION: KPC primer

<400> SEQUENCE: 19
aataaatcat gtcatttgcc gtgccatac                                    29

<210> SEQ ID NO 20
<211> LENGTH: 26
<212> TYPE: DNA
<213> ORGANISM: Artificial Sequence
<220> FEATURE:
<223> OTHER INFORMATION: IC2 primer

<400> SEQUENCE: 20 ctcattttttt ctaccggaga tcttgt                                      26

<210> SEQ ID NO 21
<211> LENGTH: 23
<212> TYPE: DNA
<213> ORGANISM: Artificial Sequence
<220> FEATURE:
<223> OTHER INFORMATION: IC2 primer

<400> SEQUENCE: 21
ctgcacggac cagttacttt acg                                          23

<210> SEQ ID NO 22
<211> LENGTH: 16
<212> TYPE: DNA
<213> ORGANISM: Artificial Sequence
<220> FEATURE:
<223> OTHER INFORMATION: KPC probe
<220> FEATURE:
<221> NAME/KEY: modified_base
<222> LOCATION: (1)..(1)
<223> OTHER INFORMATION: n is Super G, 4-hydroxy-6-amino
      pyrazolopyrimidine
<220> FEATURE:
<221> NAME/KEY: misc_feature
<222> LOCATION: (1)..(1)
<223> OTHER INFORMATION: n is a, c, g, or t

<400> SEQUENCE: 22
ncaggttccg gttttg                                                  16

<210> SEQ ID NO 23
<211> LENGTH: 17
<212> TYPE: DNA
<213> ORGANISM: Artificial Sequence
<220> FEATURE:
<223> OTHER INFORMATION: IC2 probe
<220> FEATURE:
<221> NAME/KEY: modified_base
<222> LOCATION: (1)..(1)
<223> OTHER INFORMATION: n is Super G, 4-hydroxy-6-amino
      pyrazolopyrimidine
<220> FEATURE:
<221> NAME/KEY: misc_feature
<222> LOCATION: (1)..(1)
<223> OTHER INFORMATION: n is a, c, g, or t

<400> SEQUENCE: 23
naccacgtac cgcattg                                                 17

<210> SEQ ID NO 24
```

```
<211> LENGTH: 12
<212> TYPE: DNA
<213> ORGANISM: Artificial Sequence
<220> FEATURE:
<223> OTHER INFORMATION: experimental sequence for testing
      hybridization-triggered fluorescence

<400> SEQUENCE: 24
taaaaggtgt ac                                                          12

<210> SEQ ID NO 25
<211> LENGTH: 16
<212> TYPE: DNA
<213> ORGANISM: Artificial Sequence
<220> FEATURE:
<223> OTHER INFORMATION: experimental sequence for testing
      hybridization-triggered fluorescence

<400> SEQUENCE: 25
ttgtacacct tttatt                                                      16
```

DUPLEX STABILIZING FLUORESCENCE QUENCHERS FOR NUCLEIC ACID PROBES

This application is a divisional of and claims priority to U.S. patent application Ser. No. 16/057,016, filed Aug. 7, 2018, entitled "Duplex Stabilizing Fluorescence Quenchers for Nucleic Acid Probes," which claims priority to U.S. Provisional Patent Application No. 62/546,965, filed Aug. 17, 2017, entitled "Duplex Stabilizing Fluorescence Quenchers for Nucleic Acid Probes," the entire contents of which are hereby incorporated by reference.

BACKGROUND

This disclosure pertains to oligonucleotide-quencher conjugates with improved fluorescence characteristics, and to reagents suitable for incorporating novel quencher moieties into oligonucleotides. The disclosure also pertains to the use of oligonucleotide-quencher conjugates in detection methods for nucleic acid targets.

Minor groove binding (MGB) and fluorescence quenching are two key features of fluorescence-based DNA probe technologies. The first feature provides improved duplex stabilization and hybridization specificity, whereas the second one is required for reduction of background fluorescence of unhybridized probes. Historically, two independent functional groups have been used to fulfill these functions. The MGB and quenchers have been introduced into DNA probes using two reagents such as MGB-modified DNA synthesis solid supports and Quencher phosphoramidites. In another approach a MGB-Quencher solid support is utilized wherein MGB and quencher are linked together via a flexible spacer with each group serving its unique function. The existing MGB-Quencher structures and respective DNA synthesis reagents as disclosed in U.S. Pat. No. 6,492,346 are complicated and costly to manufacture.

SUMMARY

The present disclosure relates to certain diaryl-azo derivatives wherein said derivatives are efficient fluorescence quenchers as well as nucleic acid duplex-stabilizing agents. The present disclosure also relates to oligonucleotide conjugates bearing said diaryl-azo derivatives.

It is considered desirable to combine Minor groove binding (MGB) and fluorescence quenching in a simple unified structure. One approach to this problem is to convert part of the MGB moiety into a fluorescence quencher as Illustrated in FIG. 1. It is, however, not clear that such functional unification can be achieved within one structure without affecting the minor groove binding or fluorescence quenching properties. Surprisingly, certain preferred embodiments described herein can successfully accomplish this goal.

The disclosed diaryl-azo derivatives are especially useful for modification of certain types of known MGB agents (such as oliogomers of 3,6,7,8-tetrahydro-benzo[1,2-b: 4,3-b']dipyrrole-2-carboxylic acid (CDPI)) wherein a portion of the MGB structure is replaced with a disclosed diaryl-azo derivative. The two portions of such hybrid molecules are connected via a rigid amide bond with no ability for internal folding and limited rotation and, therefore, act as a single entity. As demonstrated herein, certain types of such hybrid molecules are as efficient or more efficient duplex stabilizing agent than their parent MGB moieties. The resultant hybrids are also efficient fluorescence quenchers for variety of typical fluorophores. This ability to merge duplex stabilization and fluorescence quenching within one structure is the key point of the disclosure.

The availability of the disclosed derivatives eliminates the need for two separate reagents and simplifies preparation of oligonucleotide conjugates that require both enhanced hybridization and efficient fluorescence quenching. Such conjugates are of special interest in fluorescence-based diagnostic applications.

BRIEF DESCRIPTION OF THE DRAWINGS

Figure 4D:
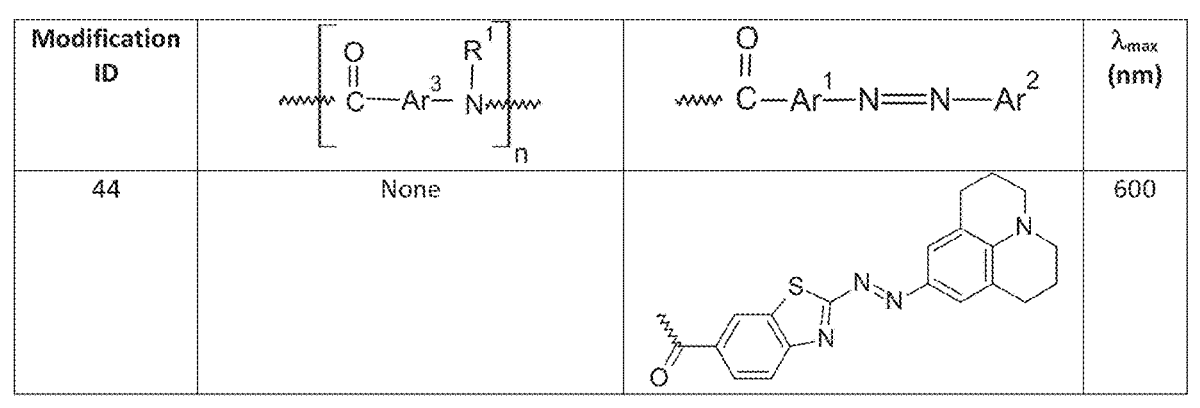

FIG. 4A shows structures and absorption maxima of the T8 oligonucleotide conjugates synthesized according to reaction Scheme 1.

FIG. 4D shows structures and absorption maxima of the T8 oligonucleotide conjugates synthesized according to reaction Scheme 1.

DETAILED DESCRIPTION

Definitions

Figure 1:
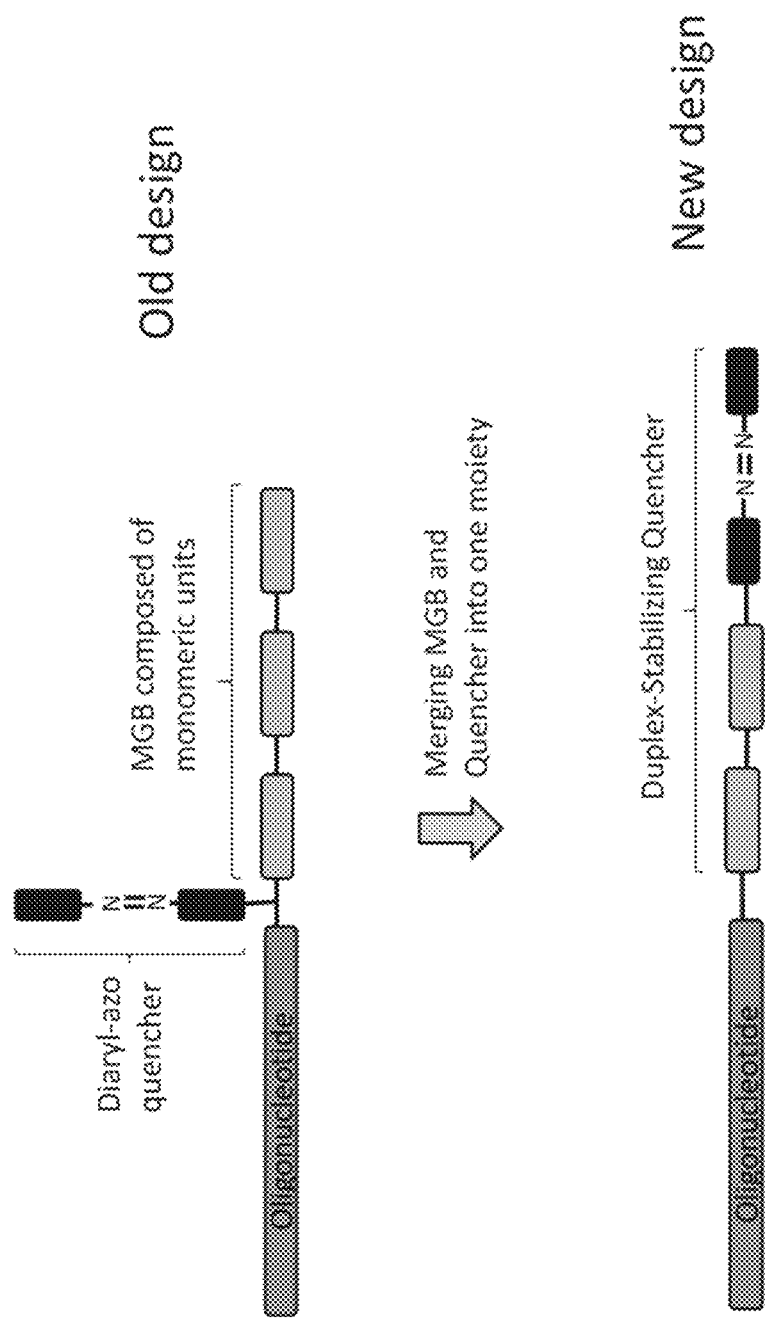
FIG. 1 shows a schematic of the concept of merging a minor groove binder and fluorescence quencher into a single Duplex-Stabilizing Quencher (DSQ) moiety.

The term "diaryl-azo" compounds or derivatives refers to diazene (HN=NH) derivatives wherein both hydrogen atoms substituted with two aryl groups. For the purpose of this specification the term aryl encompasses the definitions of both terms "aryl" and "heteroaryl".

The term "aromatic amino acid" refers to an aromatic compound comprising an aromatic carboxylic and an aromatic amino group.

The abbreviations MGB, Fl, Q CPG and ODN refer to "minor groove binder", "fluorescent label" or "fluorophore", "quencher", "controlled pore glass" (as an example of a solid support) and "oligonucleotide" moieties or molecules, respectively, and in a manner which is apparent from context.

The term "minor groove binder" refers to a moiety that is capable of forming a complex (typically non-covalent) with the minor groove of DNA. The minor groove binders of the invention are oligonucleotide conjugates (or "probes") as described in U.S. Pat. Nos. 5,801,155 and 6,312,894, both hereby incorporated by reference. These conjugates form hyper-stabilized duplexes with complementary DNA. In particular, sequence specificity of short minor groove binder probes is excellent for high temperature applications such as PCR. The probes/conjugates of the present disclosure can also have a covalently attached minor groove binder. A variety of suitable minor groove binders have been described in the literature (U.S. Pat. No. 5,801,155; Wemmer, D. E., and Dervan P. B. (1997; Walker et al. (1997), *Biopolymers*, 44:323-334 (1997); Zimmer, C & Wahnert, U., (1986) and Reddy, et al. (1999), *Pharmacol. Therap.*, 84:1-111 (1999)).

Suitable methods for attaching minor groove binders (as well as reporter groups such as fluorophores and quenchers) through linkers to oligonucleotides have also been described (U.S. Pat. Nos. RE 38, 416; 5,512,667; 5,419,966; 5,696, 251; 5,585,481; 5,942,610 and 5,736,626).

The term "fluorescent label or fluorophore" refers to an organic moiety that is capable of absorbing and re-emitting light. Typically, fluorophores absorb light of certain wavelength range (excitation spectrum) and re-emitting it at a longer wavelength range (emission spectrum) with respective excitation and emission maxima. The fluorophores of the invention have excitation and emission maxima between 400 and 900 nm. Examples of these dye classes can be found in Haugland, et al., HANDBOOK OF FLUORESCENT PROBES AND RESEARCH CHEMICALS, SIXTH ED., Molecular Probes, Eugene, Oreg. 1996; Krasovitskii and Bolotin, ORGANIC LUMINESCENT MATERIALS, VCH Publishers, N.Y., 1988; Zolliger, COLOR CHEMISTRY, 2nd Edition, VCH Publishers, N.Y., 1991. Still other dyes are provided via online sites such as zeiss.com. Phosphonate dyes are disclosed in co-owned U.S. Pat. Nos. 7,671,218, 7,767,834 and 8,163,910B2

The term "quencher" refers to an organic moiety that is capable of reducing the efficiency of light re-mission by a fluorophore. Quenchers have been disclosed in U.S. Pat. No. 3,996,345, in co-owned U.S. Pat. Nos. 6,727,356 and 6,790, 945, and in Matayoshi et al., 1990.

The term "oligonucleotide" refers to a fragment of natural or artificial nucleic acid or combination of thereof. Examples of artificial nucleic acids include analogs with modified sugar-phosphate backbone such as 2-OMe nucleic acid, peptide nucleic acid (PNA), locked nucleic acid (LNA), threose nucleic acid (TNA), glycol nucleic acid (GNA) (U.S. Pat. Nos. 5,539,082, 8,293,684 and 9,464,316). Artificial nucleic acid (U.S. Pat. No. 9,169,256) may also comprise modified nucleobases.

The term "modified nucleobases or modified bases" refers to those bases that differ from the naturally-occurring bases (adenine, cytosine, guanine, thymine, and uracil) by addition or deletion of one or more functional groups, differences in the heterocyclic ring structure (i.e., substitution of carbon for a heteroatom, or vice versa), and/or attachment of one or more linker arm structures to the base. Modified bases include naturally-occurring and synthetic modifications and analogues of the major bases such as, for example, hypoxanthine, 2-aminoadenine, 2-thiouracil, 2-thiothymine, inosine, 5-$N^4$-ethenocytosine, 4-aminopyrrazolo[3,4-d]pyrimidine and 6-amino-4-hydroxy-[3,4-d]pyrimidine. Any modified nucleotide or nucleotide analogue compatible with hybridization of probe with a nucleic acid conjugate to a target sequence is useful, even if the modified nucleotide or nucleotide analogue itself does not participate in base-pairing, or has altered base-pairing properties compared to naturally-occurring nucleotides. Examples of modified bases are disclosed in U.S. Pat. Nos. 7,045,610; 5,824,796; 6,127,121; 5,912,340; and PCT Publications WO 01/38584 and WO 01/64958, each of which is hereby incorporated herein by reference in its entirety. Preferred modified bases include 5-hydroxybutynyl uridine for uridine; 4-(4,6-Diamino-$^1$H-pyrazolo[3,4-d]pyrimidin-3-yl)-but-3-yn-1-ol, 4-amino-$^1$H-pyrazolo[3,4-d]pyrimidine, and 4-amino-$^1$H-pyrazolo[3,4-d]pyrimidine for adenine; 5-(4-Hydroxy-but-1-ynyl)-1H-pyrimidine-2,4-dione for thymine; and 6-amino-$^1$H-pyrazolo[3,4-d]pyrimidin-4(5H)-one for guanine. Particularly preferred modified bases are "Super A®: 4-(4, 6-Diamino-1H-pyrazolo[3,4-d]pyrimidin-3-yl)-but-3-yn-1-ol," "Super G®: 4-hydroxy-6-amino pyrazolopyrimidine"

(elitechgroup.com) and "Super T®: 5-(4-hydroxy-but-1-ynyl)-1H-pyrimidine-2,4-dione". "Super-D™: 3-Alkynyl pyrazolopyrimidine" analogues as universal bases are disclosed in U.S. Patent Application Publication No. 2012/0244535, incorporated by reference.

The term "linker" and "linking group" refers to a moiety that is used to assemble various portions of the molecule or to covalently attach the molecule (or portions thereof) to a solid support. Typically, a linker or linking group has functional groups that are used to interact with and form covalent bonds with functional groups in the ligands or components (e.g., fluorophores, oligonucleotides, minor groove binders, or quenchers) of the oligonucleotide probes described and used herein. Additionally, a linker can include linear or acyclic portions, cyclic portions, aromatic rings or combinations thereof (U.S. Pat. Nos. 5,419,966; 5,696,251; 5,585,481; 5,942,610 and 5,736,626).

The terms "functional" and "reactive" groups in this invention are used interchangeably and refer to chemical groups and moieties that are suitable for the formation of a chemical bond. They are exemplified but not limited to amines, oxyamines, hydrazines, hydrazides, semi-carbazides, semi-thiocarbazides, hydroxyl-substituted compounds, sulfur compounds (such as thiols, dithiols, thiocarbonyl compounds, phosphorothiates), carboxylates, phosphates, phosphonates, aromatic nitrogens (such as in pyridine), amide nitrogens, azides, electron-rich aromatics, etc.), acids (in the presence of activating agents), esters, imidoesters, anhydrides, acid chlorides, acyl azides, lactones, azlactones, isocyanates, isothiocyanates, o-acylisoureas, acid amides (such as acyl imidazolides or phosphoramidites), carbonyl compounds, halogenated hydrocarbons, halogenated aromatics (such as triazine chloride, electron-deficient fluoroaromatics), unsaturated hydrocarbons, aromatic diazonium salts, epoxides, aziridines. Other types of functional or reactive groups include photo-reactive (azides, benzophenones, diazirines, etc.), metal chelating groups (aminodiacetic acid), substrates for metal-catalyzed coupling, ligands for molecular recognition (such as biotin), antigens and haptens. Functional and reactive groups of this invention may also be used in conjunction with bi-functional or poly-functional cross-linking reagents (such as bis-amines, bis-aldehydes, maleimido-NHS esters, etc). Other examples of reactive groups and cross-linking reaction can be found in literature (Hermanson, Bioconjugate Techniques, Elsevier, 1996).

"Leaving group" means a molecular fragment that departs with a pair of electrons in heterolytic bond cleavage. Common leaving groups are halides such as Cl—, Br—, and I—, sulfonate esters such as tosylate (TsO—), phenolates such as 4-nitrophenylate, and water (Smith, 2007).

"Protecting group" or "protected form thereof" or "protected functional group" or "PFP" or "blocking group" refers to a grouping of atoms that, when attached to a reactive group in a molecule, masks, reduces or prevents that reactivity. Examples of protecting groups can be found in T. W. Greene and P. G. Wuts, 2007 and Harrison and Harrison et al 1971 to 1996. Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilylethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

The term "solid support" or "synthesis solid support" refers to any support that is compatible with oligonucleotide synthesis including, for example, glass, controlled pore glass, polymeric materials, polystyrene, beads, coated glass and the like.

The term "exocyclic amino group" means an amino group situated outside of a chemical ring, such as in aniline.

The term "alkyl" refers to a linear, branched, or cyclic saturated monovalent hydrocarbon substituent or a combination of cyclic and linear or branched saturated monovalent substituents having the number of carbon atoms indexed in the prefix. For example, $(C_1-C_8)$alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, aralkyloxy), when a prefix is not included to indicate the number of chain carbon atoms in an alkyl portions, the substituent thereof will have eight or fewer main chain carbon atoms.

The term "alkylene" refers to a linear saturated divalent hydrocarbon substituent or a branched saturated divalent hydrocarbon substituent having the number of carbon atoms indicated in the prefix. For example, $(C_1-C_6)$alkylene is meant to include methylene, ethylene, propylene, 2-methylpropylene, pentylene, and the like.

The term "aromatic" or "aryl" means a monovalent or bivalent (e.g., arylene) monocyclic, bicyclic aromatic or tricyclic hydrocarbon substituent of 5 to 14 ring atoms which is unsubstituted or substituted. If substituted the substituents are selected from those groups provided below. The term "heteromatic" or "heteroaryl" refers to aryl wherein one or more heteroatoms or heteroatom functional groups have replaced a ring carbon, while retaining aromatic properties, e.g., pyridyl, quinolinyl, quinazolinyl, thienyl, and the like. More specifically the terms aryl and heteroaryl include, but are not limited to, phenyl, 1-naphthyl, 2-naphthyl, thienyl, thiazolyl and benzothiazolyl, and the substituted forms thereof.

Substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O) NR'R", —NR"C(O)R', —NR"C(O)2R', —NR'—C(O), NR"R", —NH—C(NH2)=NH, —NR'C(NH2)=NH, —NH—C(NH2)=NR', —S(O)R', —S(O)$_2$R', —S(O)$_2$NR'R", —N$_3$, —CH(Ph)$_2$, perfluoro$(C_1-C_4)$alkoxy, and perfluoro$(C_1-C_4)$alkyl, in a number ranging from zero to the total number of open valences on the aromatic ring system; and where R', R" and R''' are independently selected from hydrogen, $(C_1-C_8)$alkyl and heteroalkyl, unsubstituted aryl and heteroaryl, (unsubstituted aryl)-$(C_1-C_4)$alkyl, and (unsubstituted aryl)oxy-$(C_1-C_4)$alkyl. Preferred substituents are —OH, Halogen, OR', —OC(O)R', —NR'R", —SR', —R', —CN and —NO$_2$— where R' and R" are independently —H— or —$(C_1-C_4)$.

The prefix "halo" and the term "halogen," when used to describe a substituent, refer to —F, —Cl, —Br and —I. Certain compounds or oligonucleotides of the present disclosure may exist in a salt form.

Such salts include base addition salts such as sodium, potassium, calcium, ammonium, organic amino, or magnesium salt, or a similar salt. When the compounds or modified oligonucleotides of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (Berge, S. M., et al. 1977). Certain specific compounds described herein contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the racemates, diastereomers, geometric isomers and individual isomers are all intended to be encompassed within the scope of the present disclosure. The methods for the determination of stereochemistry and the separation of isomers are well-known in the art (March J. 1992).

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not (e.g, $^2$H), are intended to be encompassed within the scope of the present disclosure.

"Optional" or "optionally" in the above definitions means that the subsequently described event or circumstance may but need not occur, and that the description includes instances where the event or circumstance occurs and instances in which it does not. For example, "aryl optionally mono- or di-substituted with an alkyl group" means that the alkyl group may, but need not, be present, and the description includes situations where the aryl group is mono- or bis-substituted with an alkyl group and situations where the aryl group is not substituted with the alkyl group.

In certain instances, amplification is carried out using a polymerase. The polymerase can, but need not, have 5' nuclease activity. In certain other instances, primer extension is carried out using a reverse transcriptase and amplification is carried out using a polymerase (U.S. Pat. Nos. 6,312,894, and 7,381,818). In other instances, the amplification is isothermal (U.S. Patent Application No. 2014 0255928).

In one embodiment, the amplified targets are detected, with dual FRET DSQ-conjugute probes, as taught in U.S. Pat. Nos. 6,312,894, 7,381,818 and U.S. Patent Application No. 2014 0255928, all incorporated by reference)

The term "digital PCR" refers to an approach to nucleic acid detection and quantification, which is a method of absolute quantification since it directly counts the number of target molecules rather than relying on reference standards or endogenous controls (Sedlak and Jerome 2013).

The term "arrays" refers to hybridization of the probes of the invention to an immobilized oligonucleotide (U.S. Pat. No. 6,045,996). In some arrays, the probes described herein are immobilized to a solid support (U.S. Pat. No. 6,821,727).

The practice of the present disclosure will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Maniatis, Fritsch & Sambrook 1982; Sambrook, Fritsch & Maniatis, (1989); Ausubel, et al., 1987, 1988, 1989, 1990, 1991, 1992, 1993, 1994, 1995, 1996; Gait (ed.), 1984; Eckstein (ed.), 1991.

DESCRIPTION

Certain diaryl-azo derivatives are described herein, wherein said derivatives are efficient fluorescence quenchers as well as nucleic acid duplex-stabilizing agents. These derivates may also be referred to as Duplex-Stabilizing Quenching (DSQ) compounds, derivatives or agents.

In preferred embodiments, DSQ derivatives comprise a diaryl-azo carboxylic acid of general Formula I:

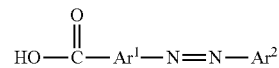

Formula I wherein $Ar^1$ and $Ar^2$ are aromatic moieties, optionally comprising a functional group or a linker with a functional group or protected functional group.

In certain preferred embodiments, the diaryl-azo carboxylic acids of Formula I are coupled via a carboxamide bond to a minor groove binding aromatic amino acid (or peptide) of Formula II to yield DSQ compounds of Formula III:

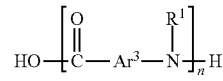

Formula II

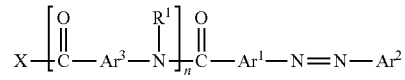

Formula III wherein $Ar^1$ and $Ar^2$ are aromatic or hetero-aromatic moieties, which are optionally substituted with a functional group or a linker with a functional group or protected functional group or a linker connecting to a synthesis solid support;
$Ar^3$ is an aromatic or hetero-aromatic moiety;
$R^1$ is H, alkyl or alkyl covalently connected to $Ar^3$;

X is hydroxyl, a leaving group, a linker with a functional group or protected functional group, or a linker connecting to a synthesis solid support; and n is from 0 to 5. If n is greater than 1 each Ar³ may be the same or different.

Table 1 below shows examples of HOOC—Ar¹ and Ar² groups in accordance with preferred embodiments disclosed herein, where the HOOC—Ar¹ and Ar² groups are substituted with preferred substituents. The wavy bond indicates the attachment point to the azo group in Formula III.

TABLE 1

HOOC—Ar¹

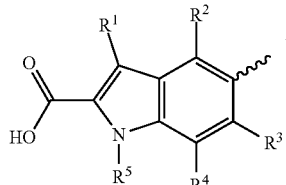

$R^1, R^2, R^3, R^4$ = —H, -Alkyl, -OAlkyl, -Aryl, -OAryl, —F, —Cl, —Br, —CF$_3$, —NO$_2$,
$R^5$ = H, Alkyl, —C(=O)OAlkyl, protecting group

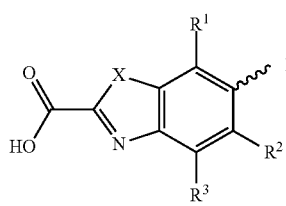

$R^1, R^2, R^3$ = —H, -Alkyl, -OAlkyl, -Aryl, -OAryl, —F, —Cl, —Br, —CF$_3$, —NO$_2$,
X=O, S

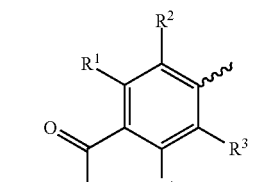

$R^1, R^2, R^3, R^4$ = —H, -Alkyl, -OAlkyl, -Aryl, -OAryl, —F, —Cl, —Br, —CF$_3$, —NO$_2$,

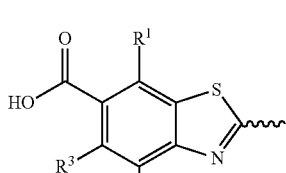

$R^1, R^2, R^3$ = —H, -Alkyl, -OAlkyl, -Aryl, -OAryl, —F, —Cl, —Br, —CF$_3$, —NO$_2$,

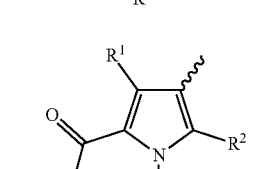

$R^1, R^2$ = —H, -Alkyl, -OAlkyl, -Aryl, -Heteroaryl, -OAryl, —F, —Cl, —Br, —CF$_3$, —NO$_2$,
$R^5$ = H, Alkyl

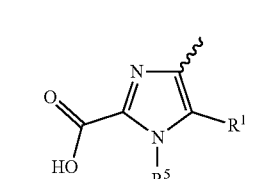

$R^1$ = —H, -Alkyl, -OAlkyl, -Aryl, -Heteroaryl, -OAryl, —F, —Cl, —Br, —CF$_3$, —NO$_2$,
$R^5$ = H, Alkyl

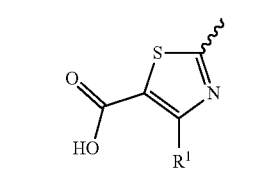

$R^1$ = —H, -Alkyl, -OAlkyl, -Aryl, -Heteroaryl, -OAryl, —F, —Cl, —Br, —CF$_3$, —NO$_2$, TABLE 1-continued HOOC—Ar¹

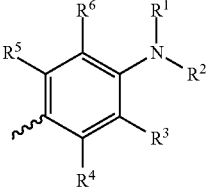

R¹, R² = —H, -Alkyl,-Aryl, -Heteroaryl, Alkyl-OH, Alkyl-COOH, Alkyl-Amine
R³, R⁴, R⁵, R⁶ = H, -Alkyl, -Aryl, Heteroaryl, -OAlkyl, -OAryl, —NHR¹, —NHC(=O)R¹,

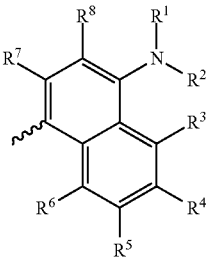

R¹, R² = —H, -Alkyl,-Aryl, -Heteroaryl, Alkyl-OH, Alkyl-COOH, Alkyl-Amine
R³, R⁴, R⁵, R⁶, R⁷, R⁸ = H, -Alkyl, -Aryl, Heteroaryl, -OAlkyl, -OAryl, —NHR¹, —NHC(=O)R¹

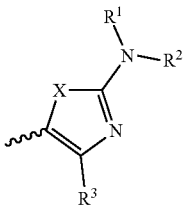

X = S, Se, O, NH, NCH₃
R¹, R² = —H, -Alkyl,-Aryl, -Heteroaryl, Alkyl-OH, Alkyl-COOH, Alkyl-Amine R³ = H, -Alkyl, -Aryl, Heteroaryl, -OAlkyl, -OAryl, —NHR¹, —NHC(=O)R¹

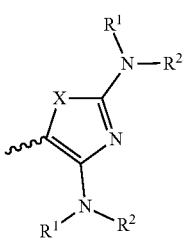

X = S, Se, O, NH, NCH₃
R¹, R² = —H, -Alkyl,-Aryl, -Heteroaryl, Alkyl-OH, Alkyl-COOH, Alkyl-Amine

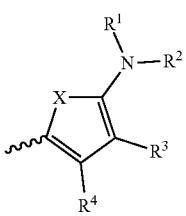

X = S, Se, O, NH, NCH₃
R¹, R² = —H, -Alkyl,-Aryl, -Heteroaryl, Alkyl-OH, Alkyl-COOH, Alkyl-Amine
R³, R⁴ = H, -Alkyl, -Aryl, Heteroaryl, -OAlkyl, -OAryl, —NHR¹, —NHC(=O)R¹

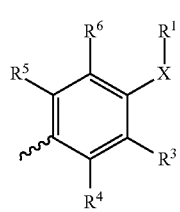

X = O, S, Se
R¹, R³, R⁴, R⁵, R⁶ = H, -Alkyl, -Aryl, Heteroaryl, -OAlkyl, -OAryl, —NHR¹, —NHC(=O)R¹, Alkyl-OH, Alkyl-COOH, Alkyl-Amine TABLE 1-continued

| HOOC—Ar¹ | |
|---|---|
| 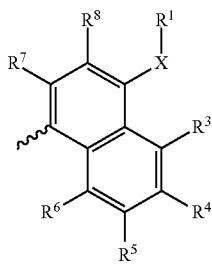 | X = O, S, Se<br>$R^1$, $R^3$, $R^4$, $R^5$, $R^6$, $R^7$, $R^8$ = H, -Alkyl, -Aryl, —NHC(=O)R1, Alkyl-OH, Alkyl-COOH, Alkyl-Amine Heteroaryl, -OAlkyl, -OAryl, —$NHR^1$, |
| 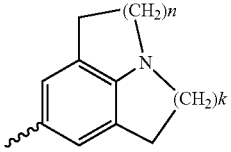 | n = 2-4, k = 2-4 |
| 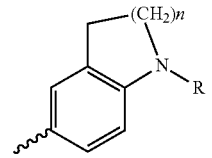 | n = 2-4, R = H, Alkyl, Alkyl-OH, Alkyl-COOH, Alkyl-Amine |

Table 2 below shows examples of minor groove binding aromatic amino acids (HOOC—Ar³—NH($R^1$)) of Formula II in accordance with preferred embodiments disclosed herein, where the minor groove binding aromatic amino acids are substituted with preferred substituents. The wavy bond indicates the attachment point to the azo group in Formula II.

TABLE 2

| HOOC—Ar³—NH($R^1$) | |
|---|---|
| 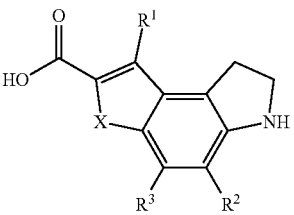 | X = NH, N(Alkyl), N(C=O)OAlkyl, N(Protecting group),O, S, Se<br>$R^1$, $R^2$, $R^3$ = H, -Alkyl, -Aryl, Heteroaryl, -OAlkyl, -OAryl, —$NHR^1$, —NHC(=O)$R^1$,—F, —Cl, —Br |
| 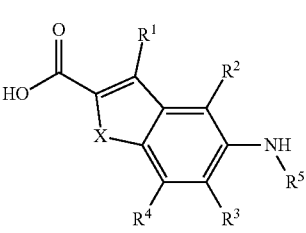 | X = NH, N(Alkyl), N(C=O)OAlkyl, N(Protecting group), O, S, Se<br>$R^1$, $R^2$, $R^3$, $R^4$ = H, -Alkyl, -Aryl, Heteroaryl, -OAlkyl, -OAryl, —$NHR^1$, —NHC(=O)$R^1$,—F, —Cl, —Br |
| 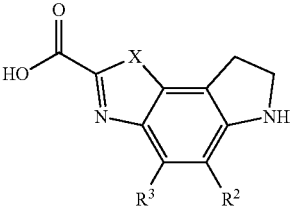 | X = NH, N(Alkyl), O, S, Se<br>$R^2$, $R^3$ = H, -Alkyl, -Aryl, Heteroaryl, -OAlkyl, -OAryl, —$NHR^1$. —NHC( O)$R^1$, —F, —Cl, —Br |

TABLE 2-continued

HOOC—Ar³—NH(R¹)

| Structure | Substituents |
|---|---|
| (benzazole-2-carboxylic acid with R¹, R², R³, R⁵, X) | X = NH, N(Alkyl), O, S, Se<br>R², R³ = H, -Alkyl, -Aryl, Heteroaryl, -OAlkyl, -OAryl, —NHR¹, —NHC(=O)R¹, —F, —Cl, —Br<br>R⁵ = —H, Alkyl |
| (benzothiophene/benzofuran-5-carboxylic acid with R¹, R², R³, R⁴, R⁶, R⁵, X) | X = NH, N(Alkyl), O, S, Se<br>R¹, R², R³, R⁴ = H, -Alkyl, -Aryl, Heteroaryl, -OAlkyl, -OAryl, —NHR¹, —NHC(=O)R¹, —F, —Cl, —Br<br>R⁵ = —H, Alkyl |
| (benzazole-5-carboxylic acid with R¹, R³, R⁴, R⁶, R⁵, X) | X = NH, N(Alkyl), O, S, Se<br>R¹, R³, R⁴ = H, -Alkyl, -Aryl, Heteroaryl, -OAlkyl, -OAryl, —NHR¹, —NHC(=O)R¹, —F, —Cl, —Br<br>R⁵ = —H, Alkyl |
| (pyrrole-2-carboxylic acid with R¹, R², R³, NHR⁴) | R¹, R⁴ = —H, Alkyl.<br>R², R³ = H, -Alkyl, -Aryl, Heteroaryl, -OAlkyl, -OAryl, —NHR¹, —NHC(=O)R¹, —F, —Cl, —Br |
| (3-hydroxypyrrole-2-carboxylic acid with R¹, R², NHR⁴) | R¹, R⁴ = —H, Alkyl<br>R² = H, -Alkyl, -Aryl, Heteroaryl, -OAlkyl, -OAryl, —NHR¹, —NHC(=O)R¹, —F, —Cl, —Br |
| (imidazole-2-carboxylic acid with R¹, R², NHR⁴) | R¹, R⁴ = —H, Alkyl<br>R² = H, -Alkyl, -Aryl, Heteroaryl, -OAlkyl, -OAryl, —NHR¹, —NHC(=O)R¹, —F, —Cl, —Br |
| (thiazole-4-carboxylic acid with R², NHR⁴) | R⁴ = —H, Alkyl<br>R² = H, -Alkyl, -Aryl, Heteroaryl, -OAlkyl, -OAryl, —NHR¹, —NHC(=O)R¹, —F, —Cl, —Br |

In preferred embodiments, the diaryl-azo caroboxylic acids are coupled to a minor groove binding aromatic amino acid that is 3,6,7,8-tetrahydro-benzo[1,2-b:4,3-b']dipyrrole-2-carboxylic acid (CDPl) yielding DSQ derivatives of Formula III (a):

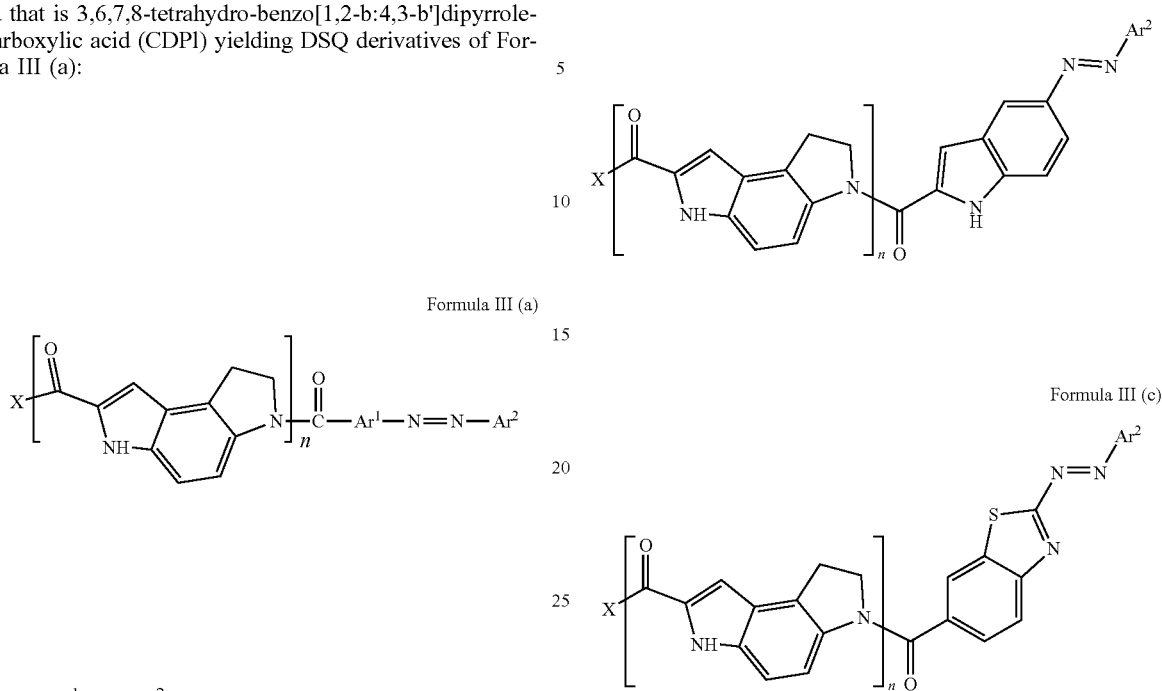

Formula III (a)

Formula III (b)

wherein $Ar^1$ and $Ar^2$ are aromatic or hetero-aromatic moieties, which are optionally substituted with a functional group or a linker with a functional group or protected functional group or a linker connecting to a synthesis solid support;
X is hydroxyl, a leaving group, a linker with a functional group or protected functional group, or a linker connecting to a synthesis solid support; and
n is from 0 to 5.

In further preferred embodiments of the diaryl-azo carboxylic acids, with regard to Formula III (a), the $Ar^1$ moiety is an indole or benzothiazole ring yielding DSQ derivatives of Formula III (b) and Formula III (c):

Formula III (c)

In additional preferred embodiments, in Formula III (b) and III (c), the Are moiety is an aromatic or hetero-aromatic ring with an exocyclic amino group, in which said exocyclic amino group is optionally substituted with one or two of an alkyl, a linker with a functional group or protected functional group, or a linker connecting to a synthesis solid support; n is between 0 and 3; X is —OH, a leaving group, a linker with a functional group or protected functional group, or a linker connecting to a synthesis solid support.

Additional preferred embodiments include Formula III derivatives represented by Formula III (d) and III (e):

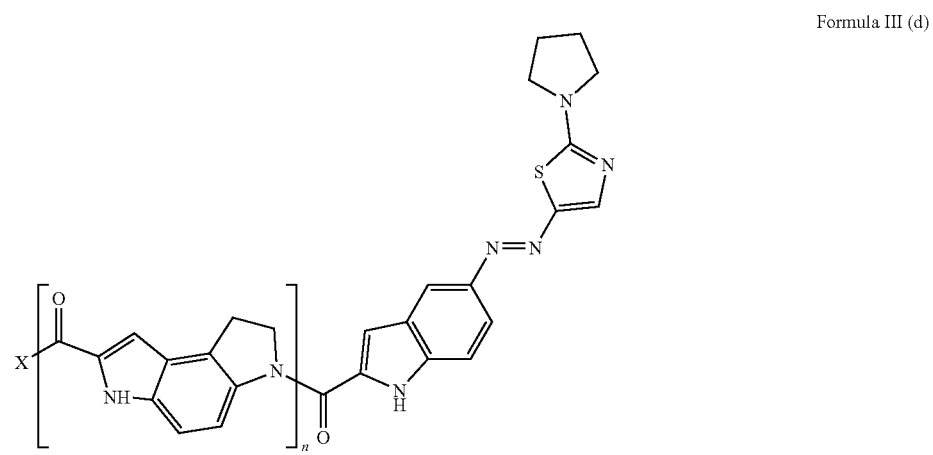

Formula III (d)

-continued

Formula III (e)

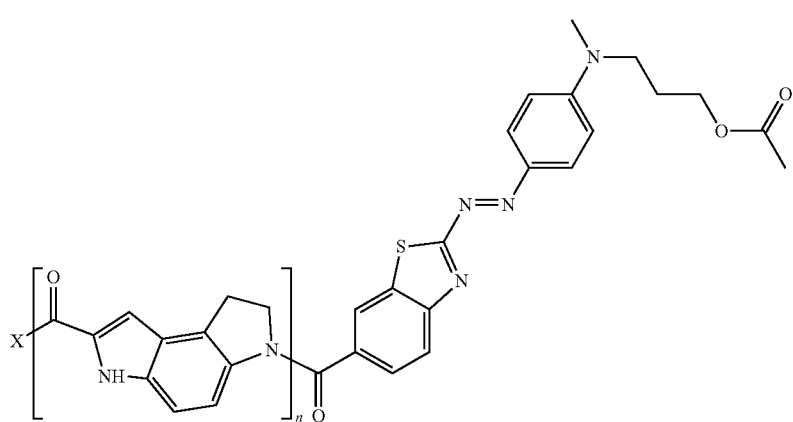

wherein X is hydroxyl, —OPFP, or a leaving group, and n is 0, 1 or 2.

Compounds of Formula III are particularly useful for the preparation of oligonucleotide conjugates of Formula IV (a) or IV (b):

Formula IV (a)

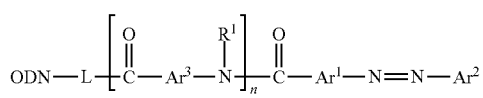

Formula IV (b)

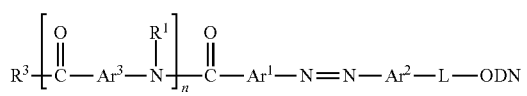

wherein ODN is an oligonucleotide; L is a linking group having from 0 to 100 main chain atoms selected from C, N, O, S, P and Si and can be acyclic, cyclic or aromatic or combinations thereof; $R^1$ is H, alkyl, or alkyl covalently connected to $Ar^3$; and $R^3$ is hydroxyl, a linking or blocking group; $Ar^1$ and $Ar^2$ are aromatic or hetero-aromatic moieties; and $Ar^3$ is an aromatic moiety. If n is greater than 1, each $Ar^3$ may be the same or different. In preferred embodiments, the oligonucleotide conjugate may further comprise a fluorophore connected to the oligonucleotide, and the fluorophore may be any suitable fluorophire including FAM, AP525, AP559, AP593 or AP662. The oligonucleotide may further comprise a minor groove binder connected to the oligonucleotide. The oligonucleotide conjugate may also include one or more modified nucleobases or modified bases. The linker L may be connected to the oligonucleotide at its 3'-end or its 5'-end, or it may be connected to the oligonucleotide at a position other than a 3'- or 5'-end.

In preferred embodiments, the oligonucleotide conjugates of Formula IV (a) are represented by Formula IV (c):

Formula IV (c)

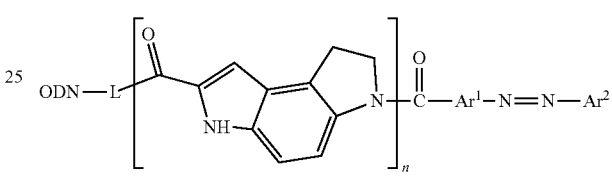

wherein n is 1, 2, or 3.

In additional preferred embodiments, the oligonucleotide conjugates of Formula IV (c) are represented by Formula IV (d) or IV (e):

Formula IV (d)

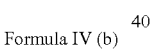

Formula IV (e)

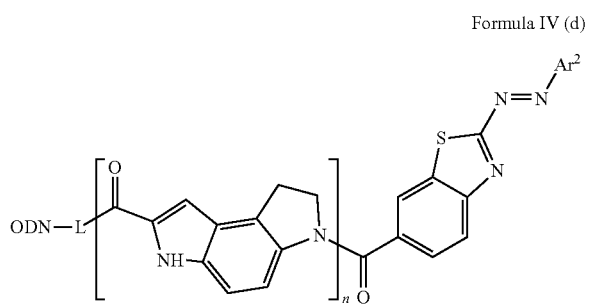

wherein n is 1, 2 or 3.

Oligonucleotide Conjugate Preparation

Oligonucleotide conjugates of the disclosure (including those of Formula IV (a) and IV (b)) can be synthesized in a variety of ways. One way is to use the activated derivatives of Formula III, wherein X is a leaving group. One such leaving group is the pentafluorophenyloxy (—OPFP) group exemplified in this disclosure. Other examples of suitable leaving groups are N-succinimidyloxy and p-nitrophenyloxy groups as practiced in Greg T. Hermanson, Bioconjugate Techniques, Elsevier 1996, incorporated by reference.

These derivatives can be conveniently reacted with oligonucleotides bearing primary or secondary aliphatic amino groups to form covalent amide bonds between oligonucleotides and diaryl-azo compounds of the disclosure. Description and examples of suitable procedures for such conjugation reactions can be found, for instance, in Kutyavin et al., Current Protocols in Nucleic Acid Chemistry, 2003, 8.4.1-8.4-21 and Lukhtanov et al., Bioconjugate Chem. 1995, 6, 418-426.

These activated derivatives can also be used to introduce a variety of functional groups suitable for other types of conjugation reactions examples of which are reviewed in Hermanson, in Bioconjugate Techniques, Elsevier, 1996, and Kolb et al., Angewandte Chemie, 2001, 40, (11), 2004-2021.

Figure 2:
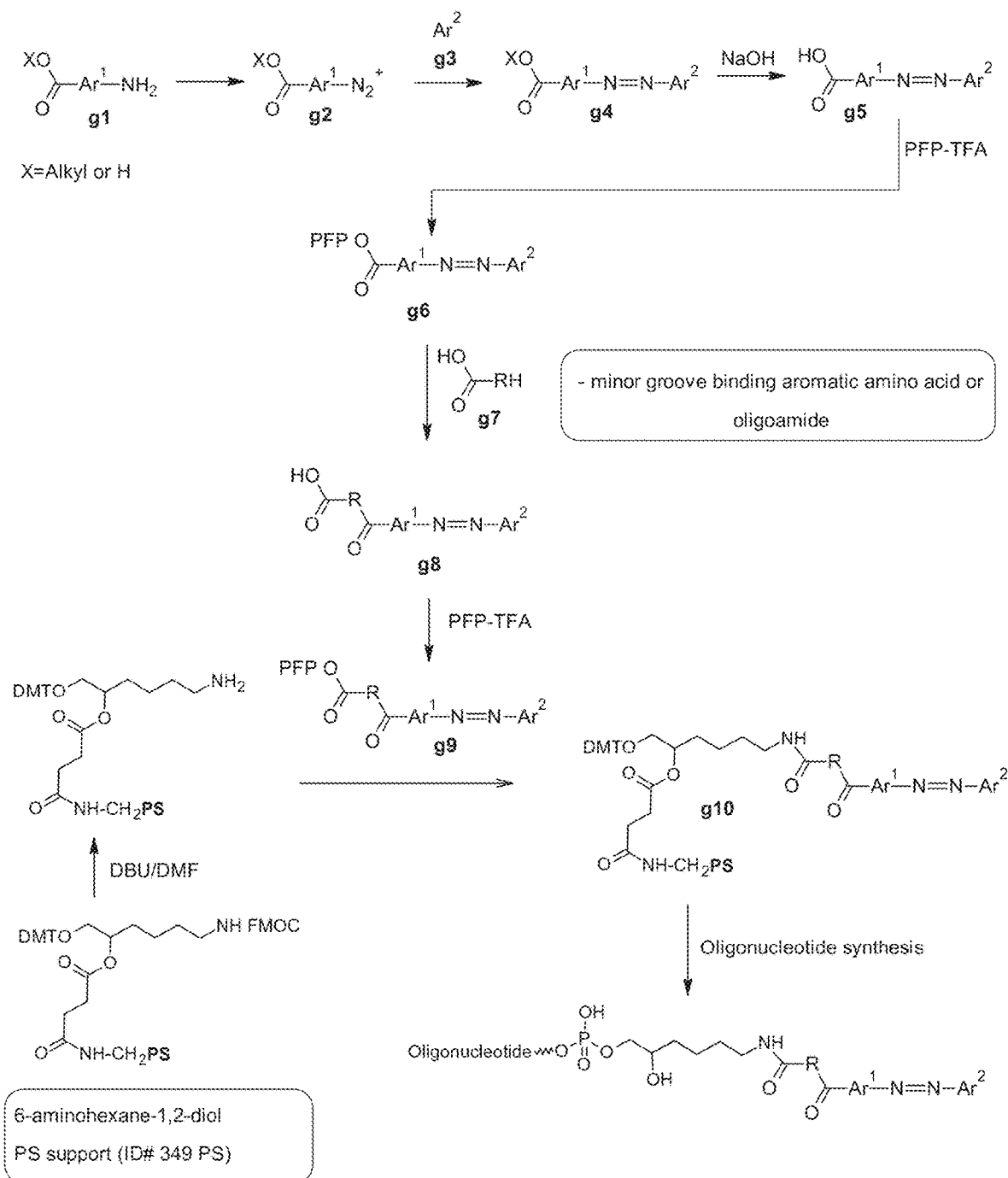
FIG. 2 shows a generic synthetic Scheme 1 for the preparation of pentafluorophenyl (PFP) esters g9 and synthesis supports g10.

A generic procedure for the preparation of diaryl-azo derivatives of Formula III, wherein X is PFPO, is depicted in reaction Scheme 1 (FIG. 2). The starting aromatic amino ester (or acid) g1 is diazotized using nitrous or nitrosylsulfuric acid to give diazo intermediate g2, which is then coupled with an electron-rich aromatic compound g3 to yield diaryl-azo carboxylic ester g4 or acid g5. The obtained diaryl-azo derivatives g4 and g5 are predominantly trans-isomers in regard to orientation of the aryl groups around the azo bond. Other known methods for the preparation of diaryl-azo derivatives, for instance, reviewed in Chem. Soc. Rev., 2011, 40, 3835-3853, can also be applied to produce the required g5 intermediates. The diaryl-azo acid g5 is converted to PFP ester g6 by reaction with pentafluorophenyl trifluoroacetate (PFP-TFA). Alternatively, using reagents and procedures known in the art, a variety of different activated esters can be prepared starting from carboxylic acids g5. The activated PFP esters g6 are reacted with minor groove binding aromatic amino acids (or peptides) g7 to yield carboxylic acids g8. The amino acid and dipeptide exemplified in this specification is 3,6,7,8-tetrahydro-benzo[1,2-b:4,3-b']dipyrrole-2-carboxylic acid (CDPI) and 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (CDPI$_2$), respectively. CDPI and CDPI$_2$ are fragments of known minor grove binding agent CDPI$_3$ (Boger et al. J. Org. Chem., 1987, 52, 1521). Other examples of suitable g7 compounds are based on N-methylpyrrole, N-methylimidazole, N-methylhydroxypyrrole, thiazole amino carboxylic acids, building blocks of distamycin and lexitropsin, known minor groove binding antibiotics. The carboxylic acid g8 is reacted with PFP-TFA PFP to yield the desired activated esters g9 suitable for conjugation with amine-modified oligonucleotides to yield oligonucleotide conjugates of Formula IV (a). Alternatively, non-activated g8 acid derivatives can be conjugated to amine-modified oligonucleotides in the presence of activating agents such as 1-ethyl-3-(3-dimethylaminopropyl)carbodiimide (EDC). Reagents for the preparation of amine-modified oligonucleotides, including DNA synthesis solid supports and phosphoramidites, are commercially available.

Figure 3A:
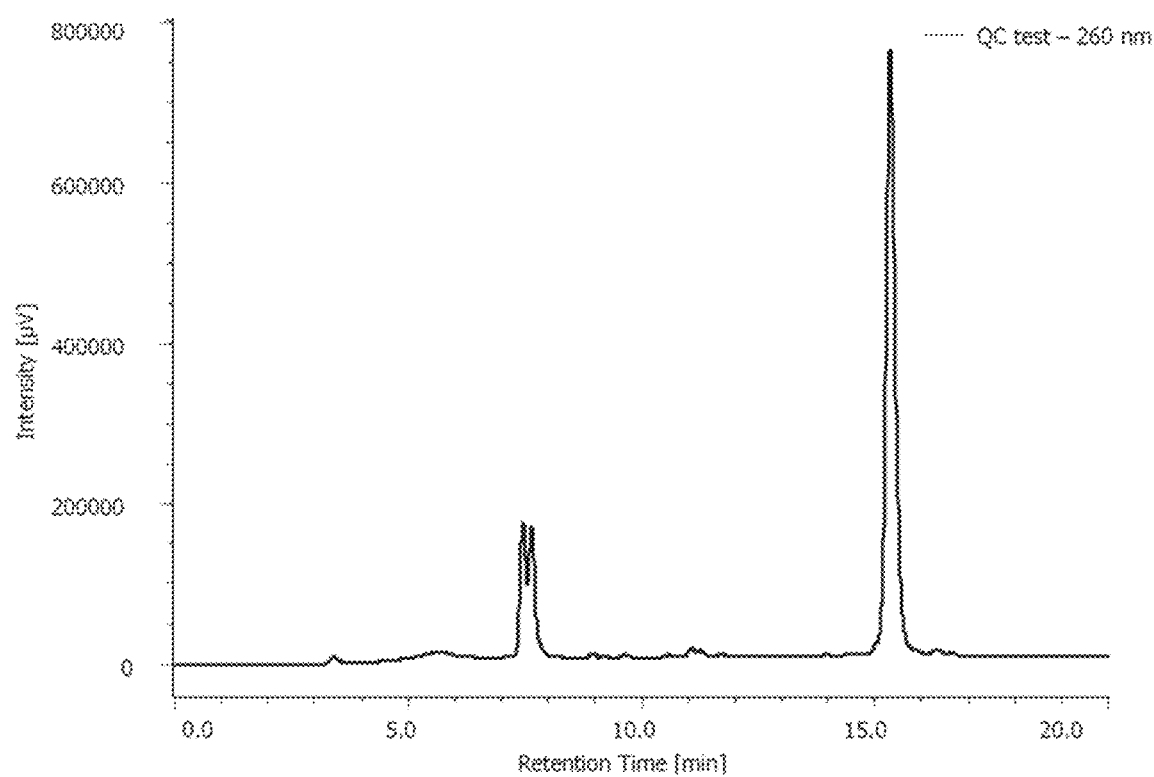
FIG. 3A shows an analytical HPLC of the T8-477 oligonucleotide conjugate prepared according to generic Scheme 1.
Figure 3B:
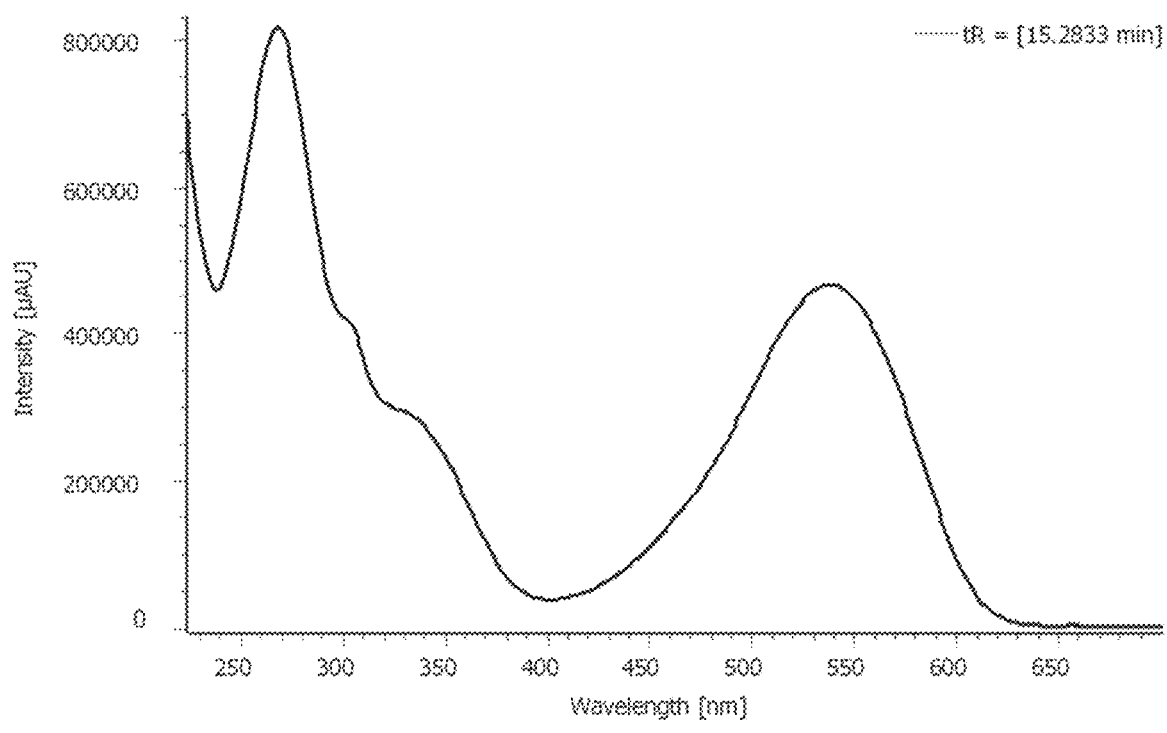
FIG. 3B shows photo diode array (PDA) UV-VIS spectra of the main peak of the T8-477 oligonucleotide conjugate prepared according to generic Scheme 1.
Figure 4B:
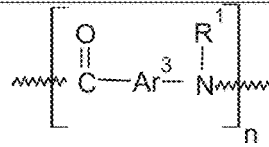
FIG. 4B shows structures and absorption maxima of the T8 oligonucleotide conjugates synthesized according to reaction Scheme 1.
Figure 4B:
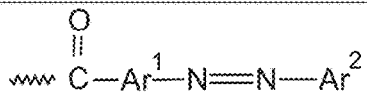
Figure 4B:
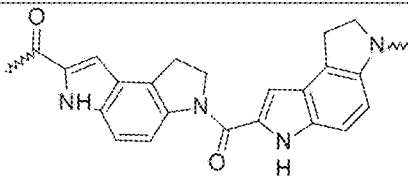
Figure 4B:
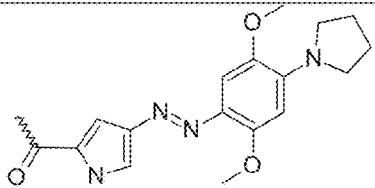
Figure 4B:
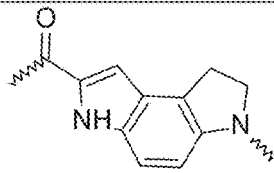
Figure 4B:
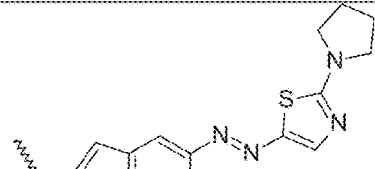
Figure 4B:
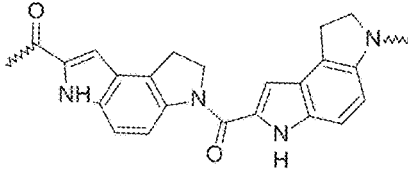
Figure 4B:
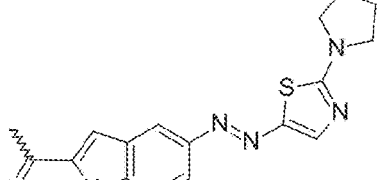
Figure 4B:
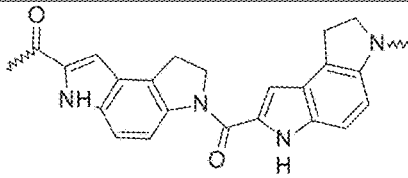
Figure 4B:
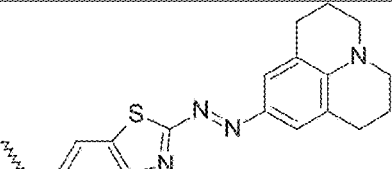
Figure 4B:
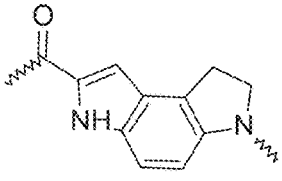
Figure 4B:
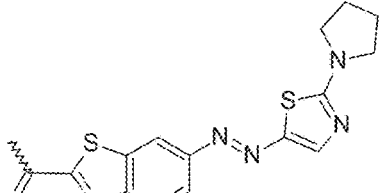
Figure 4B:
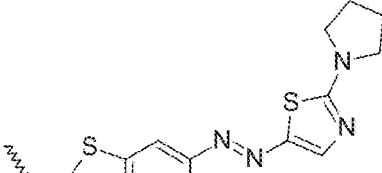
Figure 4C:
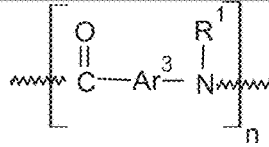
FIG. 4C shows structures and absorption maxima of the T8 oligonucleotide conjugates synthesized according to reaction Scheme 1.
Figure 4C:
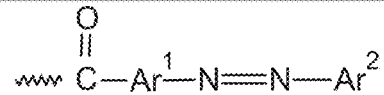
Figure 4C:
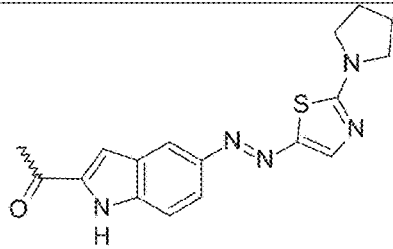
Figure 4C:
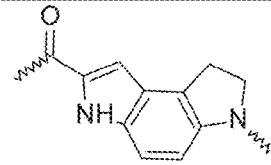
Figure 4C:
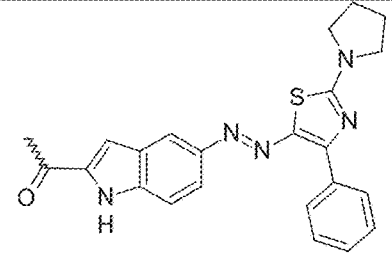
Figure 4C:
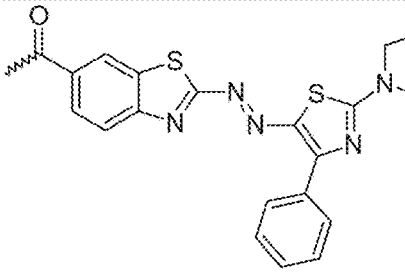
Figure 4C:
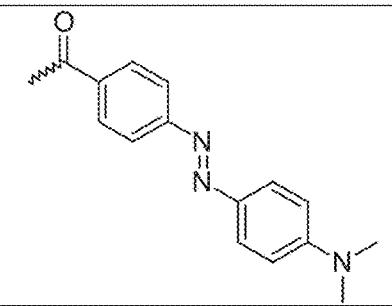

The activated esters g9 are also used to react with linker moieties. Those linker moieties may be mono- or polyfunctional and contain various functional groups such as maleimide, biotin, azide, alkyne, amine, hydroxyl, DMT-protected hydroxyl, etc. One particular type of poly functional linker is a 6-aminohexane-1,2-diol and is suitable for the preparation of solid synthesis supports as illustrated in scheme 1 (FIG. 2). In this approach the linker is attached to the solid support via a cleavable (during oligonucleotide cleavage and deprotection step) succinate linker utilizing the secondary hydroxyl group while the primary hydroxyl and the amino groups are protected with the DMT and FMOC groups, respectively. This support is prepared in the manner described in U.S. Pat. No. 6,492,346. The FMOC group can be selectively removed by treating the starting solid support with DBU yielding free amino group available for the following reaction with PFP esters g9. The resultant solid supports g10 are suitable for on-line oligonucleotide synthesis starting from the DMT-protected primary hydroxyl group. Following the oligonucleotide synthesis and deprotection, oligonucleotide conjugates of Formula IV (a) are obtained. Both 3' end and 5' end conjugation can be achieved depending on whether 3' or 5' nucleoside phosphoramidites are used in the synthesis. FIG. 3A shows the HPLC analysis and FIG. 3B shows the UV spectra of an oligonucleotide synthesized using a synthesis support of type g10. This example demonstrates that the general approach described in scheme 1 provides the desired oligonucleotide conjugates in good yield and the conjugates can be readily purified by reverse phase chromatography.

FIG. 4A-4D show the structures and absorption maxima of the T8 oligonucleotide conjugates synthesized according to reaction scheme 1. FIG. 4A-4D show the relationship between the DSQ structures and absorption maxima of the T8 oligonucleotide conjugates synthesized according to reaction Scheme 1. Generally, the benzothiazole-substututed DSQ demonstrate more red-shifted absorption spectra than the phenyl or indole-substituted ones. The position of the absorption band is directly related to the efficiency of FRET-based fluorescence quenching as specified by Lakowicz, 2007.

Another example of a suitable linker for the preparation of DNA synthesis supports of the disclosure is hydroxyprolinol, a trifunctional reagent that has an amino, a primary and a secondary hydroxyl group. This linker as well as examples of other trifunctional reagents having an amino, primary and a secondary hydroxyl group, are described in U.S. Pat. No. 5,512,667. The primary hydroxyl group in this example is protected with a dimethoxytrityl group whereas the secondary hydroxyl and amino groups are available for further modifications.

The synthesis support used in synthetic Scheme 1 is a highly cross-linked porous styrene-divinylbenzene copolymer further aminomethylated to enable the surface chemistry (Applied Biosystems, PN 360865C). Another example of synthesis support is Controlled Pore Glass (CPG) (Glen Research, Sterling, Va.), which is commercially available in different pore sizes and with long chain alkylamine extension for more efficient phosphoramidite coupling.

Figure 7A:
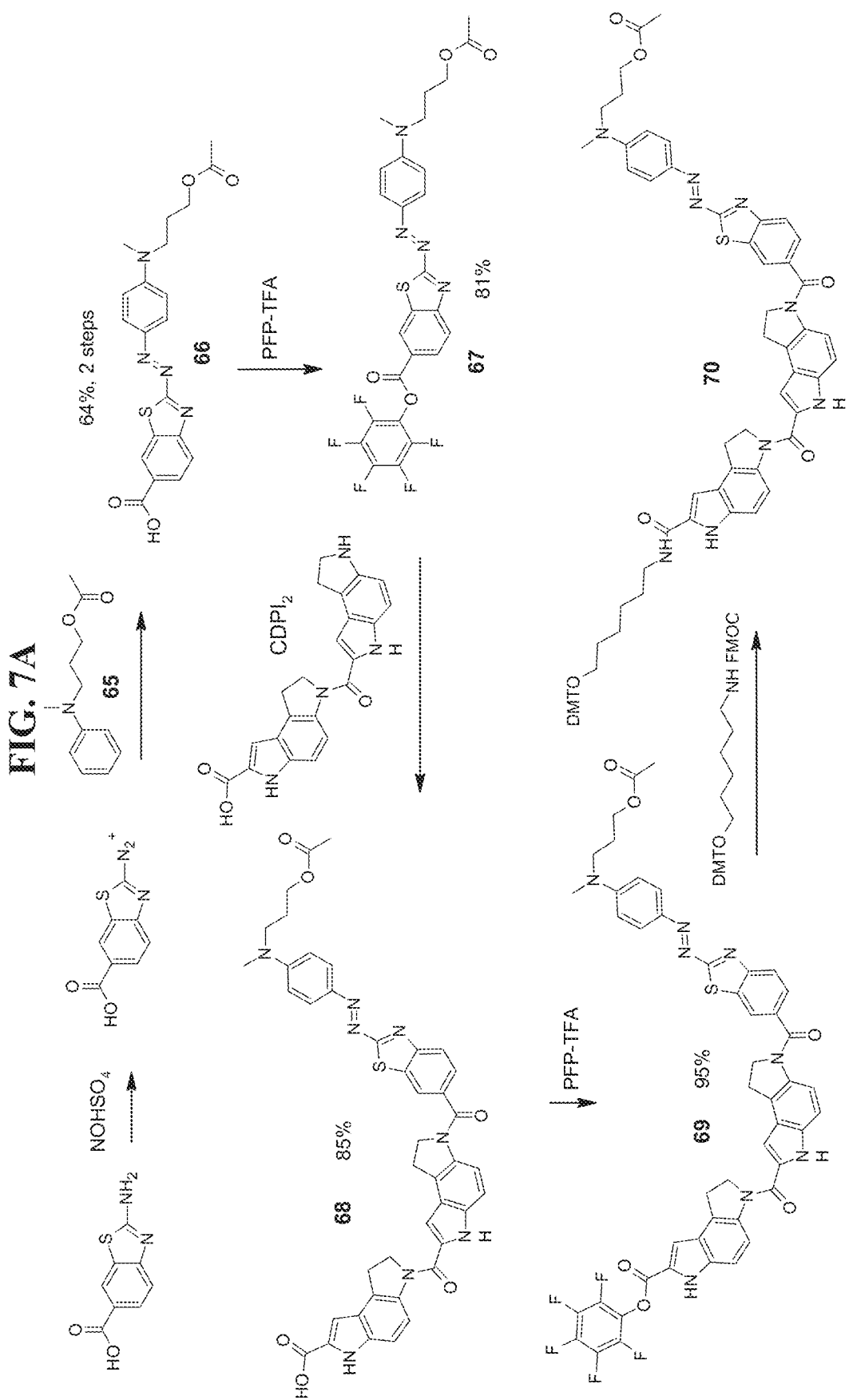
FIG. 7A shows steps in reaction Scheme 3, synthesis of polystyrene support ID #480.
Figure 7B:
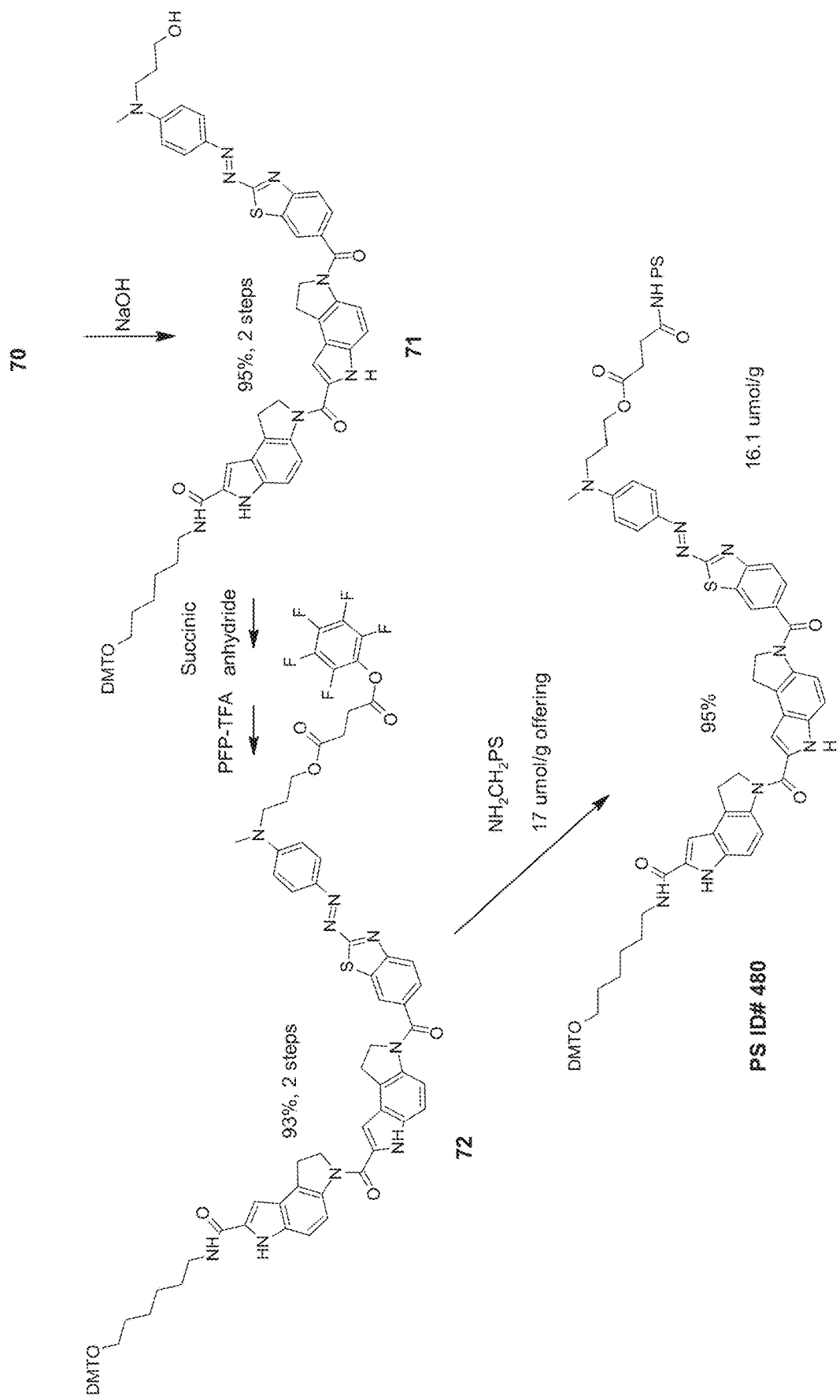
FIG. 7B shows steps in reaction Scheme 3, synthesis of polystyrene support ID #480.

Oligonucleotide conjugates of Formula IV (a) can also be obtained using a polystyrene synthesis support ID #480 exemplified in reaction scheme 3 (FIG. 7A-7B). The synthesis supports of this type can be prepared using reagents of general Formula III, wherein X is a linking group with a DMT-protected hydroxyl group and either Ar$^1$ or Ar$^2$ contain a functional group for covalent attachment to a synthesis solid support via a cleavable (during oligonucleotide deprotection) linker.

Figure 8A:
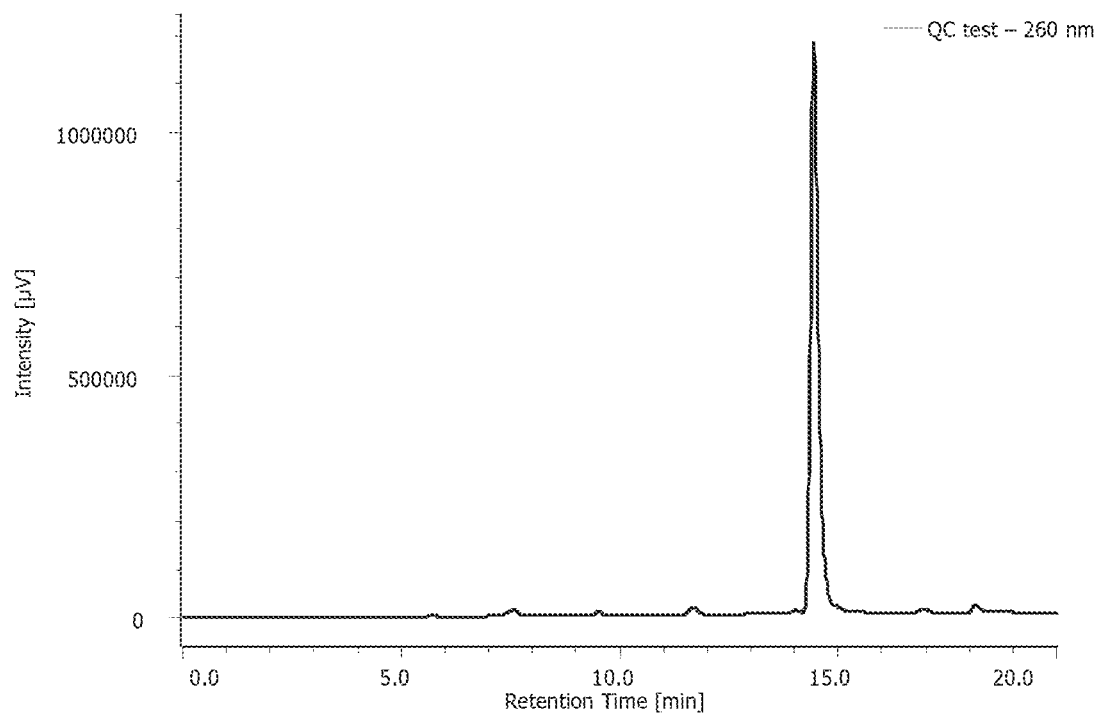
FIG. 8A shows an analytical HPLC of the T8-oligonucleotide conjugate synthesized starting from the polystyrene support ID #480.
Figure 8B:
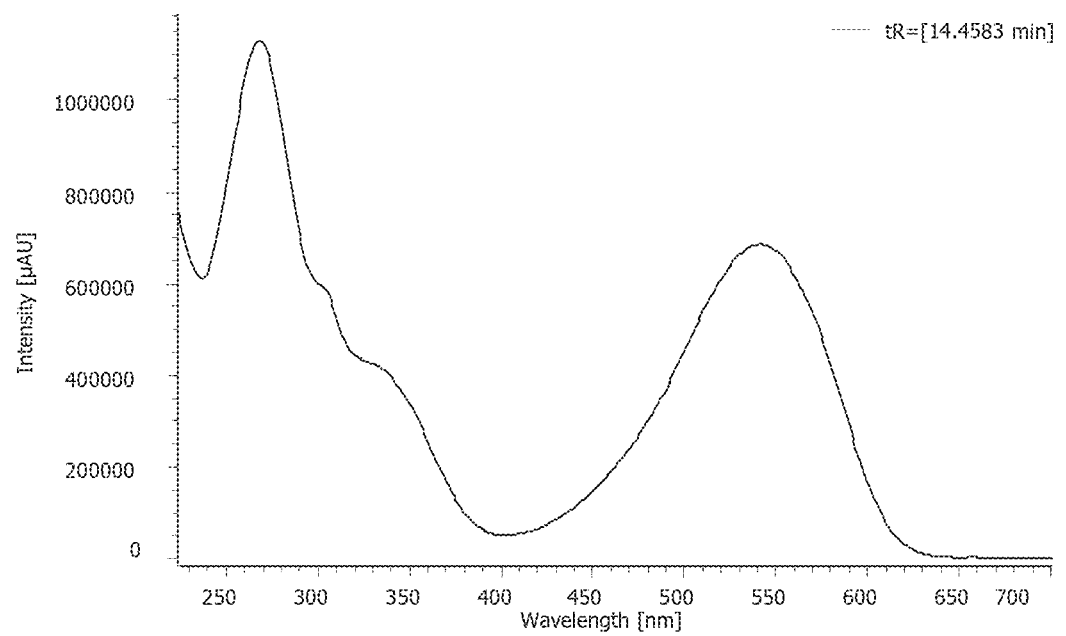
FIG. 8B shows PDA UV-VIS spectra of the main peak and product structure of the T8-oligonucleotide conjugate synthesized starting from the polystyrene support ID #480.
Figure 8B:
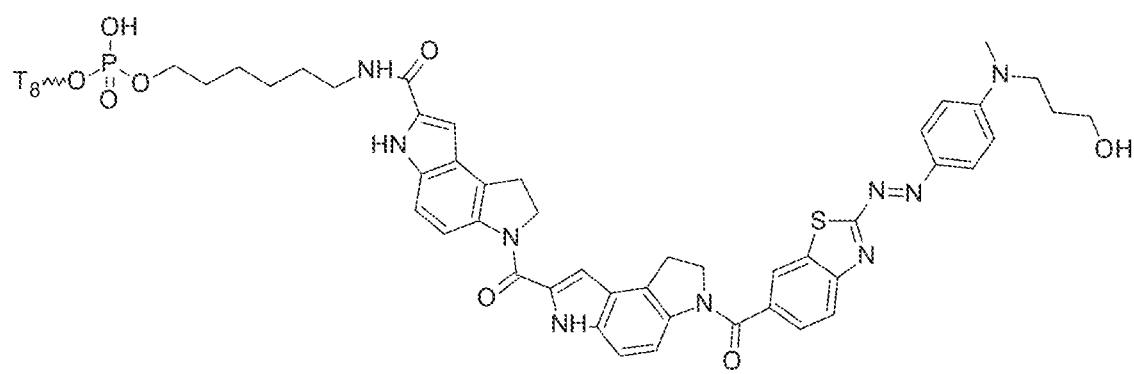

In the particular example depicted in reaction scheme 3, diaryl-azo-dye 66 is prepared by diazotization of 2-amino-1,3-benzothiazole-6-carboxylic acid followed by coupling with N-substituted aniline analog 65. The acid 66 is converted into activated PFP ester 67 for the following condensation with CDPI$_2$ dipeptide yielding intermediate 68. This intermediate is activated via the formation of PFP ester 69 and then reacted with O-DMT-protected aminohexanol to afford intermediate 70 with two orthogonally-protected hydroxyl groups. The acetyl protection of the intermediate 70 is selectively saponified to give hydroxyl intermediate 71. To introduce the cleavable succinate linker, hydroxyl intermediate 71 is reacted with succinic anhydride and then activated with PFP-TFA. The obtained PFP ester 72 is reacted with aminomethyl polystyrene support (e.g. used in synthetic scheme 1) to yield synthesis support ID #480. Analytical HPLC is shown in FIG. 8A and PDA UV-VIS spectra is shown in FIG. 8B for an example of oligonucleotide synthesis using the synthesis support ID #480. It demonstrates that the DSQ ID #480-modified oligonucleotide conjugates can be synthesized in exellent yield and be readily purified by reverse phase chromatography.

Figure 5A:
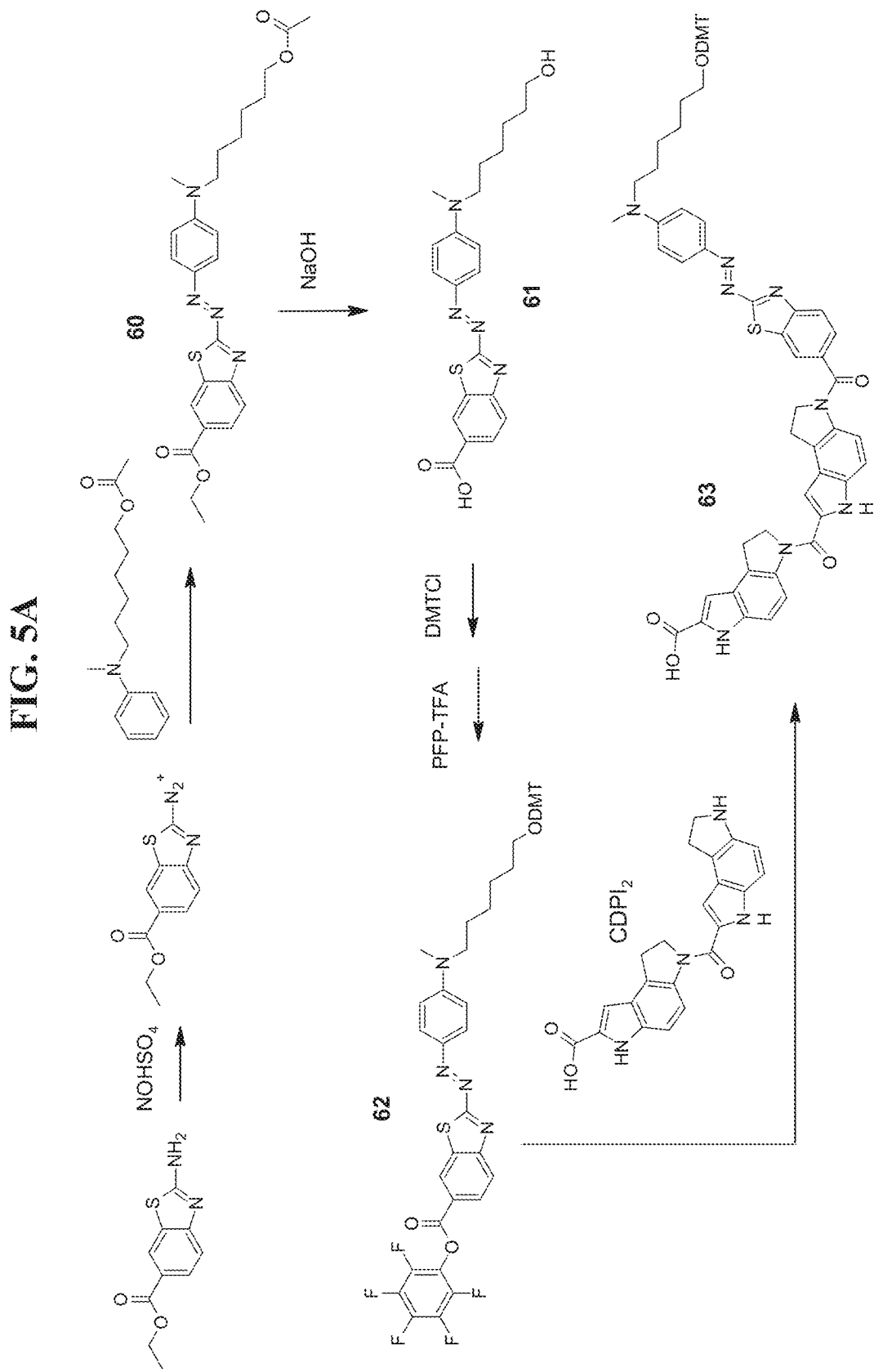
FIG. 5A shows steps in reaction Scheme 2, synthesis of polystyrene support ID #478.
Figure 5B:
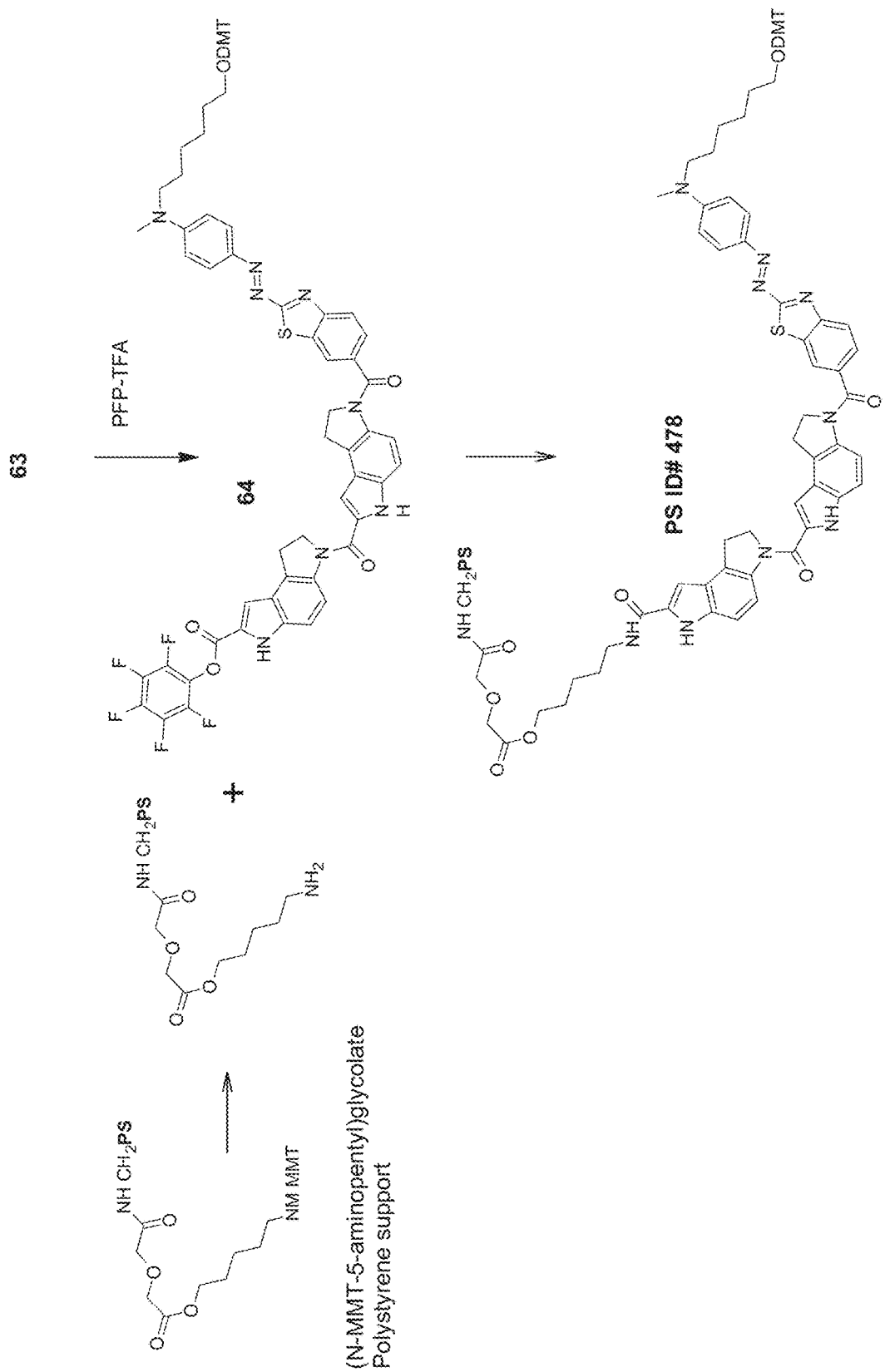
FIG. 5B shows steps in reaction Scheme 2, synthesis of polystyrene support ID #478.
Figure 6A:
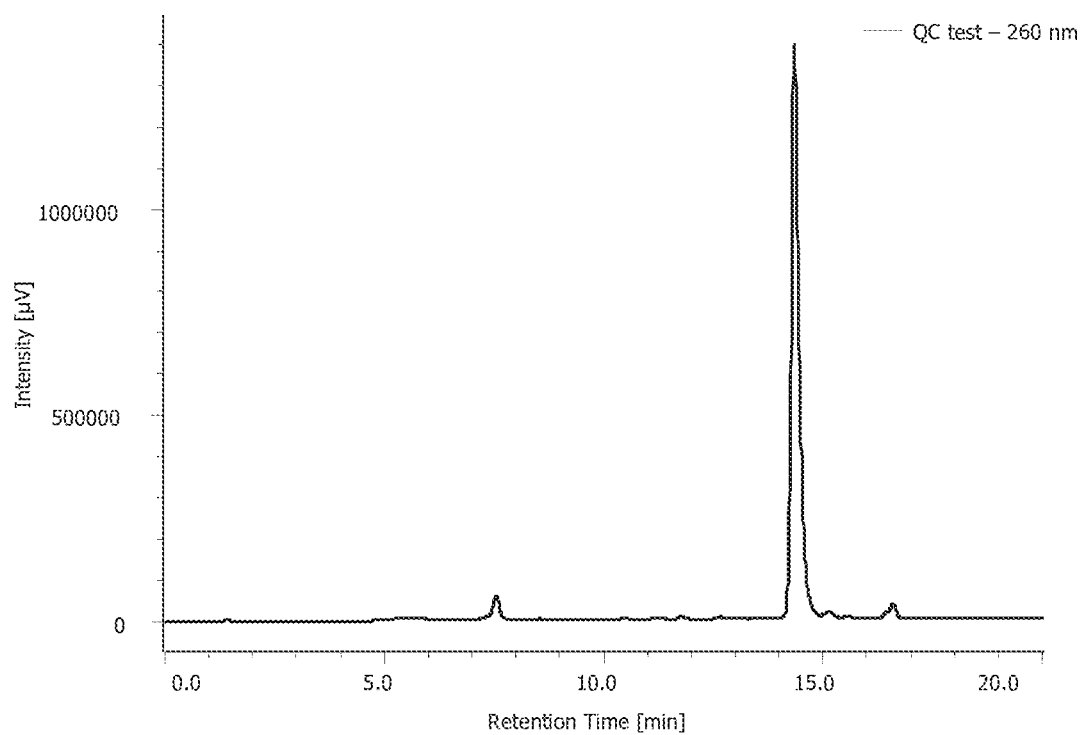
FIG. 6A shows an analytical HPLC of the T8-oligonucleotide conjugate synthesized starting from the polystyrene support ID #478.
Figure 6B:
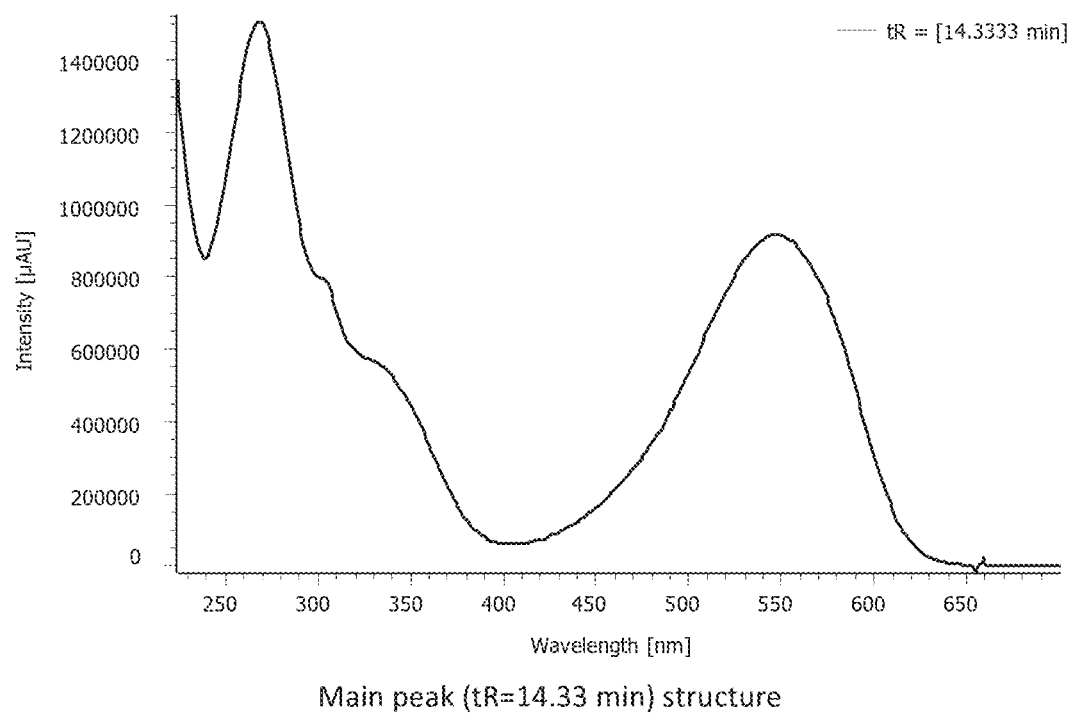
FIG. 6B shows PDA UV-VIS spectra of the main peak and product structure of the T8-oligonucleotide conjugate synthesized starting from the polystyrene support ID #478.
Figure 6B:
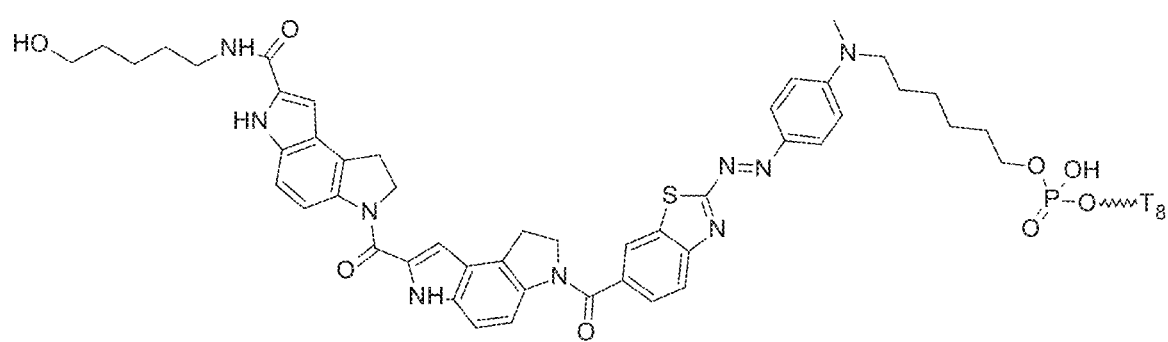

Some oligonucleotide conjugates of Formula IV (b) can be prepared using the synthesis solid support ID #478 prepared according to the reaction scheme 2 (FIG. 5A-5B). The approach depicted in this scheme requires an introduction of a hydroxyl group, starting point for oligonucleotide synthesis, into the diaryl-azo section of compounds of Formula I. This is achieved in the first step of the reaction scheme by using 6-[methyl(phenyl)amino]hexyl acetate (WO 2008008481), an aniline analog with a protected 6-hydroxyhexyl linker. This aniline is coupled with ethyl 2-diazo-1,3-benzothiazole-6-carboxylate to yield diaryl-azo dye 60. The bis-ester 60 is then saponified to give hydroxyl acid 61. The hydroxyl group is then DMT-protected followed by activation with PFP-TFA to afford PFP ester 62. Condensation of the ester with $CDPl_2$ produced intermediate 63, which then was activated with PFP-TFA to afford the desired PFP ester 64, suitable for the following solid support chemistry. The starting N-MMT-5-aminopentylglycolate polystyrene support (prepared according to U.S. Pat. No. 7,759,126) was first deprotected with trichloroacetic acid in dichloromethane and then reacted with the PFP ester 64 to give polystyrene synthesis support ID #478. An analytical C18 HPLC trace of a T8 oligonucleotide synthesis using this support is shown in FIG. 6A, with PDA UV-VIS spectra of the main peak and product structure shown in FIG. 6B. This example demonstrates that the oligonucleotide conjugates prepared according to scheme 2 can be synthesized in excellent yield and be readily purified by reverse phase chromatography.

Figure 9A:
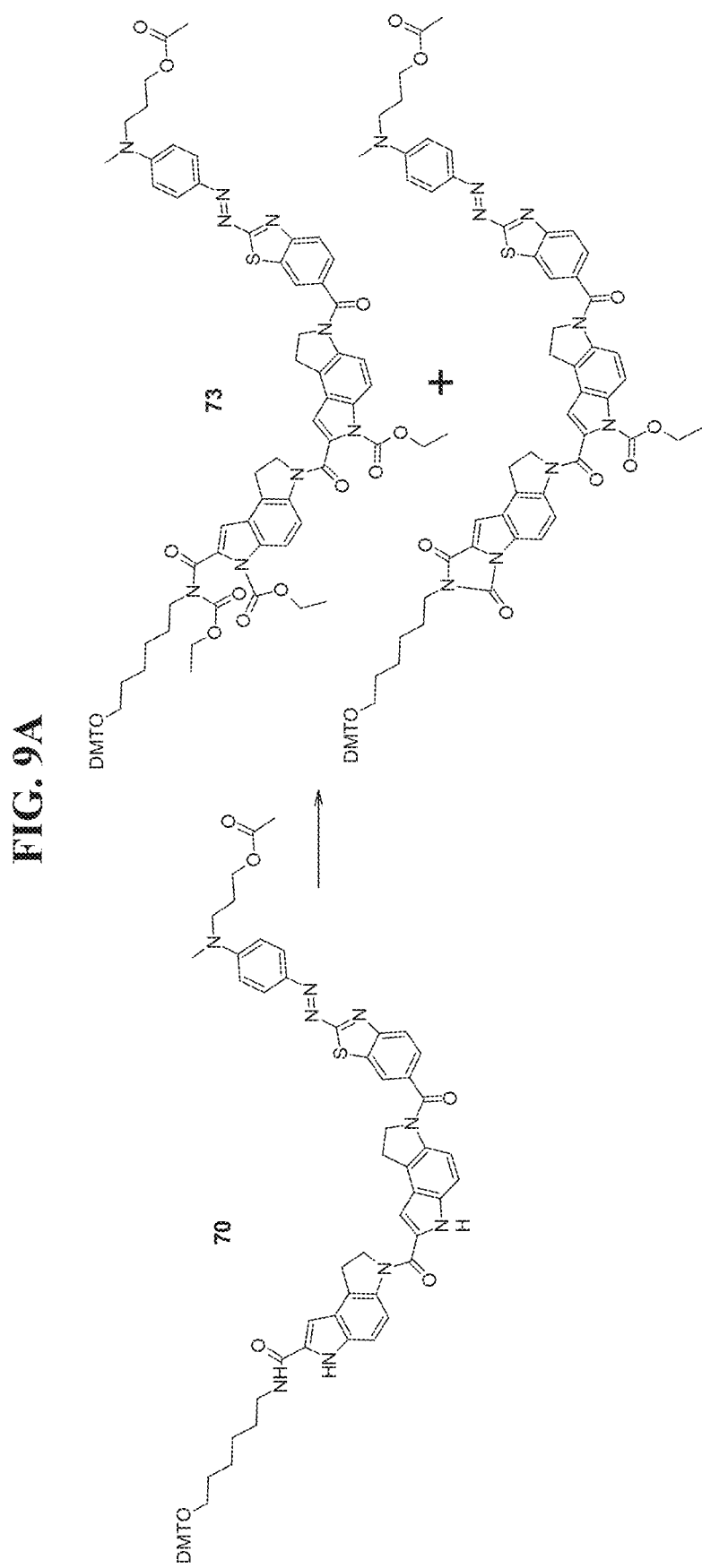
FIG. 9A shows steps in reaction Scheme 4, synthesis of phosphoramidite 75.
Figure 9B:
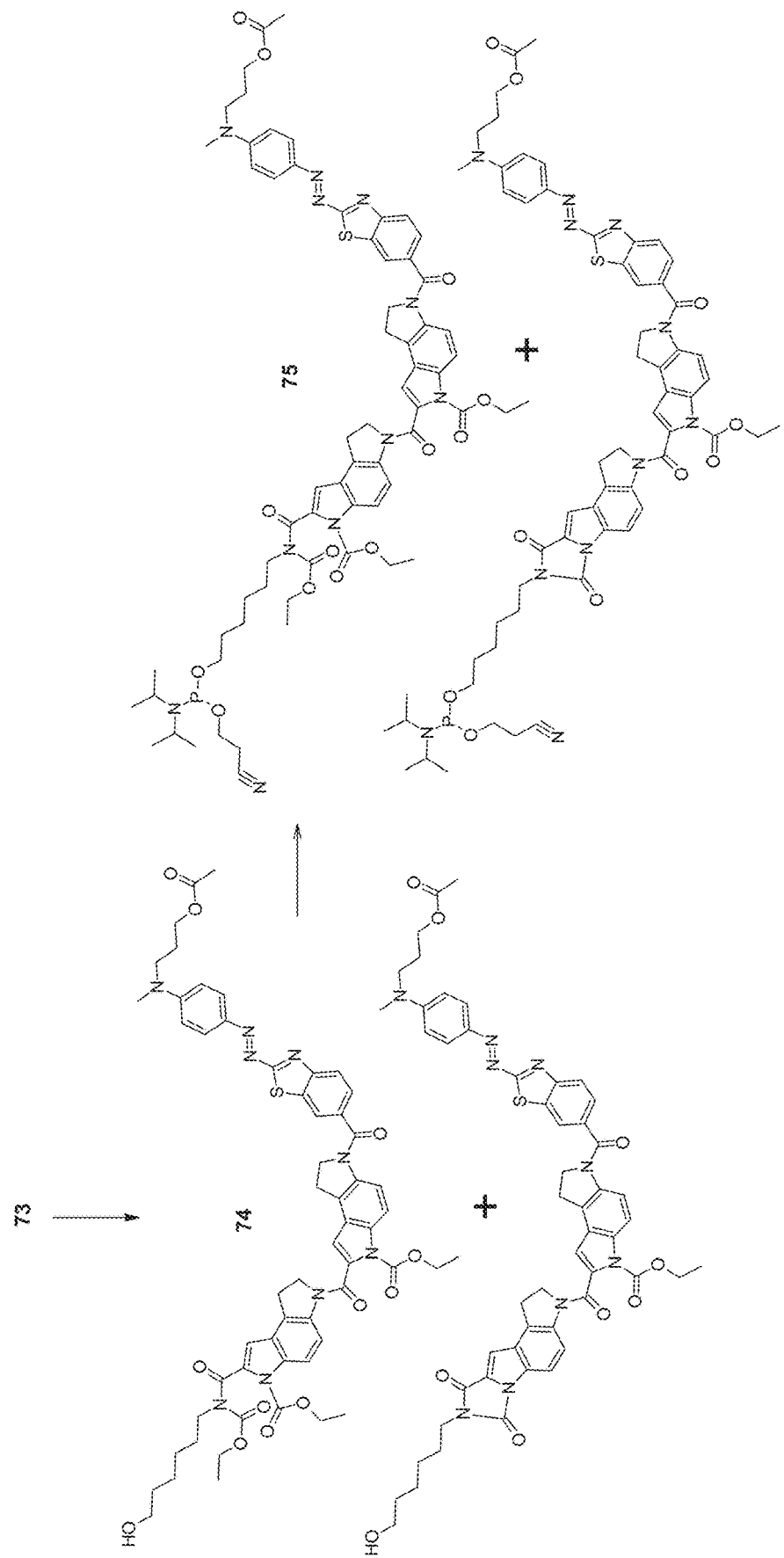
FIG. 9B shows steps in reaction Scheme 4, synthesis of phosphoramidite 75.
Figure 10A:
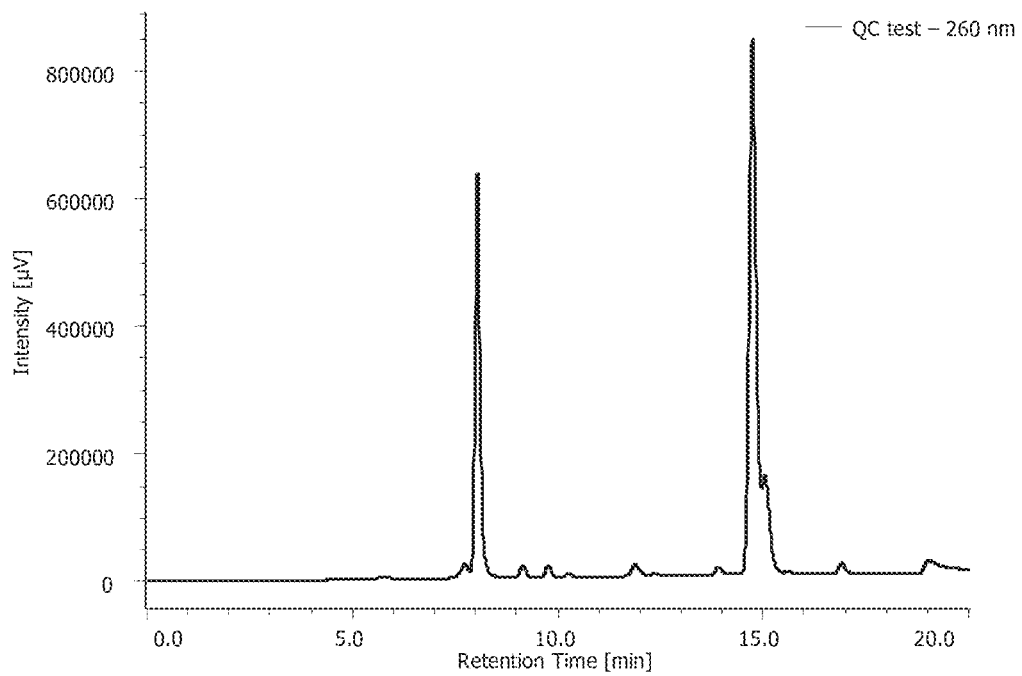
FIG. 10A shows analytical HPLC of the T8-oligonucleotide conjugate synthesized using phosphoramidite 75.
Figure 10B:
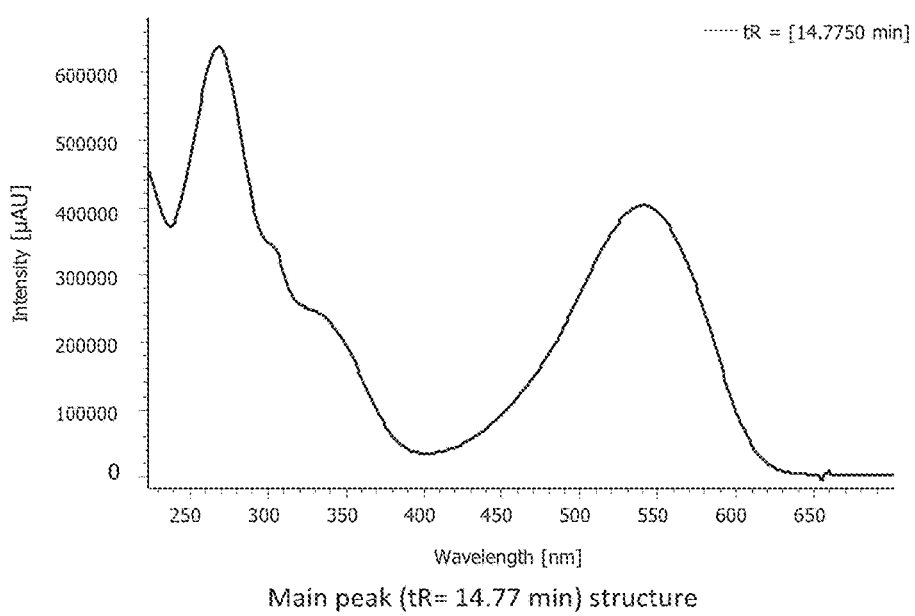
FIG. 10B shows PDA UV-VIS spectra of the main peak and product structure of the T8-oligonucleotide conjugate synthesized using phosphoramidite 75.
Figure 10B:
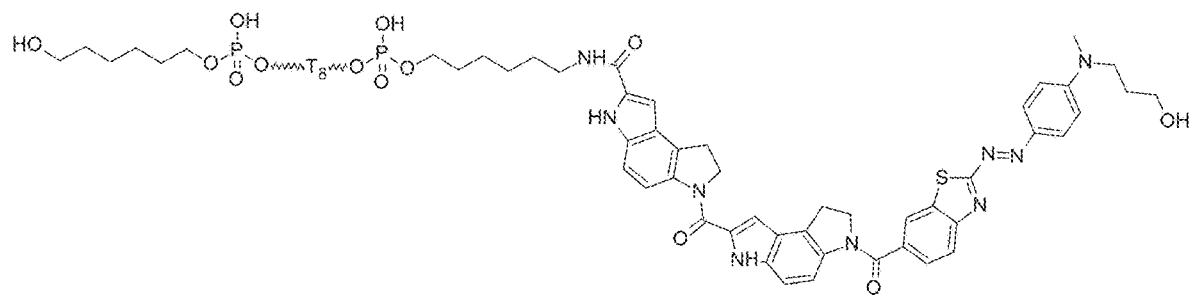

2-Cyanoethyl N,N-diisopropylphosphoramidite chemistry is another way to prepare oligonucleotides bearing compounds of the disclosure. One example of a suitable phosphoramidite reagent is shown in reaction scheme 4 (FIG. 9A-9B). In this approach, the intermediate 70 (reaction scheme 3) is first reacted with diethylpyrocarbonate to protect the indole and amide NH groups yielding intermediate 73. The DMT group is then selectively removed and the resultant alcohol 74 is converted into the phosphoramidite 75 by reaction with 2-cyanoethyl N,N,N',N'-tetraisopropylphosphordiamidite. FIG. 10A shows an analytical C18 HPLC trace of a T8 oligonucleotide synthesis using this phosphoramidite, and FIG. 10B shows PDA UV-VIS spectra of the main peak and product structure. This demonstrates that the oligonucleotide conjugates prepared using the phosphoramidite 75 can be synthesized in a fair yield and be purified by reverse phase chromatography. Further improvement in purity in efficiency of the phosphoramidite approach can be achived through the use of N-substituted aminohexanol in scheme 3 (e.g. N-methyl-6-aminohexanol as described in U.S. Pat. No. 9,056,887) by eliminating the formation of the imidazolidine-2,4-dione side-product shown in scheme 4 (FIG. 9A-9B).

Figure 11A:
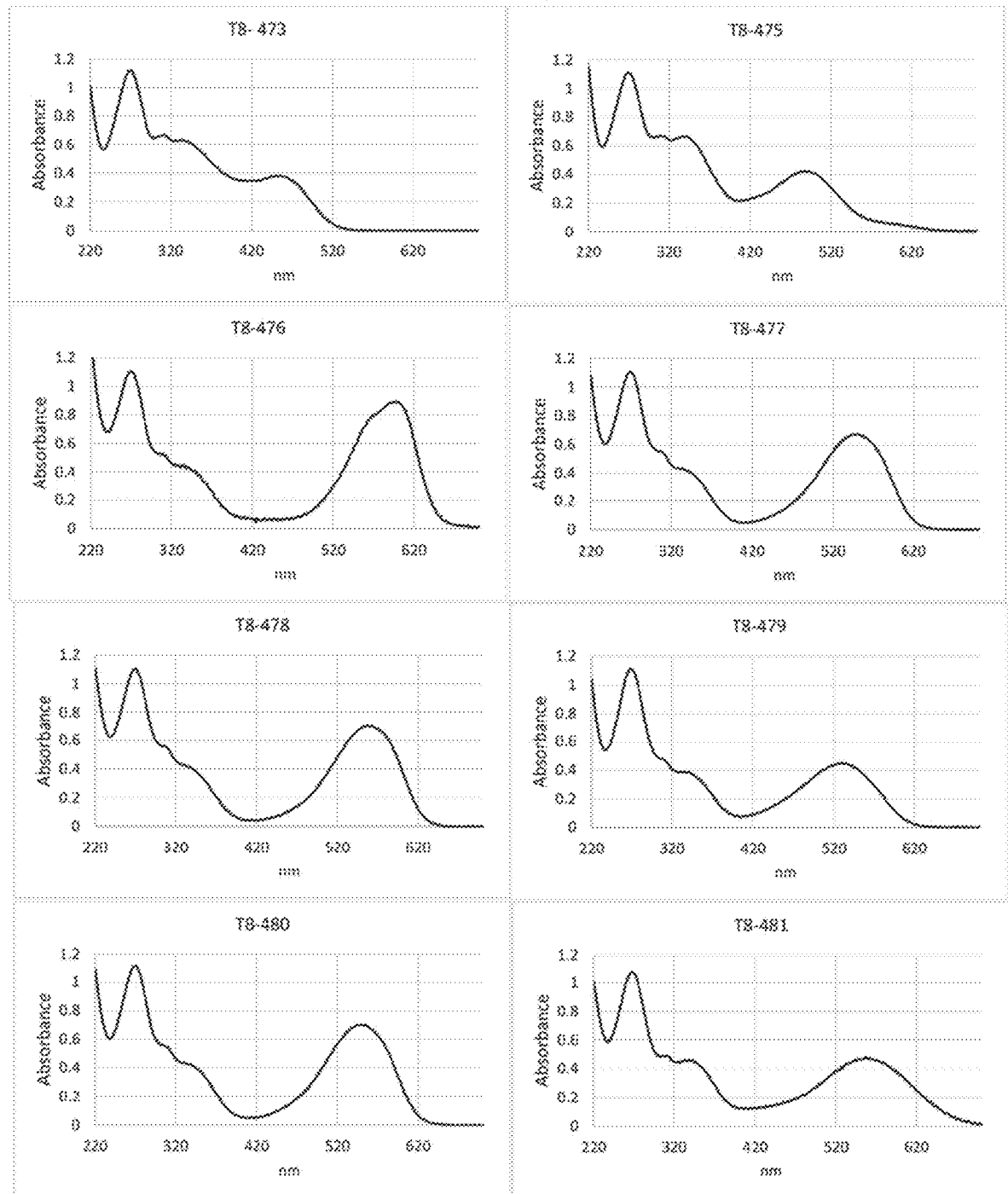
FIG. 11A shows UV-VIS absorption spectra of T8-DSQ conjugates.
Figure 11B:
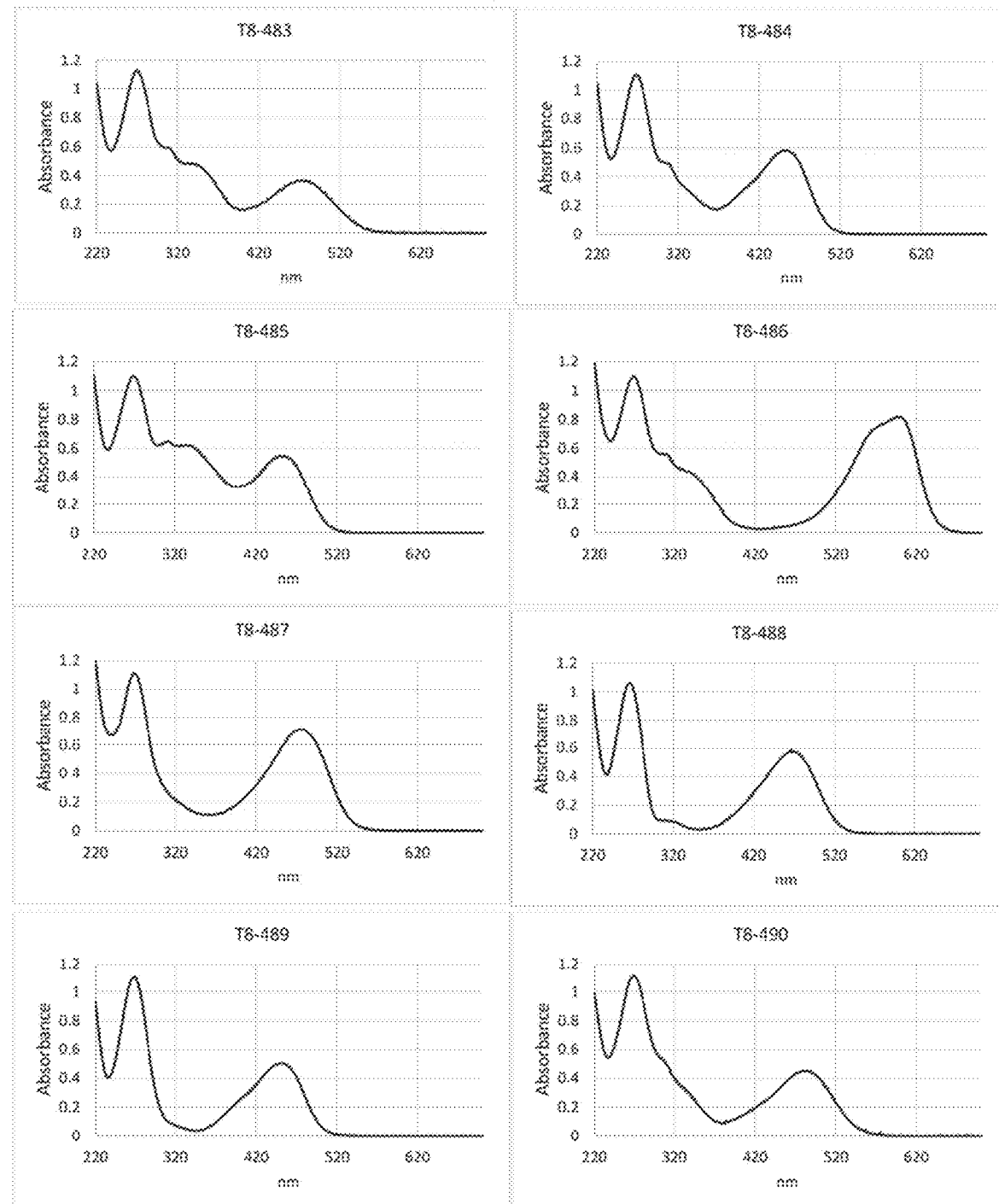
FIG. 11B shows UV-VIS absorption spectra of T8-DSQ conjugates.
Figure 11C:
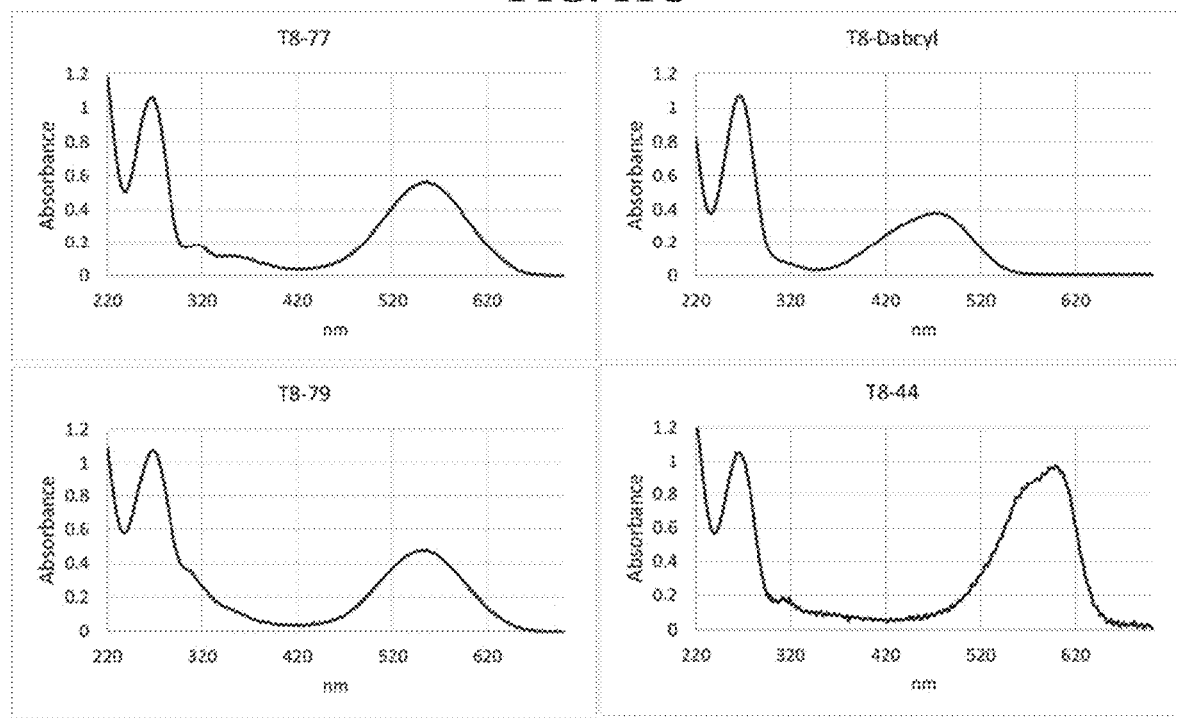
FIG. 11C shows UV-VIS absorption spectra of T8-DSQ conjugates.

FIG. 11A-11C show UV-VIS absorption spectra of T8-DSQ conjugates. The absorption bands of these exemplary compounds cover the wavelength range between 400 and 700 nm, which is suitable for efficient FRET quenching of common fluorophores for real-time PCR applications.

Applications of Oligonucleotide Conjugates

Oligonucleotide conjugates of Formula IV (a) and (b) are useful for various application as described below. Preferred embodiments include a method for detecting a target nucleic acid sequence in a sample, comprising contacting the sample with embodiments of the oligonucleotide conjugates described herein, wherein the oligonucleotide conjugate has a nucleic acid sequence at least partially complementary to the target nucleic acid sequence, and wherein the oligonucleotide conjugate further comprises a fluorophore, and detecting a fluorescent signal from the oligonucleotide conjugate upon hybridization to the target nucleic acid sequence. Further preferred embodiments also include the step of amplifying the target nucleic acid sequence. In some preferred embodiments the oligonucleotide conjugate is a primer or a probe.

In one embodiment of Formula IV the DSQ-conjugates comprise a 3'-DSQ and a 5'-fluorophore to yield oligonucleotides of general Formula V:

5'-Fl-ODN-DSQ                    Formula V wherein Fl is a fluorophore and ODN-DSQ is an oligonucleotide conjugate of Formula IV (a) or (b).

Figure 16:
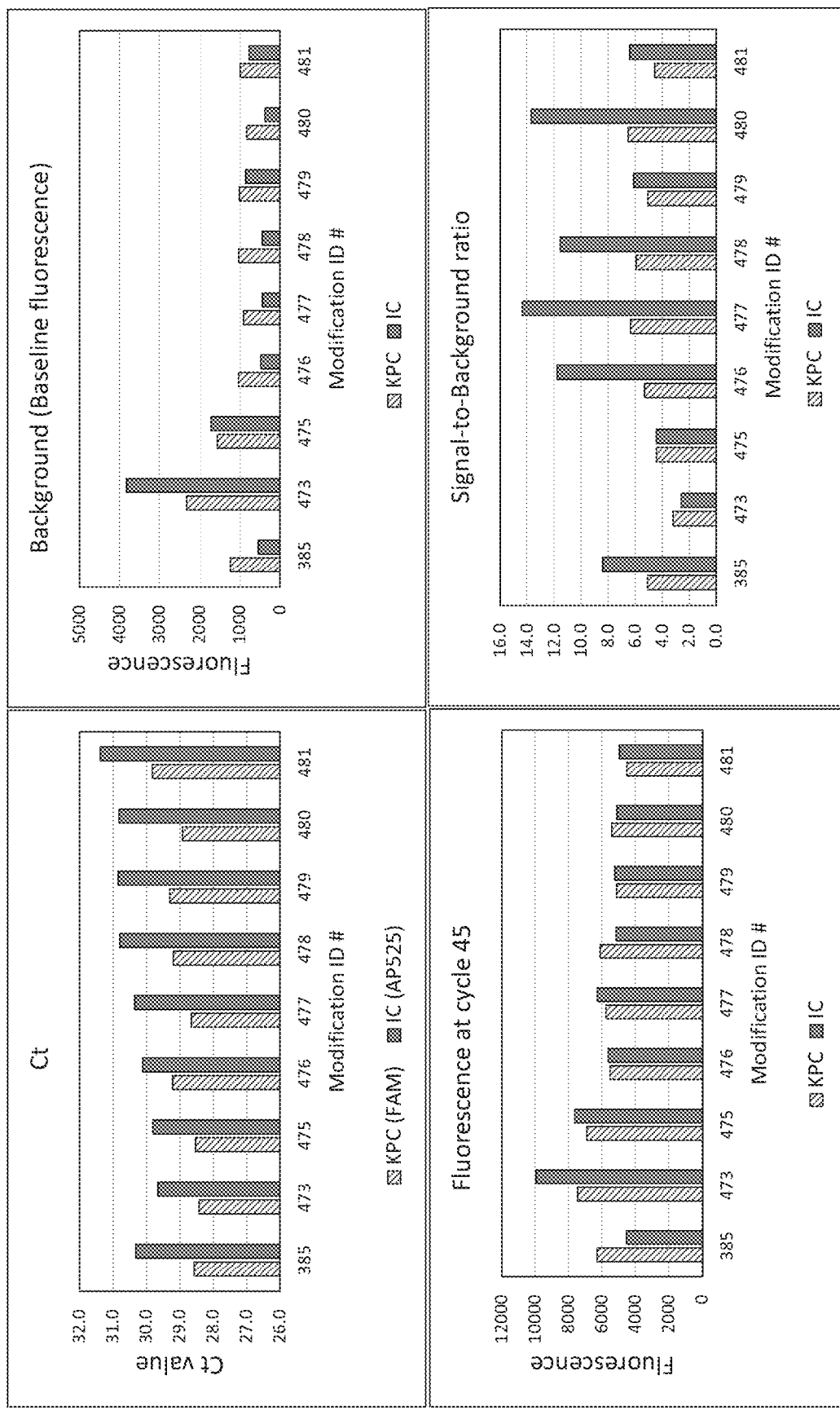
FIG. 16 shows PCR performance of two TaqMan probes labeled with representative DSQ derivatives.

Conjugates of Formula V are particularly useful as DNA probes for fluorescence-based real-time and endpoint PCR applications that rely on the hybridization-dependent 5'-exonuclease activity of DNA polymerase for fluorophore cleavage, also known as the TaqMan technology. Examples of TaqMan PCR applications using conjugates of Formula V are shown in FIG. 16.

In other preferred embodiments, with reference to Formula IV, the oligonucleotide conjugates comprise a 5' DSQ and a 3' fluorophore as represented by Formula VI:

5'-DSQ-ODN-Fl                    Formula VI wherein Fl is a fluorophore and DSQ-ODN is an oligonucleotide conjugate of Formula IV (a) or (b).

Oligonucleotide conjugates of Formula VI are useful as DNA probes for fluorogenic probes whose fluorescence signal is generated due to the hybridization with a target. The 5' DSQ moiety prevents the 5' exonuclease probe degradation. One particular type of such fluorogenic probes is the Molecular Beacon technology, which relies on the stem-loop structure to improve signal-to-background ratio and mismatch discrimination.

In additional preferred embodiments, with reference to Formula IV, the oligonucleoptide conjugates comprise a 5'-DSQ and a 5'-fluorophore positioned adjacent to each other as represented by Formula VII:

5'-DSQ-Fl-ODN                    Formula VII

Figure 14A:
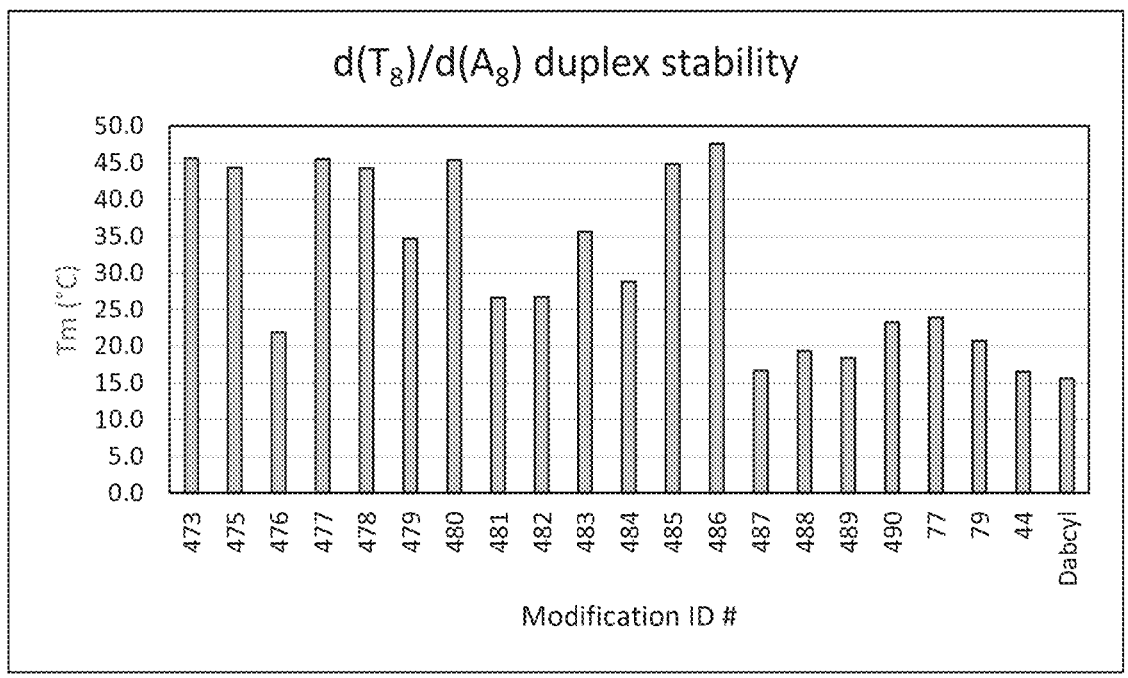
FIG. 14A shows the effects of various DSQ ligands on the $d(T_8)/d(A_8)$ duplex stability.
Figure 14B:
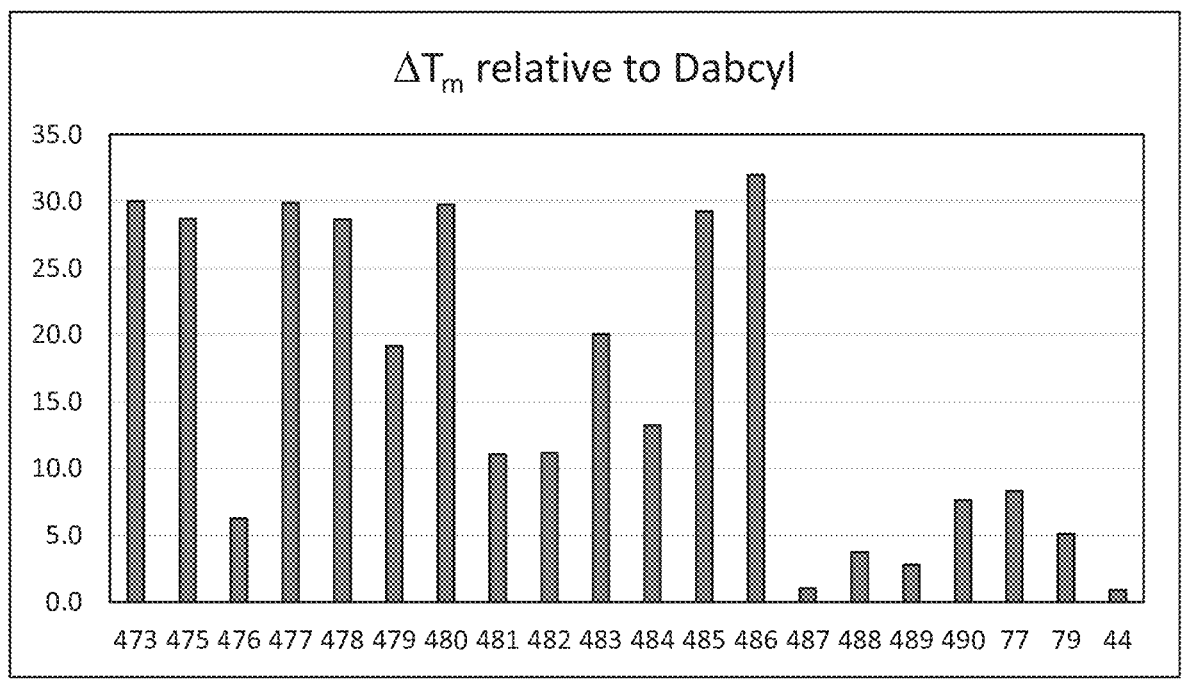
FIG. 14B shows the effects of various DSQ ligands on the $d(T_8)/d(A_8)$ duplex melting temperature.

Such oligonucleotides are useful as hybridization-triggered fuorogenic probes and primers as illustrated in FIGS. 14A-14B and Table 14.

In additional preferred embodiments, the oligonucleotides of Formula IV could be used in digital PCR and arrays (U.S. Pat. Nos. 9,328,384 and 7,759,126 incorporated by reference).

Although not illustrated in Formulas V-VII, in some preferred embodiments the DSQ moiety is covalently attached to an internal position of an oligonucleotide, for example to an amine-tailed nucleobase.

In further preferred embodiments, the DSQ oligonucleotides are used to differentiate single nucleotide polymorphisms as taught in U.S. Pat. No. 6,312,894 and, 7,718,374 incorporated by reference. In a related emobodiment, different targets are detected utilizing melting curve analys as taught in Hymas and Hillyard, 2009, incorporated by reference.

Other applications, not specifically described in this specification but known in the art (for example Didenko, Biotechniques 2001, 31(5): 1106-1121, Kim, Y. et al., Int. J. Clin. Exp. Pathol. (2008) 1, 105-116, and U.S. Pat. No. 7,790,385), are also potential applications of the new derivatives and oligonucleotides of the disclosure.

EXAMPLES

The following examples illustrate the functional performance of oligonucleotides labeled with preferred embodiments of the DSQ derivatives and are not intended to limit the scope of the claims.

Example 1. Preparation of DSQ Intermediates and PFP Esters

Ethyl 5-{(E)-[4-(dimethylamino)phenyl]diazenyl}-1H-indole-2-carboxylate (1)

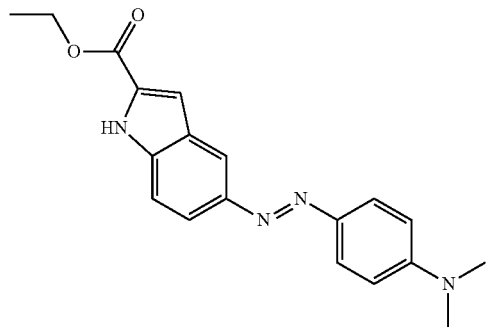 [SMILES: CCOC(=O)c1cc2cc(/N=N/c3ccc(N(C)C)cc3)ccc2[nH]1]

To a suspension of ethyl 5-aminoindole-2-carboxylate (3.0 g, 14.7 mmol) in 80 mL of water was added 2.5 mL of conc. HCl. The stirred suspension was cooled in ice/water bath to 0-4° C. and treated with a solution of NaNO$_2$ (1.1 g, 15.9 mmol) in 20 mL of water via an addition funnel over 5 min. The reaction was stirred at 0-4° C. for 20 min then warmed to room temperature and stirred for another 10 min to give a dark, mostly clear solution. N,N-Dimethylaniline (2.5 mL, 19.7 mmol) was added in one portion and stirring was continued for 1 h. The precipitated solid was collected by filtration, washed with water and resuspended in 50 mL of MeOH. The suspension was heated to reflux then cooled and filtered to collect the precipitated solid. Drying in vacuo afforded 2.9 g (59% yield) of the desired dye 1 as a brown-orange solid. $^1$H NMR (DMSO-d6) δ 12.17 (s, 1H), 8.14 (d, J=1.8 Hz, 1H), 7.83 (dd, J$_1$=9 Hz, J$_2$=2.1 Hz, 1H), 7.79 (d, J=9 Hz, 2H), 7.53 (d, J=8.7 Hz, 1H), 7.31 (d, J=0.9 Hz, 1H), 6.84 (d, J=8.7 Hz, 2H), 4.37 (q, J=7.2 Hz, 2H), 3.05 (s, 6H), 1.36 (t, J=7.2 Hz, 3H).

5-{(E)-[4-(Dimethylamino)phenyl]diazenyl}-1H-indole-2-carboxylic acid (2)

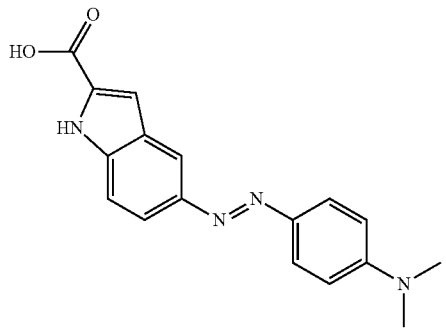 [SMILES: CN(C)c1ccc(/N=N/c2ccc3[nH]c(C(=O)O)cc3c2)cc1]

A suspension of 1 (2.9 g, 8.6 mmol) in a mixture of THF (60 mL), MeOH (40 mL) and 1N NaOH (20 mL) was heated at 50° C. with stirring for 2.5 h to give a clear red-brown solution. The reaction was cooled, neutralized with 20 mL of 1N HCl and concentrated to about 40 mL. The precipitated black solid was collected by filtration, washed with water and dried to afford 2.6 g (98% yield) of acid 2 as a black solid. $^1$H NMR (DMSO-d6) δ 12.06 (s, 1H), 8.13 (d, J=1.5 Hz, 1H), 7.83 (dd, J$_1$=9 Hz, J$_2$=1.8 Hz, 1H), 7.78 (d, J=9 Hz, 2H), 7.52 (d, J=8.7 Hz, 1H), 7.26 (d, J=1.5 Hz, 1H), 6.84 (d, J=8.7 Hz, 2H), 3.05 (s, 6H).

Pentafluorophenyl 5-{(E)-[4-(dimethylamino)phenyl]diazenyl}-1H-indole-2-carboxylate (3)

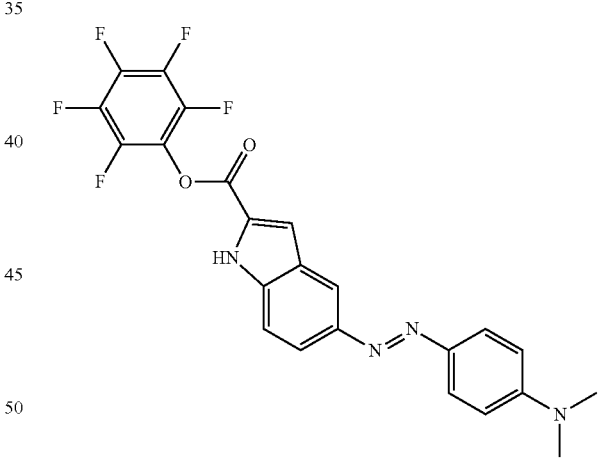

To a suspension of 2 (2.6 g, 8.4 mmol) in 30 mL of anhydrous CH$_2$Cl$_2$ was added triethylamine (4.2 mL) followed by pentafluorophenyl trifluoroacetate (PFP-TFA) in several portions until no more starting acid 2 was observed by TLC or HPLC analysis. Total of 3.5 mL (20.25 mmol) of PFP TFA was added over 16 h. The completed reaction was concentrated and the obtained residue resuspended in cold MeOH (50 mL). The insoluble material was collected by filtration, washed with MeOH (2×10 mL) and dried to afford 2.7 g (68% yield) of 3 as a brown-orange solid. $^1$H NMR (DMSO-d6) δ 12.72 (s, 1H), 8.22 (d, J=1.5 Hz, 1H), 7.93 (dd, J$_1$=8.7 Hz, J$_2$=1.8 Hz, 1H), 7.80 (d, J=9 Hz, 2H), 7.73 (d, J=1.5 Hz, 1H), 7.61 (d, J=9 Hz, 1H), 6.84 (d, J=9 Hz, 2H), s (3.05, 6H).

3,6,7,8-Tetrahydro-6-[[3,6,7,8-tetrahydro-6-[(5-{(E)-[4-(dimethylamino)phenyl]diazenyl}-1H-indol-2-yl)carbonyl]benzo[1,2-b:4,3-b']dipyrrol-2-yl]carbonyl]benzo[1,2-b:4,3-b']dipyrrole-2-carboxylic acid (4)

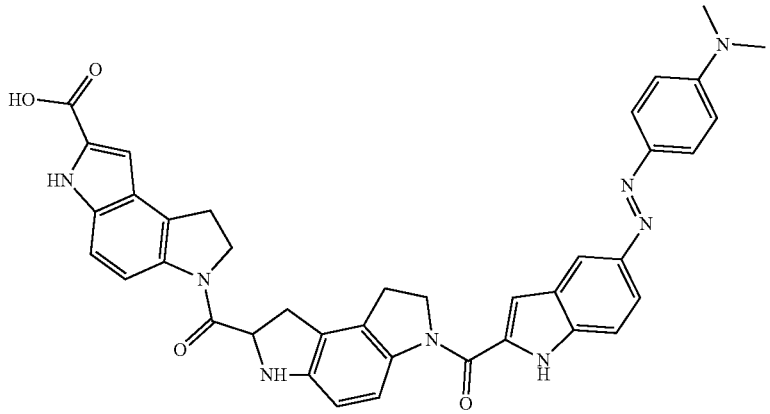 [SMILES: CN(C)c1ccc(/N=N/c2ccc3[nH]c(C(=O)N4CCc5c4ccc4c5CC(C(=O)N5CCc6c5ccc5[nH]c(C(=O)O)cc65)N4)cc3c2)cc1]

To a solution of 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (WO 2004043350) (2.5 mmol) in 10 mL of anhydrous dimethylformamide (DMF) was added triethylamine (1.5 mL) followed by 1.2 g (2.5 mmol) of PFP ester 3. The reaction was briefly stirred to initially give a clear solution but the product precipitation started within minutes. The reaction was agitated for 20 h then the precipitated material was collected by filtration, washed with small amount of DMF (2 mL), MeOH (10 mL) and ether. Drying in vacuo afforded 1.6 g (94% yield) of the title acid 4 (partial triethylammonium salt) as an orange-brown solid. $^1$H NMR (DMSO-d6) δ 12.00 (s, 1H), 11.78 (s, 1H), 11.02 (s, 1H), 8.26 (m, 2H), 8.16 (d, J=1.5 Hz, 1H), 7.81 (dd, J$_1$=8.7 Hz, J$_2$=1.8 Hz, 1H), 7.80 (d, J=9 Hz, 2H), 7.58 (d, 9 Hz, 1H), 7.39 (d, 9 Hz, 1H), 7.32 (m, 2H), 7.12 (d, J=1.5 Hz, 1H), 6.93 (d, J=1.8 Hz, 1H) 6.85 (d, J=9 Hz, 2H), 4.68 (m, 4H), 3.4 (m, 6H), 3.06 (s, 6H), 2.76 (m, 4H), 1.06 (t, J=7.2 Hz, 6H).

Pentafluorophenyl 3,6,7,8-tetrahydro-6-[[3,6,7,8-tetrahydro-6-[(5-{(E)-[4-(dimethylamino)phenyl]diazenyl}-1H-indol-2-yl)carbonyl]benzo[1,2-b:4,3-b']dipyrrol-2-yl]carbonyl]benzo[1,2-b:4,3-b']dipyrrole-2-carboxylate (5)

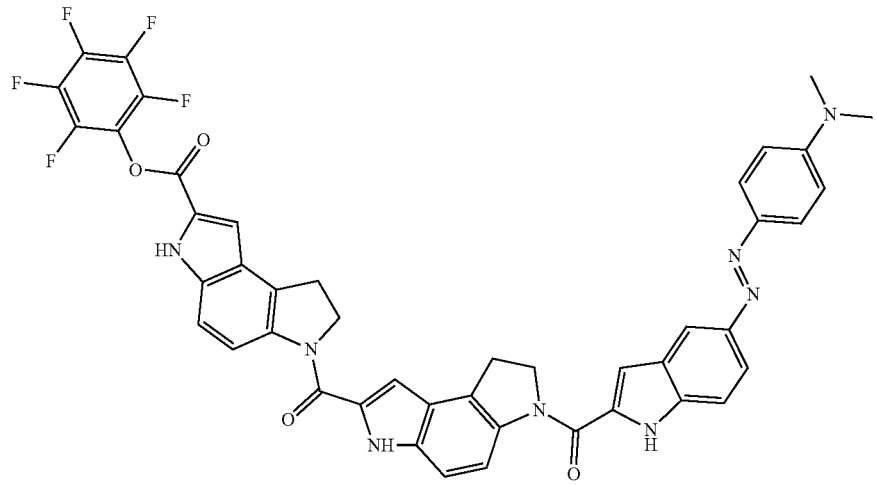 [SMILES: CN(C)c1ccc(/N=N/c2ccc3[nH]c(C(=O)N4CCc5c4ccc4[nH]c(C(=O)N6CCc7c6ccc6[nH]c(C(=O)Oc8c(F)c(F)c(F)c(F)c8F)cc76)cc54)cc3c2)cc1]

To a suspension of 5 (1.5 g, 2.2 mmol) in 10 mL of anhydrous DMF was added 1.2 ml of triethylamine followed by several portions of PFP-TFA over the course of 24 h until no more starting 5 was found by HPLC analysis. A total of 0.9 mL (5.2 mmol) of PFP-TFA was used. MeOH (20 mL) was added to initiate product precipitation. The resultant solid was collected by filtration, washed with methanol (2×10 mL) and ether. Drying in vacuo afforded 1.73 g (93% yield) of PFP ester 5 as a brown solid. NMR analysis indicated a partial (40%) TFA-protection of the indole NH-groups. $^1$H NMR (DMSO-d6) δ 12.64 (s, 0.4H), 12.55 (s, 0.6H), 12.07 (s, 0.4H), 12.00 (s, 0.6H), 11.81 (s, 0.6H), 8.44 (m, 1H), 8.29 (m, 1H), 8.16 (s, 1H), 7.8 (m, 3H), 7.7-7.1 (m, 6H), 6.85 (d, J=9 Hz, 2H), 4.72 (m, 4H), 3.5 (m, 4H), 3.06 (s, 6H).

Ethyl 5-{(E)[2,5-dimethoxy-4-(pyrrolidin-1-yl)phenyl]diazenyl}-1H-indole-2-carboxylate (6)

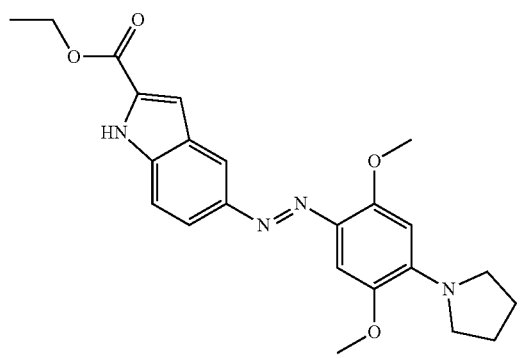 [SMILES: CCOC(=O)c1cc2cc(/N=N/c3cc(OC)c(N4CCCC4)cc3OC)ccc2[nH]1]

To a suspension of ethyl 5-aminoindole-2-carboxylate (3.0 g, 14.7 mmol) in 80 mL of water was added 2.5 mL of conc. HCl. The stirred suspension was cooled in ice/water bath to 0-4° C. and treated with a solution of NaNO$_2$ (1.1 g, 15.9 mmol) in 20 mL of water via an addition funnel over the course of 5 min. The reaction was stirred at 0-4° C. for 20 min then warmed to room temperature and stirred for another 10 min to give a dark, mostly clear solution. 1-(2,5-dimethoxyphenyl)pyrrolidine (M. Sarma et al. J. Org. Chem. 2012, 77(1), 432-444) (4.08 g, 19.7 mmol) was added in one portion and stirring was continued for 10 min before solid sodium acetate trihydrate (5.3 g) was added. The resultant brown suspension was stirred for 2 h. The precipitated solid was collected by filtration, washed with water, MeOH and dried in vacuo to afford 5.3 g (85% yield) of the desired dye 6 as a brown-orange solid. $^1$H NMR (DMSO-d6) δ 12.11 (s, 1H), 8.08 (d, J=1.5 Hz, 1H), 7.78 (dd, J$_1$=9 Hz, J$_2$=1.8 Hz, 1H), 7.50 (d, J=9 Hz, 2H), 7.33 (s, 1H), 7.29 (d, J=1.2 Hz, 1H), 6.30 (s, 1H), 4.37 (q, J=7.2 Hz, 2H), 3.94 (s, 3H), 3.75 (s, 3H), 3.51 (m, 4H), 1.90 (m, 4H), 1.36 (t, J=7.2 Hz, 3H).

5-{(E)[2,5-Dimethoxy-4-(pyrrolidin-1-yl)phenyl]diazenyl}-1H-indole-2-carboxylic acid (7)

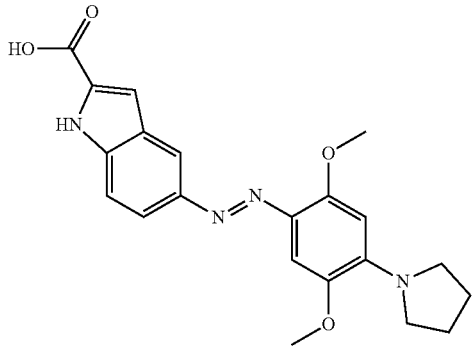 [SMILES: COc1cc(N2CCCC2)c(OC)cc1/N=N/c1ccc2[nH]c(C(=O)O)cc2c1]

To a solution of 6 (5.0 g, 11.8 mmol) in 90 mL of THF was added 60 mL of MeOH and 30 mL of 1N NaOH. The initial suspension was stirred at 50° C. for 1.5 h to give a dark solution. The reaction was cooled, neutralized with 1N HCl (30 mL) and concentrated to about 60 mL. The resultant solid was collected by filtration, washed with water and dried to give 4.5 g (97% yield) of acid 7 as a black solid. $^1$H NMR (DMSO-d6) δ 13.06 (br s, 1H), 12.01 (s, 1H), 8.06 (d, J=1.5 Hz, 1H), 7.76 (dd, J$_1$=9 Hz, J$_2$=1.2 Hz, 1H), 7.49 (d, J=8.7 Hz, 2H), 7.35 (s, 1H), 7.23 (s, 1H), 6.29 (s, 1H), 3.95 (s, 3H), 3.76 (s, 3H), 3.54 (br s, 4H), 1.89 (br s, 4H).

Pentafluorophenyl 5-{(E)-[2,5-dimethoxy-4-(pyrrolidin-1-yl)phenyl]diazenyl}-1H-indole-2-carboxylate (8)

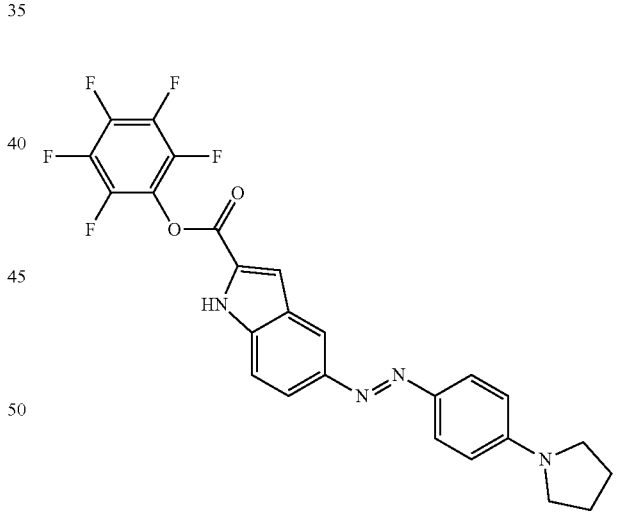

A solution of 7 (1.18 g, 3.0 mmol) and triethylamine (2.2 mL) in 20 mL of anhydrous CH$_2$Cl$_2$ was added PFP-TFA in several portions over the course of 2 days to a total amount of 1.76 mL (10.1 mmol). The reaction (suspension of partially precipitated product) was concentrated and resuspended in 20 mL of MeOH. The insoluble material was collected by filtration, washed with MeOH and dried in vacuo to afford 1.33 g (79% yield) of PFP ester 8 as an orange solid. $^1$H NMR (DMSO-d6) δ 12.67 (s, 1H), 8.16 (d, J=1.5 Hz, 1H), 7.89 (dd, J$_1$=9 Hz, J$_2$=1.8 Hz, 1H), 7.73 (d, J=1.2 Hz, 1H), 7.58 (d, J=9 Hz, 2H), 7.35 (s, 1H), 6.30 (s, 1H), 3.95 (s, 3H), 3.75 (s, 3H), 3.52 (m, 4H), 1.90 (m, 4H).

3,6,7,8-Tetrahydro-6-[[3,6,7,8-tetrahydro-6-[(5-{(E)[2,5-dimethoxy-4-(pyrrolidin-1-yl)phenyl]diazenyl}-1H-indol-2-yl)carbonyl]benzo[1,2-b:4,3-b']dipyrrol-2-yl]carbonyl]benzo[1,2-b:4,3-b']dipyrrole-2-carboxylic acid (9)

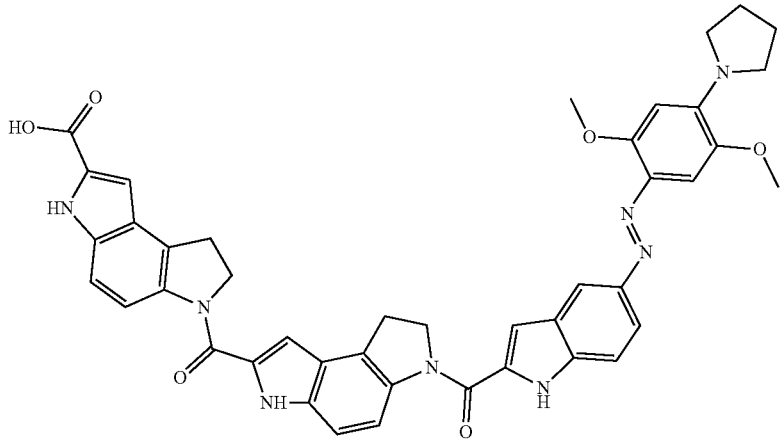 [SMILES: COc1cc(N2CCCC2)c(OC)cc1/N=N/c1ccc2[nH]c(C(=O)N3CCc4c3ccc3[nH]c(C(=O)N5CCc6c5ccc5[nH]c(C(=O)O)cc65)cc43)cc2c1]

To a solution 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (0.8 mmol) in 4 mL of anhydrous DMF was added triethylamine (0.5 mL) followed by 0.45 g (0.8 mmol) of PFP ester 8. The initial suspension was stirred at room temperature for 5 min and then briefly warmed up to approx. 45° C. to give a clear red solution. Product precipitation started soon after that. The reaction was allowed to proceed for 20 h. The precipitated material was collected by filtration, washed with DMF (2×2 ml), acetone (2×10 mL) and dried in vacuo to give 0.56 g (96% yield) of acid 9 (partial triethylammonium salt) as a brown solid. $^1$H NMR (DMSO-d6) δ 11.95 (s, 1H), 11.77 (s, 1H), 11.61 (s, 1H), 8.26 (m, 2H), 8.11 (d, J=1.2 Hz, 1H), 7.76 (dd, $J_1$=9 Hz, $J_2$=1.8 Hz, 1H), 7.55 (d, J=8.7 Hz, 2H), 7.38 (d, 9 Hz, 1H), 7.35 (s, 1H), 7.32 (m, 2H), 7.12 (d, J=1.5 Hz, 1H), 6.92 (s, 1H) 6.32 (s, 1H), 4.68 (m, 4H), 3.95 (s, 3H), 3.76 (s, 3H), 3.5-3.3 (m, 8H), 2.67 (q, J=7.2 Hz, 4H), 1.91 (m, 4H), 1.06 (t, J=7.2 Hz, 6H).

Pentafluorophenyl 3,6,7,8-tetrahydro-6-[[3,6,7,8-tetrahydro-6-[(5-{(E)-[2,5-dimethoxy-4-(pyrrolidin-1-yl)phenyl]diazenyl}-1H-indol-2-yl)carbonyl]benzo[1,2-b:4,3-b']dipyrrol-2-yl]carbonyl]benzo[1,2-b:4,3-b']dipyrrole-2-carboxylate (10)

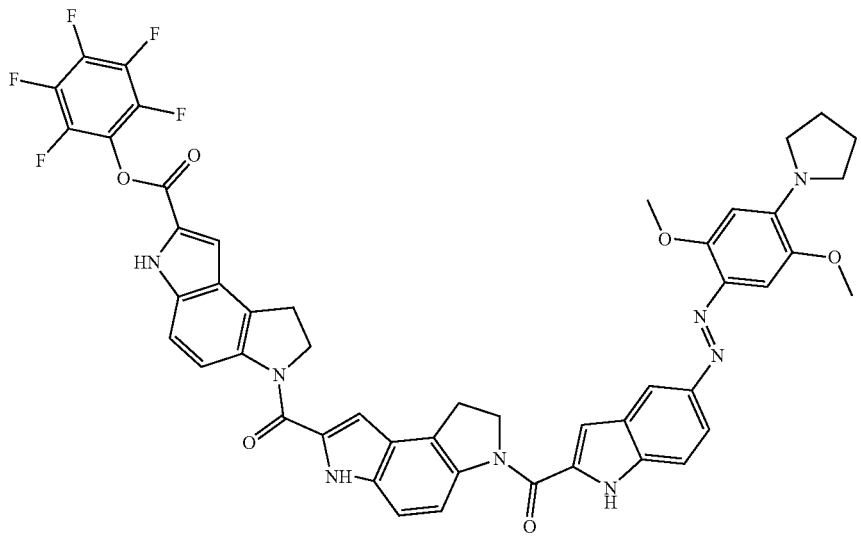 [SMILES: COc1cc(N2CCCC2)c(OC)cc1/N=N/c1ccc2[nH]c(C(=O)N3CCc4c3ccc3[nH]c(C(=O)N5CCc6c5ccc5[nH]c(C(=O)Oc7c(F)c(F)c(F)c(F)c7F)cc65)cc43)cc2c1]

To a suspension of 9 (0.47 g, 0.62 mmol) in 6 mL of anhydrous DMF was added 0.5 mL of triethylamine and 0.2 mL (1.16 mmol) of PFP-TFA. The reaction was stirred for 8 h and treated with another portion of PFP-TFA (0.05 mL) to complete the PFP ester formation. After being stirred for 16 h the precipitated material was collected by filtration, washed with DMF (2×1 mL), acetone (4×5 mL) and dried in vacuo to give 0.43 (75% yield) of PFP ester 10 as an orange solid. $^1$H NMR (DMSO-d6) δ 12.55 (s, 1H), 11.95 (s, 1H), 11.80 (s, 1H), 8.42 (br d, J=9 Hz, 1H), 8.29 (br d, J=8 Hz, 1H), 8.10 (d, J=1.2 Hz, 1H), 7.76 (dd, $J_1$=9 Hz, $J_2$=1.5 Hz, 1H), 7.60 (d, J=1.5 Hz, 1H), 7.55 (d, J=9 Hz, 2H), 7.43 (d, 9 Hz, 1H), 7.39 (d, 9 Hz, 1H), 7.35 (s, 1H), 7.30 (s, 1H), 7.16 (s, 1H) 6.32 (s, 1H), 4.71 (m, 4H), 3.95 (s, 3H), 3.76 (s, 3H), 3.5 (m, 8H), 1.91 (m, 4H).

Ethyl 2-{(E)-[4-(dimethylamino)phenyl]diazenyl}-1,3-benzothiazole-6-carboxylate (11)

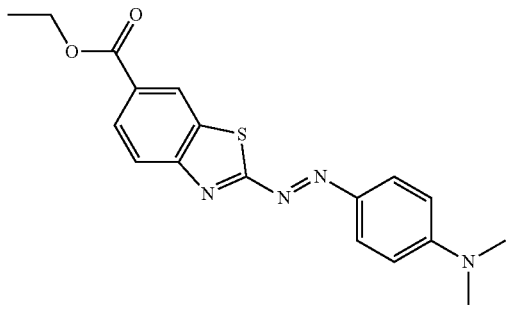 [SMILES: CCOC(=O)c1ccc2nc(/N=N/c3ccc(N(C)C)cc3)sc2c1]

Ethyl 2-amino-1,3-benzothiazole-6-carboxylate (4.44 g, 20 mmol) was resuspended in 100 mL of a 1:1 mixture of acetic and propionic acids. The partial solution was cooled to 0-4° C. and treated with 6.7 mL of 40% nitrosylsulfuric acid maintaining the temperature below 10° C. The reaction was stirred for 5 h then allowed to briefly warm to room temperature before cooling again to 0-4° C. The obtained solution of diazonium salt was added via an addition funnel to a stirred cold (ice/water bath) mixture prepared by combining a solution of N,N-dimethylaniline (3 mL) in 25 mL of MeOH and a solution of 0.6 g of sulfamic acid in 200 mL of water. The stirring was continued for 3 h before the reaction was neutralized by adding approx. 200 mL of 40% aqueous trimethylamine to a pH of 6-7. The resultant solid was collected by filtration, washed with water and resuspended in hot MeOH (50 mL). After cooling the insoluble material was collected by filtration, washed with MeOH (2×10 mL) and dried in vacuo to afford 4.34 g (61% yield) of dye 11 as a dark-purple solid. $^1$H NMR (CDCl$_3$) δ 8.55 (d, J=1.5 Hz, 1H), 8.14 (skewed dd, $J_1$=8.4 Hz, $J_2$=1.5 Hz, 1H), 8.07 (skewed d, J=8.4 Hz, 1H), 8.02 (d, J=9.6 Hz, 2H), 6.78 (d, J=9.6 Hz, 2H), 4.44 (q, J=7.2 Hz, 2H), 3.19 (s, 6H), 1.43 (t, J=7.2 Hz, 3H).

2-{(E)-[4-(Dimethylamino)phenyl]diazenyl}-1,3-benzothiazole-6-carboxylic acid (12)

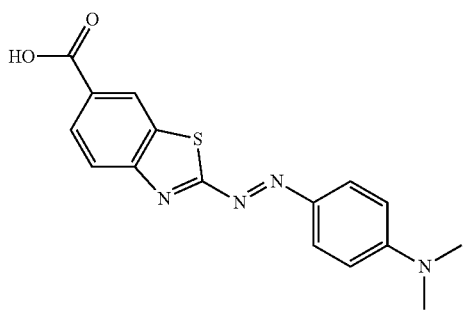 [SMILES: CN(C)c1ccc(/N=N/c2nc3ccc(C(=O)O)cc3s2)cc1]

To a solution of 11 (0.18 g, 0.51 mmol) in 9 mL of THF was added MeOH (6 mL) followed by 3 mL of 1N NaOH. The mixture was stirred at 50° C. for 70 min, cooled, neutralized with 1N HCl (3 mL) and concentrated to about 5 mL. The precipitated material was collected by filtration, washed with water and dried to afford 0.143 g (86% yield) of the desired acid 12 as a black solid. $^1$H NMR (DMSO-d6) δ 13.10 (br s, 1H), 8.60 (s, 1H), 8.02 (s, 2H), 7.87 (d, J=9 Hz, 2H), 6.93 (d, J=9 Hz, 2H), 3.18 (s, 6H).

Pentafluorophenyl 2-{(E)-[4-(dimethylamino)phenyl]diazenyl}-1,3-benzothiazole-6-carboxylate (13)

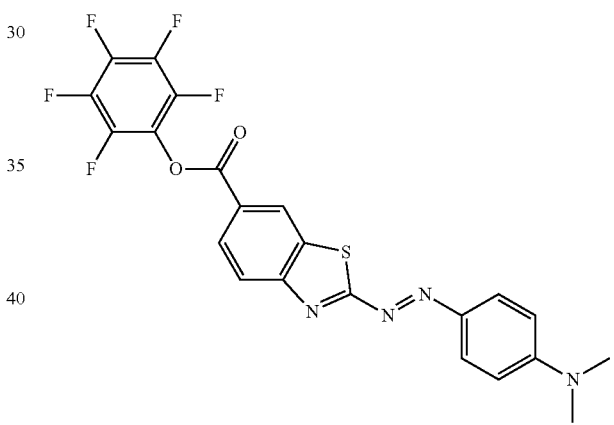

To a solution of 12 (0.14 g, 0.42 mmol) and triethylamine (0.4 mL) in 2 mL of anhydrous DMF was added 0.2 mL (1.16 mmol) of PFP-TFA. After being stirred for 30 min the reaction was concentrated and diluted with acetone (4 mL). The precipitated material was collected by filtration washed with acetone (2 mL), 20% ethyl acetate/hexane (5 mL) and dried in vacuo to give 0.158 g (76% yield) of PFP ester 13 as a dark brown solid. $^1$H NMR (CDCl$_3$) δ 8.72 (d, J=1.5 Hz, 1H), 8.26 (skewed dd, $J_1$=8.4 Hz, $J_2$=1.5 Hz, 1H), 8.16 (skewed d, J=8.4 Hz, 1H), 8.03 (d, J=9.3 Hz, 2H), 6.79 (d, J=9.6 Hz, 2H), 3.21 (s, 6H).

3,6,7,8-Tetrahydro-6-[[3,6,7,8-tetrahydro-6-[(2-{(E)-[4-(dimethylamino)phenyl]diazenyl}-1,3-benzothiazol-6-yl)carbonyl]benzo[1,2-b:4,3-b']dipyrrol-2-yl]carbonyl]benzo[1,2-b:4,3-b']dipyrrole-2-carboxylic acid (14)

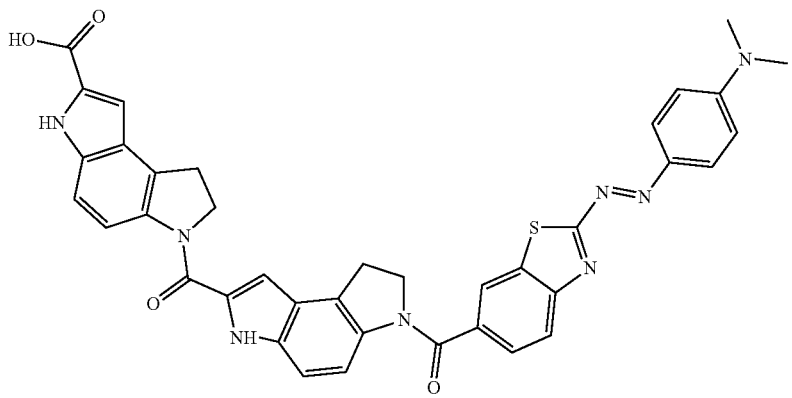 [SMILES: CN(C)c1ccc(/N=N/c2nc3ccc(C(=O)N4CCc5c4ccc4[nH]c(C(=O)N6CCc7c6ccc6[nH]c(C(=O)O)cc76)cc54)cc3s2)cc1]

To a solution of 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (0.33 mmol) in 5 mL of anhydrous DMF was added triethylamine (0.2 mL) followed by 0.156 g (0.32 mmol) of PFP ester 13. The reaction was stirred at 50° C. for 5 h and then cooled to room temperature. The precipitated material was collected by filtration, washed with DMF (2×1 ml), acetone (2×5 mL) and dried in vacuo to give 0.167 g (75% yield) of acid 14 (partial triethylammonium salt) as a brown solid. $^1$H NMR (DMSO-d6) δ 11.75 (s, 1H), 11.66 (s, 1H), 8.30 (s, 1H), 8.1-8.3 (m, 2H), 8.05 (d, J=8.4 Hz, 1H), 7.88 (d, J=9.6 Hz, 2H), 7.72 (d, J=8.1 Hz, 1H), 7.35 (br s, 1H), 7.29 (d, J=9 Hz, 1H), 7.07 (s, 1H), 6.94 (d, J=9 Hz, 2H), 6.93 (s, 1H), 4.62 (t, J=8.7 Hz, 2H), 4.20 (t, J=8.4 Hz, 2H), 3.3 (m, 8H), 3.18 (s, 6H), 2.68 (m, 3H), 1.02 (t, J=7 Hz, 4H).

Pentafluorophenyl 3,6,7,8-tetrahydro-6-[[3,6,7,8-tetrahydro-6-[(2-{(E)-[4-(dimethylamino)phenyl]diazenyl}-1,3-benzothiazol-6-yl)carbonyl]benzo[1,2-b:4,3-b']dipyrrol-2-yl]carbonyl]benzo[1,2-b:4,3-b']dipyrrole-2-carboxylate (15)

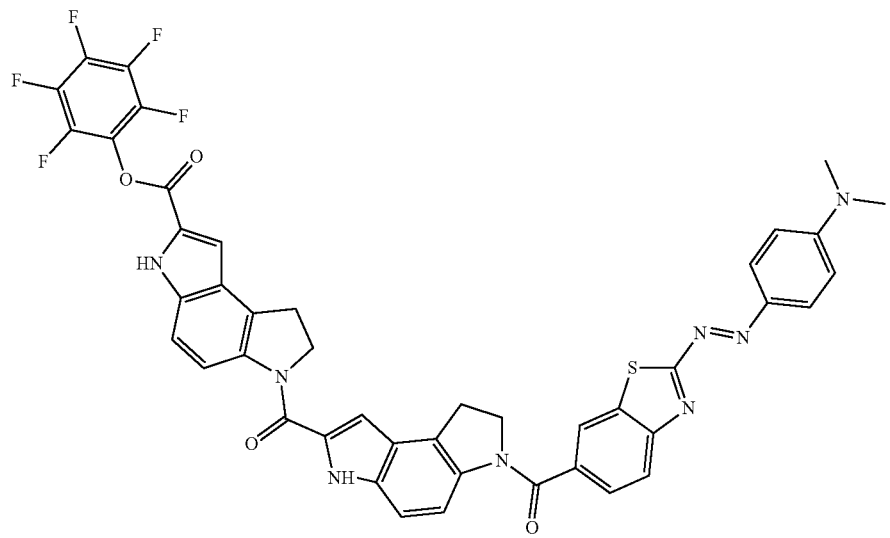 [SMILES: CN(C)c1ccc(/N=N/c2nc3ccc(C(=O)N4CCc5c4ccc4[nH]c(C(=O)N6CCc7c6ccc6[nH]c(C(=O)Oc8c(F)c(F)c(F)c(F)c8F)cc76)cc54)cc3s2)cc1]

To a suspension of 14 (0.163 g, 0.23 mmol) in 2 mL of anhydrous DMF was added 0.1 mL of triethylamine and 0.1 mL (0.58 mmol) of PFP-TFA. After being stirred for 16 h the reaction was concentrated and the resulting material resuspended in acetone (2-3 mL). Filtration, wash with acetone and drying in vacuo afforded 0.175 g (88% yield) of PFP ester 15 as a brown solid. NMR analysis indicated a partial (25%) TFA-protection of the indole NH-groups. $^1$H NMR (DMSO-d6) δ 12.62 (s, 0.25H), 12.52 (s, 0.75H), 11.78 (s, 0.75H), 8.5-8.1 (m, 3H), 8.06 (d, J=8.7 Hz, 0.25H), 8.05 (d, J=8.7 Hz, 0.75H), 7.87 (d, J=9 Hz, 2H), 7.73 (m, 1H), 7.61 (d, J=1.2 Hz, 0.25H), 7.57 (d, J=1.5 Hz, 0.75H), 7.5-7.3 (m, 2H), 7.09 (s, 1H), 6.94 (d, J=9 Hz, 2H), 4.66 (m, 2H), 4.20 (m, 2H), 3.46 (m, 2H), 3.29 (m, 2H), 3.17 (s, 6H).

Ethyl 2-{(E)-[2,5-dimethoxy-4-(pyrrolidin-1-yl)phenyl]diazenyl}-1,3-benzothiazole-6-carboxylate (16)

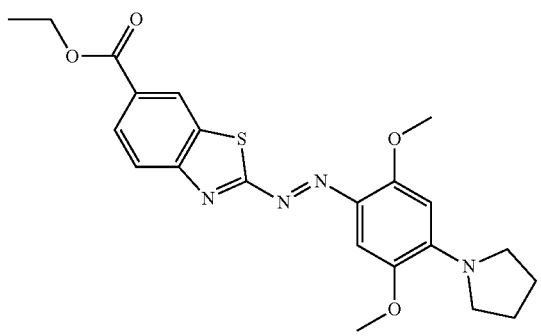 [SMILES: CCOC(=O)c1ccc2nc(/N=N/c3cc(OC)c(N4CCCC4)cc3OC)sc2c1]

To a suspension of ethyl 2-amino-1,3-benzothiazole-6-carboxylate (0.64 g, 2.86 mmol) in acetic acid (8 mL) was added 1 mL of 40% nitrosylsulfuric acid with stirring over a period of 1 min to give a light yellow partial solution. The mixture was stirred at room temperature for 30 min before being used in the next step. A solution of 1-(2,5-dimethoxyphenyl)pyrrolidine (0.88 g, 4.2 mmol) in 20 mL of THF was combined with a solution of sodium acetate trihydrate (2.4 g) in 12 mL of water to give a biphasic mixture. The mixture was cooled to 0-4° C. and treated with the solution of diazonium salt from step 1. The resulting blue suspension was stirred for 1 h and then poured into saturated NaHCO$_3$. The crude dye was extracted with ethyl acetae and purified on silica eluting with a gradient of ethyl acetate in hexane. Concentration of the pure product fractions afforded 0.17 g (13% yield) of dye 16 as a dark purple solid. $^1$H NMR (DMSO-d6) δ 8.54 (d, J=1.8 Hz, 1H), 7.99 (skewed dd, J$_1$=8.7 Hz, J$_2$=1.8 Hz, 1H), 7.89 (skewed d, J=8.4 Hz, 1H), 7.31 (s, 1H), 6.20 (s, 1H), 4.35 (q, J=7.2 Hz, 2H), 4.00 (s, 3H), 3.81 (s, 3H), 3.79 (m, 4H), 1.95 (m, 4H), 1.36 (t, J=7.2 Hz, 3H).

2-{(E)[2,5-Dimethoxy-4-(pyrrolidin-1-yl)phenyl]diazenyl}-1,3-benzothiazole-6-carboxylic acid (17)

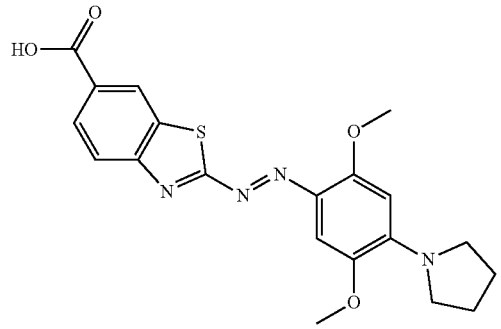 [SMILES: COc1cc(N2CCCC2)c(OC)cc1/N=N/c1nc2ccc(C(=O)O)cc2s1]

To a solution of 11 (0.17 g, 0.39 mmol) in 9 mL of THF was added MeOH (6 mL) followed by 3 mL of 1N NaOH. The mixture was stirred at 50° C. for 70 min, cooled, neutralized with 1N HCl (3 mL) and concentrated to about 5 mL. The precipitated material was collected by filtration, washed with water and dried to afford 0.16 g (99% yield) of the desired acid 17 as a black solid. $^1$H NMR (DMSO-d6) δ 8.51 (d, J=1.5 Hz, 1H), 7.98 (skewed dd, J$_1$=8.4 Hz, J$_2$=1.5 Hz, 1H), 7.82 (skewed d, J=8.4 Hz, 1H), 7.28 (s, 1H), 6.21 (s, 1H), 4.01 (s, 3H), 3.85 (m, 4H), 3.83 (s, 3H), 1.96 (m, 4H).

Pentafluorophenyl 2-{(E)-[2,5-dimethoxy-4-(pyrrolidin-1-yl)phenyl]diazenyl}-1,3-benzothiazole-6-carboxylate (18)

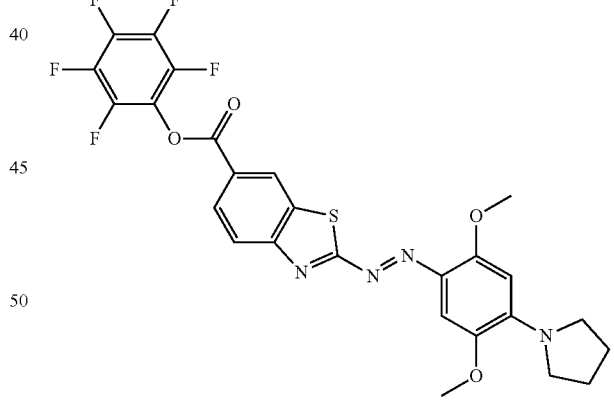

A solution of 17 (0.16 g, 0.39 mmol) and triethylamine (0.4 mL) in 2 mL of anhydrous DMF was treated with several portions (0.05 mL each) of PFP-TFA until no more starting 17 was found by HPLC analysis. A total of 0.35 mL (2 mmol) of PFP-TFA was used. The reaction was concentrated and chromatographed on silica eluting with a gradient of ethyl acetate (50-100%) in hexane. Concentration of the pure product fractions afforded 0.14 g (62% yield) of PFP ester 18 as a black solid. $^1$H NMR (CDCl$_3$) δ 8.51 (m, J=0.9 Hz, 1H), 8.21 (skewed d of m, J$_1$=8.4 Hz, J$_2$=0.9 Hz, 1H), 8.03 (skewed d, J=8.4 Hz, 1H), 7.55 (s, 1H), 6.01 (s, 1H), 4.05 (s, 3H), 3.82 (s, 3H), 3.77 (m, 4H), 2.01 (m, 4H).

3,6,7,8-Tetrahydro-6-[[3,6,7,8-tetrahydro-6-[(2-{(E)
[2,5-dimethoxy-4-(pyrrolidin-1-yl)phenyl]diazenyl}-
1,3-benzothiazol-6-yl)carbonyl]benzo[1,2-b:4,3-b']
dipyrrol-2-yl]carbonyl]benzo[1,2-b:4,3-b']dipyrrole-
2-carboxylic acid (19)

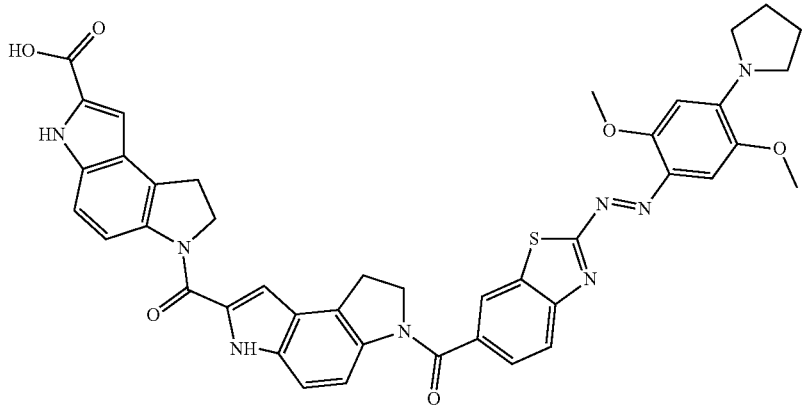 [SMILES: COc1cc(N2CCCC2)c(OC)cc1/N=N/c1nc2ccc(C(=O)N3CCc4c3ccc3[nH]c(C(=O)N5CCc6c5ccc5[nH]c(C(=O)O)cc65)cc43)cc2s1]

To a solution of 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (0.245 mmol) in 5 mL of anhydrous DMF was added triethylamine (0.2 mL) followed by 0.14 g (0.24 mmol) of PFP ester 18. The reaction was stirred at 50° C. for 3 h and then cooled to room temperature. The precipitated material was collected by filtration washed with acetone (3×5 mL) and dried in vacuo to give 0.117 g (62% yield) of acid 19 (partial triethylammonium salt) as a black solid. $^1$H NMR (DMSO-d6) δ 11.78 (s, 1H), 11.71 (s, 1H), 8.4-8.0 (m, 3H), 7.93 (d, J=8.4 Hz, 1H), 7.68 (d, J=8.1 Hz, 1H), 7.33 (s, 1H), 7.4-7.2 (m, 2H), 7.10 (s, 1H), 6.98 (s, 1H), 6.21 (s, 1H), 4.66 (t, J=8.1 Hz, 2H), 4.23 (t, J=8.1 Hz, 2H), 4.00 (s, 3H), 3.82 (s, (3H), 3.78 (m, 4H), 3.45 (m, 2H), 2.71 (m, 2H), 1.96 (m, 4H), 1.04 (t, J=8.4 Hz, 3H).

Pentafluorophenyl 3,6,7,8-tetrahydro-6-[[3,6,7,8-
tetrahydro-6-[(2-{(E)-[2,5-dimethoxy-4-(pyrrolidin-
1-yl)phenyl]diazenyl}-1,3-benzothiazol-6-yl)carbo-
nyl]benzo[1,2-b:4,3-b']dipyrrol-2-yl]carbonyl]benzo
[1,2-b:4,3-b']dipyrrole-2-carboxylate (20)

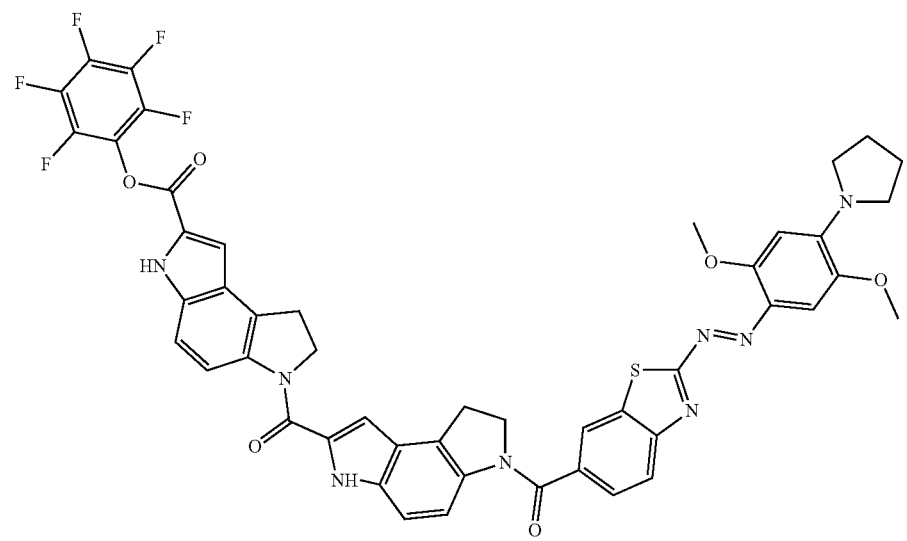 [SMILES: COc1cc(N2CCCC2)c(OC)cc1/N=N/c1nc2ccc(C(=O)N3CCc4c3ccc3[nH]c(C(=O)N5CCc6c5ccc5[nH]c(C(=O)Oc7c(F)c(F)c(F)c(F)c7F)cc65)cc43)cc2s1]

To a suspension of 19 (0.117 g, 0.15 mmol) in 2 mL of anhydrous DMF was added triethylamine (0.1 mL) followed by PFP-TFA (0.1 mL, 0.58 mmol). The reaction was stirred for 1 h and then concentrated. The resultant material was resuspended in acetone (3 mL) and filtered. The collect solid was washed with acetone and dried in vacuo to afford 0.125 g (88% yield) of compound 20 as a dark-purple solid. $^1$H NMR (DMSO-d6) δ 12.57 (s, 1H), 11.82 (s, 1H), 8.44 (d, J=7.8 Hz, 1H), 8.4-8.0 (m, 2H), 7.92 (d, J=8.4 Hz, 1H), 7.8-7.6 (m, 3H), 7.5-7.2 (m, 3H), 7.12 (s, 1H), 6.19 (s, 1H), 4.70 (t, J=8.1 Hz, 2H), 4.23 (t, J=8.1 Hz, 2H), 4.00 (s, 3H), 3.82 (s, (3H), 3.78 (m, 4H), 3.5-3.3 (m, 4H), 1.96 (m, 4H).

Methyl 3-chloro-4-{(E)[2,5-dimethoxy-4-(pyrrolidin-1-yl)phenyl]diazenyl}benzoate (21)

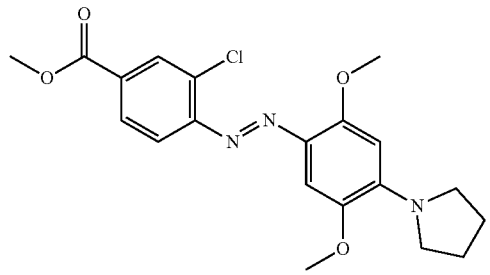 [SMILES: COC(=O)c1ccc(/N=N/c2cc(OC)c(N3CCCC3)cc2OC)c(Cl)c1]

To a suspension of methyl 4-amino-3-chlorobenzoate (1.1 g, 5.9 mmol) in 32 mL of water was added 1 mL of conc. HCl. The stirred suspension was cooled in ice/water bath to 0-4° C. and treated with a solution of NaNO$_2$ (0.44 g, 6.3 mmol) in 8 mL of water via an addition funnel over the course of 5 min. The reaction was stirred at 0-4° C. for 30 min then warmed to room temperature and stirred for another 10 min to give a mostly complete solution. 1-(2,5-dimethoxyphenyl)pyrrolidine (1.9 g, 9.1 mmol) was added in one portion and stirring was continued for 10 min before solid sodium acetate trihydrate (5.0 g) was added. The reaction was allowed to warm to room temperature, stirred for 3 h and then carefully neutralized with saturated NaHCO$_3$. The precipitated solid was collected by filtration, washed with water and dried in vacuo. The crude product was crystallized from hot MeOH to afford 1.8 g (67% yield) of dye 21 as a black crystalline solid. $^1$H NMR (CDCl$_3$) δ 8.14 (d, J=1.8 Hz, 1H), 7.92 (dd, J$_1$=8.7 Hz, J$_2$=1.8 Hz, 1H), 7.71 (d, J=8.7 Hz, 1H), 7.50 (s, 1H), 6.14 (s, 1H), 4.01 (s, 3H), 3.93 (s, 3H), 3.82 (s, 3H), 3.63 (m, 4H), 1.98 (m, 4H).

3-Chloro-4-{(E)[2,5-dimethoxy-4-(pyrrolidin-1-yl)phenyl]diazenyl}benzoic acid (22)

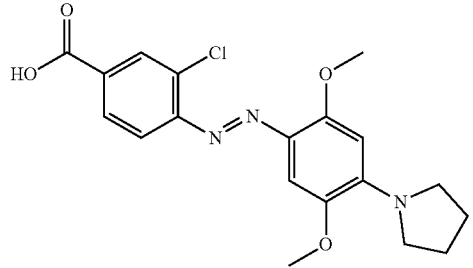 [SMILES: COc1cc(N2CCCC2)c(OC)cc1/N=N/c1ccc(C(=O)O)cc1Cl]

A solution of 21 (1.6 g, 3.96 mmol) in a mixture of THF (90 mL) and MeOH (60 mL) was treated with 1N NaOH (30 mL). The reaction was heated at 50° C. with stirring for 2.5 h to give a clear red solution. The reaction was cooled, neutralized with 30 mL of 1N HCl and concentrated to about 60 mL. The precipitated solid was collected by filtration, washed with water and dried in vacuo to afford 1.7 g (98% yield) of acid 22 as a black solid. $^1$H NMR (DMSO-d6) δ 12.15 (br s, 1H), 8.02 (s, 1H), 7.93 (d, J=7.5 Hz, 1H), 7.65 (d, J=7.8 Hz, 1H), 7.34 (s, 1H), 6.22 (s, 1H), 3.97 (s, 3H), 3.77 (s, 3H), 3.68 (m, 4H), 1.93 (m, 4H).

Pentafluorophenyl 3-chloro-4-{(E)-[2,5-dimethoxy-4-(pyrrolidin-1-yl)phenyl]diazenyl}benzoate (23)

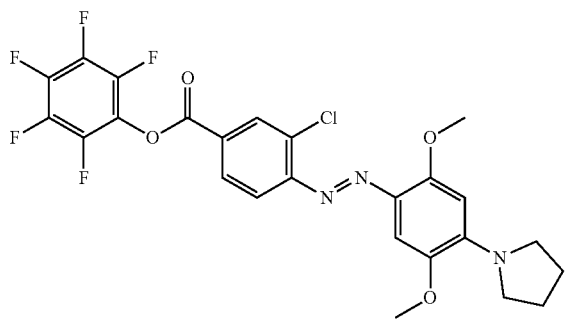 [SMILES: COc1cc(N2CCCC2)c(OC)cc1/N=N/c1ccc(C(=O)Oc2c(F)c(F)c(F)c(F)c2F)cc1Cl]

Acid 22 (1.7 g, 4.3 mmol) was dried by co-evaporation with 25 mL of anhydrous DMF and 1 mL of triethylamine. The dried material was re-dissolved in another portion (25 mL) of DMF with 1 mL of triethylamine and treated with 0.75 mL (4.3 mmol) of PFP-TFA. The reaction was stirred for 60 min to give a thick suspension due to the product precipitation. DMF was removed in vacuo and the resultant solid resuspended in water. The precipitate was collected by filtration, washed with MeOH and dried in vacuo over P$_2$O$_5$. The crude PFP ester 23 was re-crystallized from ethyl acetate to afford 1.94 g (81% yield) of PFP ester 23 as a black crystalline solid. $^1$H NMR (CDCl$_3$) δ 8.29 (d, J=1.8 Hz, 1H), 8.06 (dd, J$_1$=8.7 Hz, J$_2$=1.8 Hz, 1H), 7.82 (d, J=8.7 Hz, 1H), 7.52 (s, 1H), 6.11 (s, 1H), 4.02 (s, 3H), 3.83 (s, 3H), 3.67 (m, 4H), 1.99 (m, 4H).

3,6,7,8-Tetrahydro-6-[[3,6,7,8-tetrahydro-6-[3-chloro-4-{(E)[2,5-dimethoxy-4-(pyrrolidin-1-yl)phenyl]diazenyl}benzoyl]benzo[1,2-b:4,3-b']dipyrrol-2-yl]carbonyl]benzo[1,2-b:4,3-b']dipyrrole-2-carboxylic acid (24)

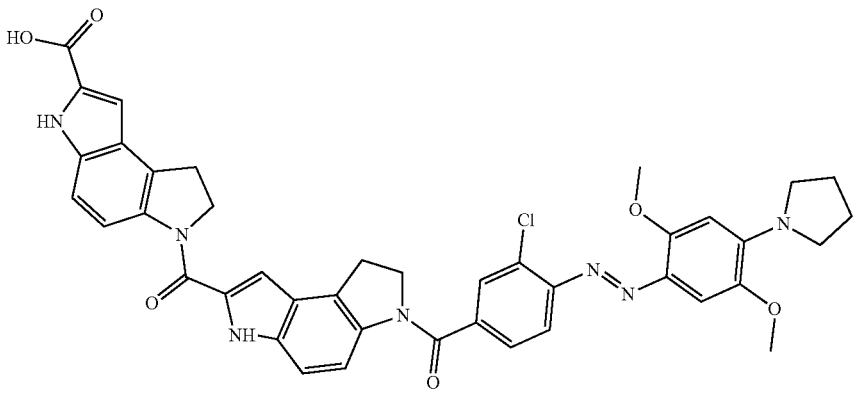 [SMILES: COc1cc(N2CCCC2)c(OC)cc1/N=N/c1ccc(C(=O)N2CCc3c2ccc2[nH]c(C(=O)N4CCc5c4ccc4[nH]c(C(=O)O)cc54)cc32)cc1Cl]

To a solution of 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (0.8 mmol) in 4 mL of anhydrous DMF was added triethylamine (0.5 mL) followed by 0.44 g (0.8 mmol) of PFP ester 23. The reaction was stirred at 50° C. for 5 h and then cooled to room temperature. The precipitated material was collected by filtration, washed with DMF (3×2 ml), acetone (2×5 mL) and dried in vacuo to give 0.46 g (75% yield) of acid 24 (partial triethylammonium salt) as a brown solid. $^1$H NMR (DMSO-d6) δ 11.79 (s, 1H), 11.69 (s, 1H), 8.3-8.1 (m, 2H), 7.84 (s, 1H), 7.66 (apparent br s, 2H), 7.4-7.2 (m, 3H), 7.10 (s, 1H), 6.97 (s, 1H), 6.27 (s, 1H), 4.65 (t, J=7.5 Hz, 2H), 4.22 (t, J=7.8 Hz, 2H), 3.97 (s, 3H), 3.76 (s, 3H), 3.62 (m, 4H), 3.5-3.3 (m, 4H), 2.73 (m, 3H), 1.93 (m, 4H), 1.05 (t, J=7.2 Hz, 4H).

Pentafluorophenyl 3,6,7,8-tetrahydro-6-[[3,6,7,8-tetrahydro-6-[3-chloro-4-{(E)[2,5-dimethoxy-4-(pyrrolidin-1-yl)phenyl]diazenyl}benzoyl]benzo[1,2-b:4,3-b']dipyrrol-2-yl]carbonyl]benzo[1,2-b:4,3-b']dipyrrole-2-carboxylate (25)

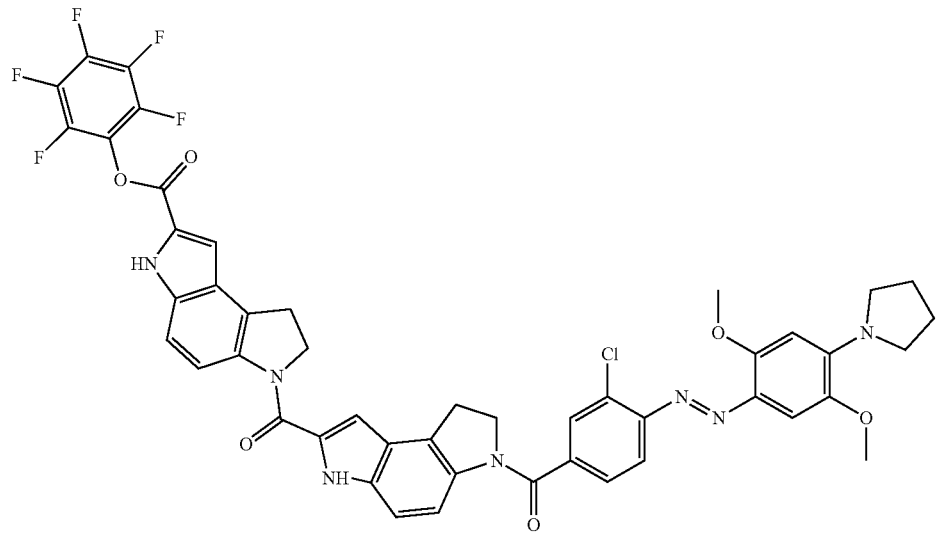 [SMILES: COc1cc(N2CCCC2)c(OC)cc1/N=N/c1ccc(C(=O)N2CCc3c2ccc2[nH]c(C(=O)N4CCc5c4ccc4[nH]c(C(=O)Oc6c(F)c(F)c(F)c(F)c6F)cc54)cc32)cc1Cl]

To a suspension of 24 (0.46 g, 0.61 mmol) in 6 mL of anhydrous DMF was added 0.3 ml of triethylamine followed by several portions of PFP-TFA over the course of 24 h until no more starting 24 was found by HPLC analysis. A total of 0.36 mL (2.1 mmol) of PFP-TFA was used. The reaction was concentrated and the residue resuspended in acetone. The precipitate was collected by filtration, washed with acetone and dried in vacuo to give 0.44 g (78% yield) of PFP ester 25 as a dark brown solid. $^1$H NMR (DMSO-d6) δ 12.56 (s, 1H), 11.82 (s, 1H), 8.44 (d, J=8.4 Hz, 1H), 8.3-8.1 (m, 2H), 7.84 (s, 1H), 7.66 (apparent br s, 2H), 7.6 (s, 1H), 7.4 (m, 3H), 7.12 (s, 1H), 6.22 (s, 1H), 4.69 (t, J=7.5 Hz, 2H), 4.22 (t, J=7.8 Hz, 2H), 3.97 (s, 3H), 3.76 (s, 3H), 3.63 (m, 4H), 3.6-3.3 (m, 4H), 1.93 (m, 4H), 3.49 (t, 2H), 3.30 (m, 2H), 1.93 (m, 4H).

4-[(E)-(4-Amino-2,5-dimethoxyphenyl)diazenyl]benzoic acid (26)

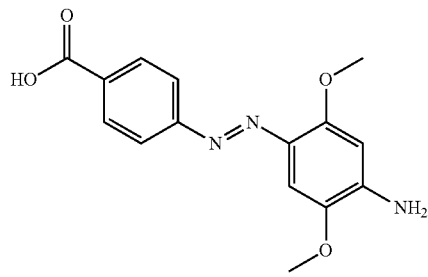 [SMILES: COc1cc(/N=N/c2ccc(C(=O)O)cc2)c(OC)cc1N]

A solution of NaNO$_2$ (2.5 g, 36.5 mmol) in 25 mL of water was added via an addition funnel over the course of 40 min to a cold (0-4° C.) stirred solution of 4-aminobenzoic acid in a mixture of water (200 mL) and conc. HCl (6.2 mL). The resulting light yellow solution was stirred at 0-4° C. for 30 min before being used in the next step. Solid 2,5-dimethoxyaniline (5.59 g, 36.5 mmol) was added in one portion to the stirred solution of diazonium salt from step 1. The reaction was stirred at 0-4° C. for 1.5 h and then at room temperature for 1 h to give a suspension due to the product precipitation. The precipitate was collected by filtration, washed with water and dried. The crude dye was chromatographed on silica eluting with a gradient of MeOH in CH$_2$Cl$_2$ (0-20%). The pure dye fractions were concentrated to afford 3.7 g (33%) of compound 26 as a dark red solid. $^1$H NMR (DMSO-d6) δ 12.9 (br s, 1H), 8.01 (d, J=8.7 Hz, 2H), 7.72 (d, J=8.7 Hz, 2H), 7.25 (s, 1H), 6.41 (s, 1H), 6.24 (s, 2H), 3.83 (s, 3H), 3.76 (s, 3H),

4-[(E)-(2,5-Dimethoxy-4-{(E)-[4-(dimethylamino)phenyl]diazenyl}phenyl)diazenyl]benzoic acid (27)

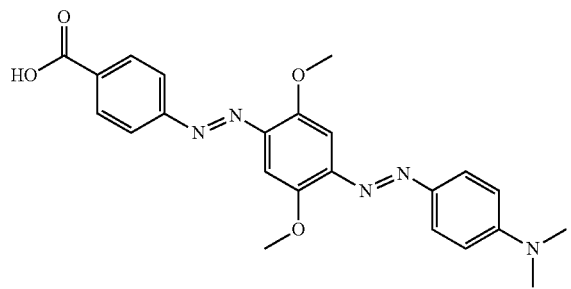 [SMILES: COc1cc(/N=N/c2ccc(N(C)C)cc2)c(OC)cc1/N=N/c1ccc(C(=O)O)cc1]

A solution of NaNO$_2$ (0.85 g, 12.3 mmol) in 8 mL of water was added via an addition funnel over the course of 5 min to a cold (0-4° C.) stirred suspension of compound 26 (3.7 g, 12.3 mmol) in a mixture of water (67 mL) and conc. HCl (2.0 mL). The reaction was stirred at 0-4° C. for 30 min and then at room temperature for 2 h before being used in the next step. A solution of N,N-dimethylaniline (2.4 mL) in 10 mL of MeOH was added in one portion to the diazonium salt from step 1 followed by 5.0 g of sodium acetate trihydrate. The resulting dark suspension was stirred at room temperature for 16 h and then filtered to collect the precipitated solid. The crude dye was purified by trituration in hot MeOH (20 mL) followed by cooling and filtration to yield 2.2 g (41%) of dye 27 as a black solid. $^1$H NMR (DMSO-d6) δ 13.17 (br s, 1H), 8.11 (d, J=8.4 Hz, 2H), 7.93 (d, J=8.7 Hz, 2H), 7.80 (d, J=8.7 Hz, 2H), 7.39 (s, 1H), 7.35 (s, 1H), 6.83 (d, J=9 Hz, 2H), 3.96 (s, 3H), 3.92 (s, 3H), 3.06 (s, 6H).

Pentafluorophenyl 4-[(E)-(2,5-dimethoxy-4-{(E)-[4-(dimethylamino)phenyl]diazenyl}phenyl)diazenyl]benzoate (28)

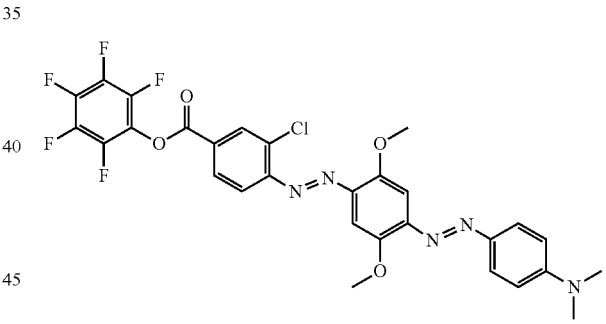

PFP-TFA (1.2 mL, 6.9 mmol) was added in two portions to a solution of 27 (2.2 g, 5.07 mmol) and triethylamine (2 mL) in 50 mL of anhydrous CH$_2$Cl$_2$. After being stirred for 2 h the reaction was concentrated and the obtained semi-solid residue resuspended in 2-propanol (25 mL). The resulting solid was collected by filtration and dried in vacuo to afford crude ester 28, which was then further purified by trituration in hot 4:1 mixture of hexane and ethyl acetate (20 mL) followed by cooling and filtration. Drying in vacuo afforded 2.2 g (72%) of PFP ester 28. $^1$H NMR (CDCl$_3$) δ 8.34 (d, J=8.4 Hz, 2H), 8.05 (d, J=8.7 Hz, 2H), 7.96 (d, J=9 Hz, 2H), 7.53 (s, 1H), 7.49 (s, 1H), 6.77 (d, J=9 Hz, 2H), 4.10 (s, 3H), 4.07 (s, 3H), 3.13 (s, 6H).

3,6,7,8-Tetrahydro-6-[[3,6,7,8-tetrahydro-6-[4-[(E)-(2,5-dimethoxy-4-{(E)-[4-(dimethylamino)phenyl]diazenyl}phenyl)diazenyl]benzoyl]benzo[1,2-b:4,3-b']dipyrrol-2-yl]carbonyl]benzo[1,2-b:4,3-b']dipyrrole-2-carboxylic acid (29)

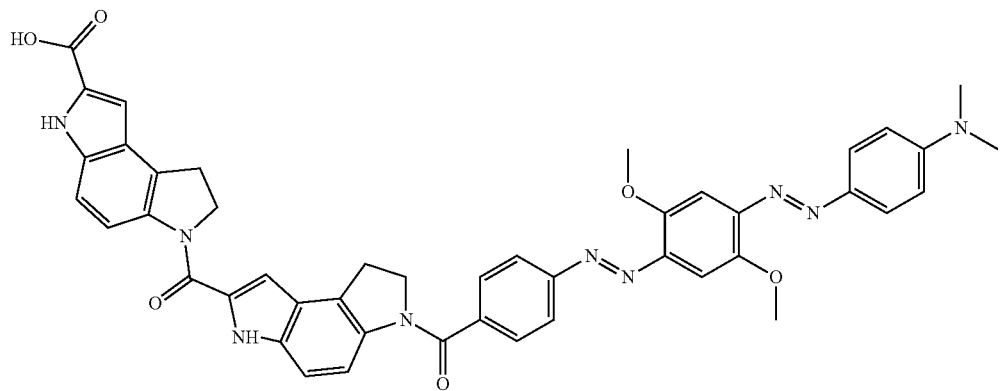 [SMILES: COc1cc(/N=N/c2ccc(N(C)C)cc2)c(OC)cc1/N=N/c1ccc(C(=O)N2CCc3c2ccc2[nH]c(C(=O)N4CCc5c4ccc4[nH]c(C(=O)O)cc54)cc32)cc1]

A mixture of 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (1 mmol), 28 (0.6 g, 1 mmol), DMF (5 mL) and triethylamine was stirred at 50° C. for 20 h and then cooled to room temperature. The resulting precipitate was collected by filtration, washed with DMF (2 mL), CH$_2$Cl$_2$ (2×3 mL) and dried to yield 0.76 g (84%) of compound 29 as a black solid (partial triethylammonium salt according to NMR analysis). $^1$H NMR (DMSO-d6) δ 11.80 (br s, 1H), 11.55 (br s, 1H), 8.22 (m, 2H), 7.98 (m, 2H), 7.85 (m, 3H), 7.46 (s, 1H), 7.42 (s, 1H), 7.30 (d, J=8.7 Hz, 2H), 7.10 (s, 1H), 6.89 (m, 3H), 4.65 (t, J=7.5 Hz, 2H), 4.21 (t, J=7.2 Hz, 2H), 4.02 (s, 3H), 3.99 (s, 3H), 3.39 (m, 4H), 3.11 (s, 6H), 2.76 (m, 6H), 1.08 (t, J=7.2 Hz, 8H).

Pentafluorophenyl 3,6,7,8-tetrahydro-6-[[3,6,7,8-tetrahydro-6-[4-[(E)-(2,5-dimethoxy-4-{(E)-[4-(dimethylamino)phenyl]diazenyl}phenyl)diazenyl]benzoyl]benzo[1,2-b:4,3-b']dipyrrol-2-yl]carbonyl]benzo[1,2-b:4,3-b']dipyrrole-2-carboxylate (30)

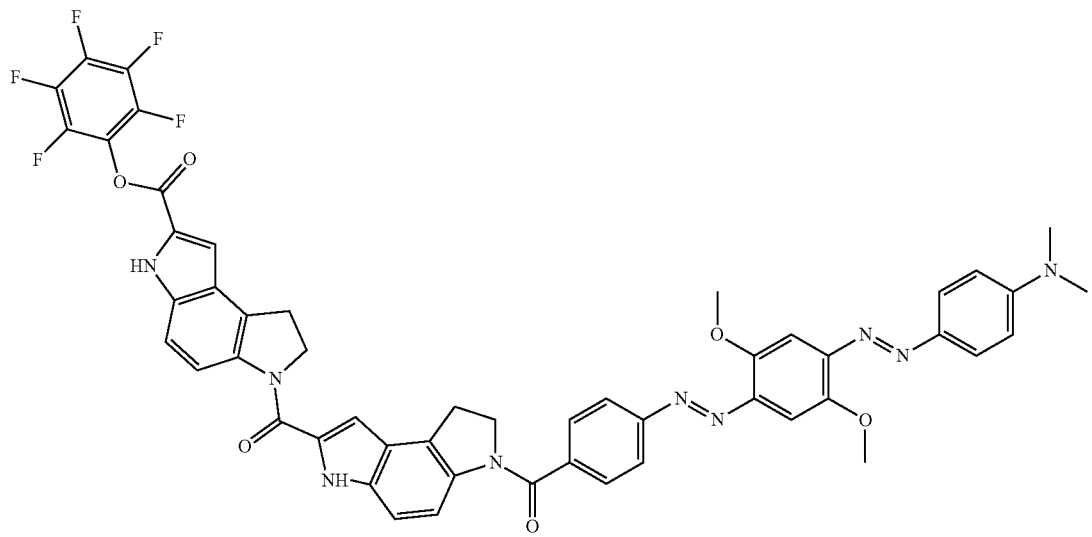 [SMILES: COc1cc(/N=N/c2ccc(N(C)C)cc2)c(OC)cc1/N=N/c1ccc(C(=O)N2CCc3c2ccc2[nH]c(C(=O)N4CCc5c4ccc4[nH]c(C(=O)Oc6c(F)c(F)c(F)c(F)c6F)cc54)cc32)cc1]

To a suspension of 29 (0.76 g, 0.84 mmol) in 10 mL of anhydrous DMF was added 0.5 mL of triethylamine and 0.2 mL (1.16 mmol) of PFP-TFA. The reaction was stirred for 8 h and treated with another portion of PFP-TFA (0.15 mL) to complete the PFP ester formation. After being stirred for 48 h the precipitated material was collected by filtration, washed with DMF (2×0.5 mL), acetone (4×5 mL) and dried in vacuo to give 0.44 (54% yield) of PFP ester 30 as a brown solid. $^1$H NMR (DMSO-d6) δ 12.57 (br s, 1H), 11.84 (br s, 1H), 8.44 (d, J=8.4 Hz, 1H), 8.22 (m, 1H), 8.00 (d, J=8.4 Hz, 2H), 7.86 (m, 4H), 7.62 (s, 1H), 7.45 (m, 4H), 7.16 (s, 1H), 6.89 (d, J=9 Hz, 2H), 4.71 (t, J=7.5 Hz, 2H), 4.23 (t, J=7.2 Hz, 2H), 4.03 (s, 3H), 4.00 (s, 3H), 3.55 (t, J=8.4 Hz, 2H), 3.35 (m, 2H), 3.13 (s, 6H).

Ethyl 5-{(E)-[2-(pyrrolidin-1-yl)-1,3-thiazol-5-yl]diazenyl}-1H-indole-2-carboxylate (31)

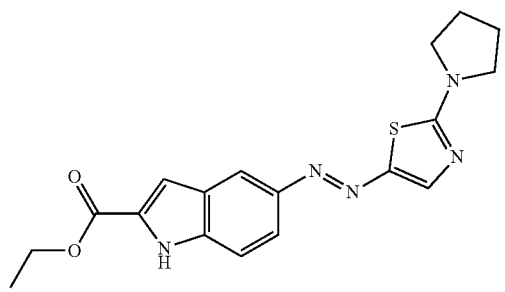 [SMILES: CCOC(=O)c1cc2cc(/N=N/c3cnc(N4CCCC4)s3)ccc2[nH]1]

To a suspension of ethyl 5-aminoindole-2-carboxylate (1.5 g, 7.34 mmol) in 40 mL of water was added 1.25 mL of conc. HCl. The stirred suspension was cooled in ice/water bath to 0-4° C. and treated with a solution of NaNO$_2$ (0.55 g, 8 mmol) in 10 mL of water via an addition funnel over the course of 5 min. The reaction was stirred at 0-4° C. for 20 min then warmed to room temperature and stirred for another 30 min to give a dark, mostly clear solution. 2-(Pyrrolidin-1-yl)-1,3-thiazole (C. Boga et al., Org. Biomol. Chem. 2016, 14, 7061-7068.) (1.5 mL, 9.7 mmol) was added in one portion followed by 2.7 g of sodium acetate trihydrate and 7 mL of MeOH and stirring was continued for 3 h. The precipitated solid was collected by filtration, washed with water and resuspended in 100 mL of MeOH. The suspension was heated to reflux then cooled and filtered to collect the precipitated solid. Drying in vacuo afforded 2.35 g (86%) of the desired dye 31 as an orange solid. $^1$H NMR (DMSO-d6) δ 12.14 (s, 1H), 8.05 (s, 1H), 7.97 (d, J=1.5 Hz, 1H), 7.68 (dd, J$_1$=9 Hz, J$_2$=1.5 Hz, 1H), 7.49 (d, J=9 Hz, 1H), 7.25 (s, 1H), 4.35 (q, J=7.9 Hz, 2H), 3.51 (apparent br s, 4H), 2.00 (m, 4H), 1.34 (t, J=7.2 Hz, 3H).

5-{(E)-[2-(Pyrrolidin-1-yl)-1,3-thiazol-5-yl]diazenyl}-1H-indole-2-carboxylic acid (32)

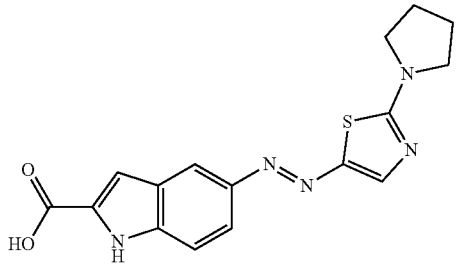 [SMILES: O=C(O)c1cc2cc(/N=N/c3cnc(N4CCCC4)s3)ccc2[nH]1]

A suspension of 31 (2.35 g, 6.3 mmol) in a mixture of THF (135 mL), MeOH (90 mL) and 1N NaOH (45 mL) was heated at 50° C. with stirring for 2.5 h. The reaction was cooled, neutralized with 45 mL of 1N HCl and concentrated to about 80 mL. The precipitated solid was collected by filtration, washed with water and dried to afford 2.17 g (100% yield) of acid 32 as a brown solid. $^1$H NMR (DMSO-d6) δ 13.08 (br s, 1H), 12.03 (s, 1H), 8.06 (s, 1H), 7.97 (d, J=1.8 Hz, 1H), 7.68 (dd, J$_1$=9 Hz, J$_2$=1.8 Hz, 1H), 7.47 (d, J=9 Hz, 1H), 7.20 (d, J=1.2 Hz, 1H), 3.52 (apparent br s, 4H), 2.01 (m, 4H).

Pentafluorophenyl 5-{(E)-[2-(pyrrolidin-1-yl)-1,3-thiazol-5-yl]diazenyl}-1H-indole-2-carboxylate (33)

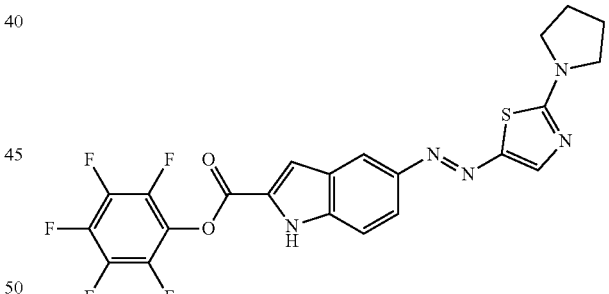

To a solution of 32 (1.0 g, 2.92 mmol) and thriethylamine (2 mL) in 30 mL of anhydrous CH$_2$Cl$_2$ was added PFP-TFA in several 0.5 mL portions over the course of 2 days until no more starting material was found by HPLC analysis. A total of 1.5 mL (8.7 mmol) of PFP-TFA was added. The precipitated product was collected by filtration, washed with small amount (approx. 2 mL) of CH$_2$Cl$_2$, 4:1 hexane-ethyl acetate and hexane. Drying in vacuo afforded 0.865 g (58%) of PFP ester 33 as a yellow solid. $^1$H NMR (DMSO-d6) δ 12.71 (d, J=1.2 Hz, 1H), 8.11 (s, 1H), 8.07 (d, J=1.8 Hz, 1H), 7.80 (dd, J$_1$=9 Hz, J$_2$=1.8 Hz, 1H), 7.71 (d, J=1.5 Hz, 1H), 7.58 (d, J=9 Hz, 1H), 3.54 (apparent br s, 4H), 2.03 (m, 4H).

3,6,7,8-Tetrahydro-6-[(5-{(E)-[2-(pyrrolidin-1-yl)-1,3-thiazol-5-yl]diazenyl}-1H-indol-2-yl)carbonyl]benzo[1,2-b:4,3-b']dipyrrole-2-carboxylic acid (34)

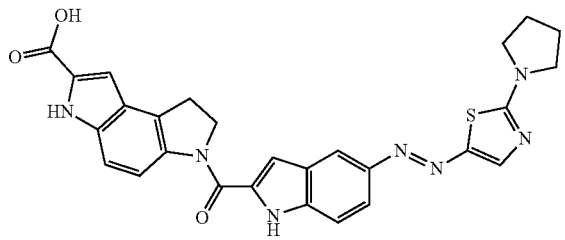 [SMILES: O=C(O)c1cc2c3c(ccc2[nH]1)N(C(=O)c1cc2cc(/N=N/c4cnc(N5CCCC5)s4)ccc2[nH]1)CC3]

To a solution of 3,6,7,8-tetrahydro-benzo[1,2-b:4,3-b']dipyrrole-2-carboxylic acid, (0.79 mmol) and 0.5 mL of triethylamine in 5 mL of DMF was added 0.4 g (0.79 mmol) of PFP ester 33 and the reaction was stirred for 18 h. Precipitated material was collected by filtration, washed with MeOH (2×5 ml) and dried in vacuo to give 0.414 g (99%) of compound 34 (partial triethylammonium salt) as a yellow solid. $^1$H NMR (DMSO-d6) δ 11.98 (s, 1H), 11.73 (s, 1H), 8.26 (d, J=8.1 Hz, 1H), 8.06 (s, 1H), 7.99 (d, J=1.5 Hz, 1H), 7.68 (dd, $J_1$=9 Hz, $J_2$=1.8 Hz, 1H), 7.53 (d, J=9 Hz, 1H), 7.32 (d, J=9 Hz, 1H), 7.26 (s, 1H), 7.00 (s, 1H), 4.65 (t, J=8.1 Hz, 2H), 3.54 (apparent br s, 4H), 3.43 (t, J=8.1 Hz, 2H), 2.79 (q, J=7.2 Hz, 2H), 2.03 (m, 4H), 1.08 (t, J=7.2 Hz, 3H).

Pentafluorophenyl 3,6,7,8-tetrahydro-6-[(5-{(E)-[2-(pyrrolidin-1-yl)-1,3-thiazol-5-yl]diazenyl}-1H-indol-2-yl)carbonyl]benzo[1,2-b:4,3-b']dipyrrole-2-carboxylate (35)

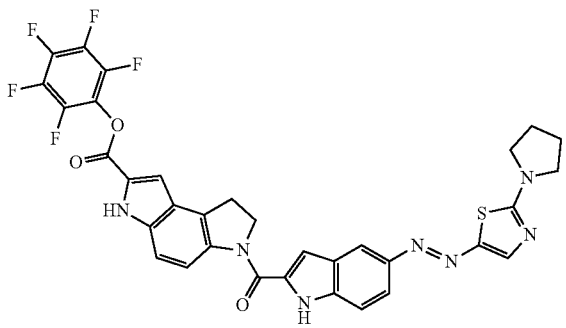 [SMILES: O=C(Oc1c(F)c(F)c(F)c(F)c1F)c1cc2c3c(ccc2[nH]1)N(C(=O)c1cc2cc(/N=N/c4cnc(N5CCCC5)s4)ccc2[nH]1)CC3]

To a suspension of 34 (0.40 g, 0.76 mmol) in 9 mL of anhydrous DMF was added 0.5 mL of triethylamine and 0.2 mL (1.16 mmol) of PFP-TFA. The reaction was stirred for 1 h and treated with another portion of PFP-TFA (0.2 mL) to complete the PFP ester formation. After being stirred for 2 h the reaction was concentrated and the precipitated material was collected by filtration. The solid was resuspended in 2-propanol (5 mL), washed with more 2-propanol (2×5 mL) and dried to yield 0.57 g (100%) of PFP ester 35. According to NMR analysis the product was partially (approx. 40%) TFA-blocked at one of the indole NH-groups. $^1$H NMR (DMSO-d6) δ 12.64 (s, 0.4H), 12.55 (s, 0.6H), 12.00 (s, 1H), 8.5-7.2 (aromatic protons, 8H), 4.69 (m, 2H), 3.52 (m, 6H), 2.03 (m, 4H).

3,6,7,8-Tetrahydro-6-[[3,6,7,8-tetrahydro-6-[(5-{(E)-[2-(pyrrolidin-1-yl)-1,3-thiazol-5-yl]diazenyl}-1H-indol-2-yl)carbonyl]benzo[1,2-b:4,3-b']dipyrrol-2-yl]carbonyl]benzo[1,2-b:4,3-b']dipyrrole-2-carboxylic acid (36)

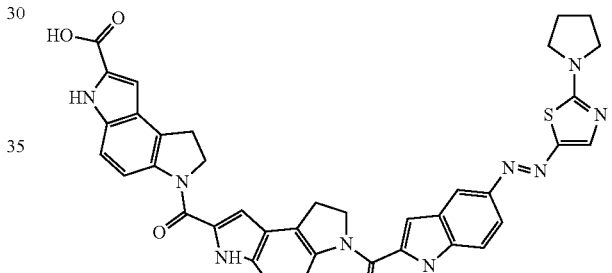

To a solution of 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (0.79 mmol) in 5 mL of anhydrous DMF was added 0.5 mL of triethylamine followed by 0.4 g (0.79 mmol) of PFP ester 33. The mixture was briefly stirred to initially give a clear solution which quickly turned into a suspension due to the product precipitation. The reaction was swirled for 18 h and the precipitated material collected by filtration. The collected solid was washed with MeOH (3×5 mL), CH$_2$Cl$_2$ (10 mL) and dried in vacuo to afford 0.59 g (100%, as triethylammonium salt) of compound 36 as an orange solid. $^1$H NMR (DMSO-d6) δ 12.00 (s, 1H), 11.78 (d, J=1.2 Hz, 1H), 11.63 (s, 1H), 8.27 (m, 2H), 8.07 (s, 1H), 7.99 (d, J=1.5 Hz, 1H), 7.69 (dd, $J_1$=9 Hz, $J_2$=1.5 Hz, 1H), 7.54 (d, J=9 Hz, 1H), 77.39 (d, J=9 Hz, 1H), 7.31 (d, J=9 Hz, 1H), 7.27 (s, 1H), 7.13 (s, 1H), 6.94 (s, 1H), 4.67 (m, 4H), 3.53 (m, 4H), 3.42 (m, 4H), 2.72 (q, J=7.2 Hz, 4H), 2.03 (m, 4H), 1.05 (t, J=7.2 Hz, 6H).

Pentafluorophenyl 3,6,7,8-tetrahydro-6-[[3,6,7,8-tetrahydro-6-[(5-{(E)-[2-(pyrrolidin-1-yl)-1,3-thiazol-5-yl]diazenyl}-1H-indol-2-yl)carbonyl]benzo[1,2-b:4,3-b']dipyrrol-2-yl]carbonyl]benzo[1,2-b:4,3-b']dipyrrole-2-carboxylate (37)

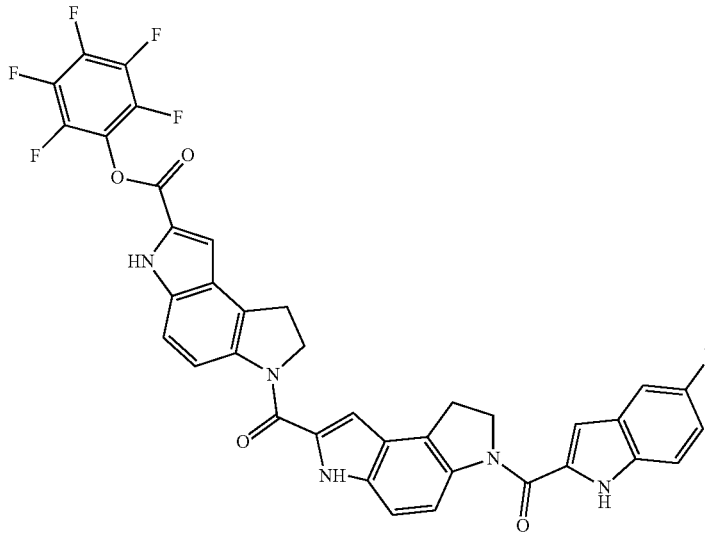

To a suspension of 36 (0.58 g, 0.8 mmol) in DMF (9 mL) was added triethylamine (0.5 mL) followed by PFP-TFA (0.2 mL). The suspension was stirred for 2 h and treated with another 0.2 mL portion of PFP-TFA and stirring was continued for 3 more days. The precipitated material was collected by filtration, washed with 2-propanol (2×5 mL) and dried in vacuo to afford 0.40 g (57%) of PFP ester 37 as a yellow solid. $^1$H NMR (DMSO-d6) δ 12.56 (s, 1H), 11.99 (s, 1H), 11.82 (s, 1H), 8.42 (br d, J=8.7 Hz, 1H), 8.29 (br d, J=7.5 Hz, 1H), 8.07 (s, 1H), 8.00 (d, J=1.5 Hz, 1H), 7.68 (dd, $J_1$=9 Hz, $J_2$=1.8 Hz, 1H), 7.61 (d, J=1.2 Hz, 1H), 7.54 (d, J=9 Hz, 1H), 7.44 (d, J=9 Hz, 1H), 7.39 (d, J=9 Hz, 1H), 7.27 (s, 1H), 7.17 (s, 1H), 4.69 (m, 4H), 3.53 (m, 8H), 2.03 (m, 4H).

4-{(E)-[2,5-Dimethoxy-4-(pyrrolidin-1-yl)phenyl]diazenyl}-1-methyl-1H-pyrrole-2-carboxylic acid (38)

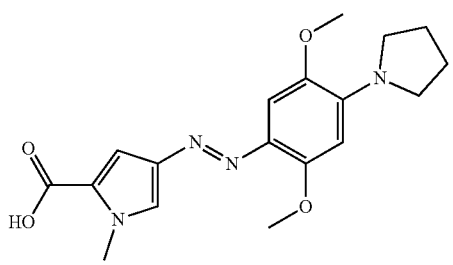 [SMILES: COc1cc(N2CCCC2)c(OC)cc1/N=N/c1cc(C(=O)O)n(C)c1]

4-[[(1,1-dimethylethoxy)carbonyl]amino]-1-methyl-1H-pyrrole-2-carboxylic acid 90.49 g (2.04 mmol) was treated with 11 mL of conc. HCl for 30 min. The resultant solution was cooled to 0-4° C. and while being stirred treated with a solution of sodium nitrite (0.15 g) in 3 mL of water maintaining the temperature below 5° C. The cold reaction was stirred at 0-4° C. for 2 h before being used in the next step. A solution of 1-(2,5-dimethoxyphenyl)pyrrolidine (0.66 g, 3.2 mmol) in 50 mL of MeOH was added with stirring to the solution of diazonium salt from step 1 followed by 100 mL of 1 NaOH and the reaction was allowed to warm to room temperature. After being stirred for 10 h the reaction was concentrated to approx. 100 mL and the resultant solid collected by filtration. The solid was washed with water and dried in vacuo to afford 0.275 g (37%) of dye 38 as a black solid. $^1$H NMR (DMSO-d6) δ 7.65 (s, 1H), 7.29 (s, 1H), 6.99 (d, J=1.8 Hz, 1H), 6.29 (s, 1H), 3.91 (s, 6H), 3.74 (s, 3H), 3.36 (apparent br s, 4H), 1.90 (m, 4H).

Pentafluorophenyl 4-{(E)-[2,5-dimethoxy-4-(pyrrolidin-1-yl)phenyl]diazenyl}-1-methyl-1H-pyrrole-2-carboxylate (39)

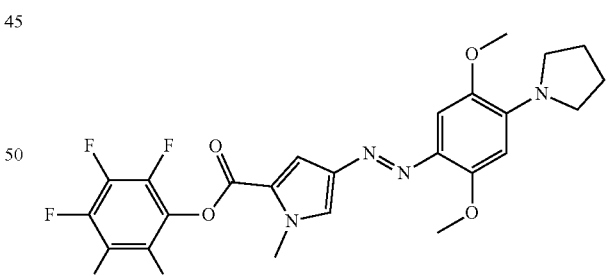

To a solution of 38 (0.27 g, 0.75 mmol) and thriethylamine (0.5 mL) in 7.5 mL of anhydrous CH$_2$Cl$_2$ was added PFP-TFA in several 0.1 mL portions over the course of 2 days until no more starting material was found by HPLC analysis. A total of 0.3 mL (1.7 mmol) of PFP-TFA was added. The reaction was concentrated and the residue triturated with 2-propanol (5 mL). The sold material was collected by filtration, washed with small amount (approx. 2 mL) of MeOH and dried to afford 0.17 g (43%) of PFP ester 39 as a brown orange solid. $^1$H NMR (DMSO-d6) δ 7.99 (d, J=1.5 Hz, 1H), 7.40 (d, J=1.8 Hz, 1H), 7.21 (s, 1H), 6.26 (s, 1H), 3.96 (s, 3H), 3.89 (s, 3H), 3.71 (s, 3H), 3.49 (m, 4H), 1.88 (m, 4H).

3,6,7,8-Tetrahydro-6-[[3,6,7,8-tetrahydro-6[(4-{(E)-[2,5-dimethoxy-4-(pyrrolidin-1-yl)phenyl]diazenyl}-1-methyl-1H-pyrrol-2-yl)carbonyl]benzo[1,2-b:4,3-b']dipyrrol-2-yl]carbonyl]benzo[1,2-b:4,3-b']dipyrrole-2-carboxylic acid (40)

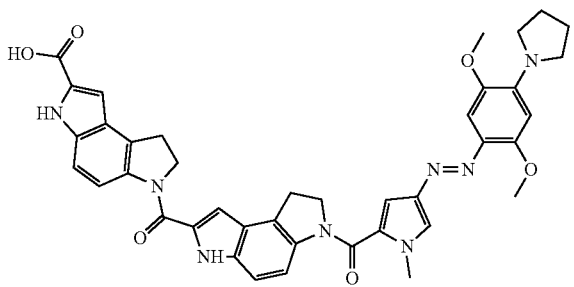 [SMILES: COc1cc(N2CCCC2)c(OC)cc1/N=N/c1cc(C(=O)N2CCc3c2ccc2[nH]c(C(=O)N4CCc5c4ccc4[nH]c(C(=O)O)cc54)cc32)n(C)c1]

To a solution of 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (0.33 mmol) in 2 mL of anhydrous DMF was added 0.3 mL of triethylamine followed by 0.17 g (0.32 mmol) of PFP ester 39. The reaction was stirred at 50° C. for 24 h and then concentrated. The obtained dark residue was triturated with ethyl acetate (10 mL), the precipitated material was collected by filtration, washed with MeOH (2×5 mL) and dried to afford 0.203 g (84%) of compound 40 as a dark brown solid. $^1$H NMR (DMSO-d6) δ 13.00 (br s, 1H), 11.84 (s, 1H), 11.76 (s, 1H), 8.28 (br d, J=7.5 Hz, 1H), 7.98 (br s, 1H), 7.64 (s, 1H), 7.34 (d, J=9H, 2H), 7.20 (s, 1H), 7.09 (s, 1H), 7.05 (s, 1H), 6.88 (s, 1H), 6.28 (s, 1H), 4.65 (t, J=8.1 Hz, 2H), 4.44 (t, J=8.1 Hz, 2H), 3.88 (s, 3H), 3.83 (s, 3H), 3.71 (s, 3H), 3.5-3.4 (m, 8H), 1.88 (m, 4H).

Pentafluorophenyl 3,6,7,8-tetrahydro-6-[[3,6,7,8-tetrahydro-6-[(4-{(E)-[2,5-dimethoxy-4-(pyrrolidin-1-yl)phenyl]diazenyl}-1-methyl-1H-pyrrol-2-yl)carbonyl]benzo[1,2-b:4,3-b']dipyrrol-2-yl]carbonyl]benzo[1,2-b:4,3-b']dipyrrole-2-carboxylate (41)

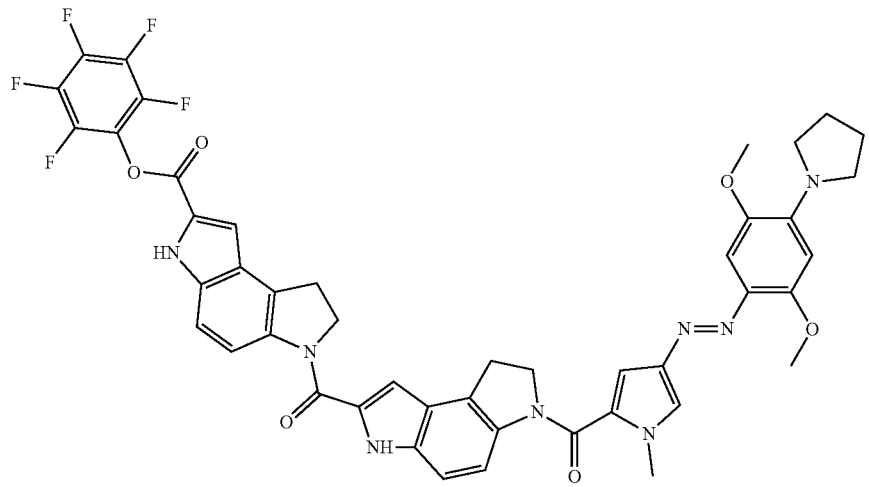 [SMILES: COc1cc(N2CCCC2)c(OC)cc1/N=N/c1cc(C(=O)N2CCc3c2ccc2[nH]c(C(=O)N4CCc5c4ccc4[nH]c(C(=O)Oc6c(F)c(F)c(F)c(F)c6F)cc54)cc32)n(C)c1]

To a suspension of 40 (0.197 g, 0.27 mmol) in DMF (3 mL) was added triethylamine (0.2 mL) followed by PFP-TFA (0.1 mL). The suspension was stirred for 20 h and treated with another 0.05 mL portion of PFP-TFA and stirring was continued for 1 more hour. DMF was removed and the residue triturated with 2-propanol (5 mL). The resultant material was collected by filtration, washed with 2-propanol (2×5 mL) and dried in vacuo to afford 0.218 g (90%) of PFP ester 41 as a brown solid. $^1$H NMR (DMSO-d6) δ 12.54 (s, 1H), 11.78 (s, 1H), 8.40 (br d, J=7.8 Hz, 1H), 7.99 (br s, 1H), 7.64 (s, 1H), 7.59 (s, 1H), 7.42 (d, J=9 Hz, 1H), 7.32 (d, J=9 Hz, 1H), 7.20 (s, 1H), 7.11 (s, 1H), 6.88 (s, 1H), 6.28 (s, 1H), 4.66 (t, J=8.1 Hz, 2H), 4.44 (t, J=8.1 Hz, 2H), 3.88 (s, 3H), 3.83 (s, 3H), 3.71 (s, 3H), 3.5-3.4 (m, 8H), 1.88 (m, 4H).

Ethyl 2-[(E)-2,3,6,7-tetrahydro-1H,5H-pyrido[3,2,1-ij]quinolin-9-yldiazenyl]-1,3-benzothiazole-6-carboxylate (42)

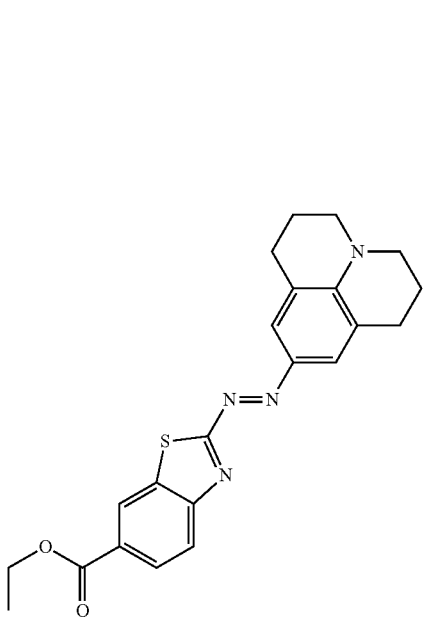 [SMILES: CCOC(=O)c1ccc2nc(/N=N/c3cc4c5c(c3)CCCN5CCC4)sc2c1]

A solution of ethyl 2-amino-1,3-benzothiazole-6-carboxylate (2.22 g, 10 mmol) in a 1:1 mixture of acetic and propionic acids (50 mL) was cooled to 0-4° C. and then treated with 3.1 mL of 40% nitrosylsulfuric acid over the course of 5 min. The resulting suspension was stirred at 0-4° C. for 5 min and then at room temperature for another 5 min to give a clear solution and then cooled back to 0-4° C. before being used in the next step. A solution of julolidine (2.1 g, 12 mmol) in MeOH (15 mL) was combined with a solution of sulfamic acid (0.3 g) in water (100 mL) and then cooled to 0-4° C. To this mixture was added the previously prepared diazonium salt over the course of 5 min. The reaction was stirred for 1 h and then diluted with water (400 mL) and neutralized with 90 mL of thiethylamine. The precipitated solid was extracted with ethyl acetate, washed with saturated NaHCO$_3$, dried over Na$_2$SO$_4$ and concentrated under reduced pressure. The obtained residue was triturated with warm 1:1 hexane-ethyl acetate (30 mL) and the resultant solid collected by filtration. Drying under reduced pressure afforded 0.8 g (48%) of sufficiently pure dye 42 as a dark purple solid. $^1$H NMR (CDCl$_3$) δ 8.51 (d, J=1.5 Hz, 1H), 8.11 (skewed dd, J$_1$=8.7 Hz, J$_2$=1.5 Hz, 1H), 8.01 (skewed d, J=8.7 Hz, 1H), 7.61 (s, 2H), 4.42 (q, J=7.2 Hz, 2H), 3.39 (t, J=6 Hz, 4H), 2.80 (t, J=6 Hz, 4H), 2.00 (m, 4H), 1.43 (t, J=7.2 Hz, 3H).

2-[(E)-2,3,6,7-Tetrahydro-1H,5H-pyrido[3,2,1-ij]quinolin-9-yldiazenyl]-1,3-benzothiazole-6-carboxylic acid (43)

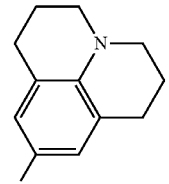

To a solution of 42 (0.35 g, 0.86 mmol) in a mixture of THF (18 mL) and MeOH (12 mL) was added 6 mL of 1N NaOH. The reaction was stirred at 50° C. for 1.5 h then cooled, neutralized with 1N HCl (6 mL) and concentrated under reduced pressure to about 10 mL. The resulting precipitate was collected by filtration, washed with water and dried to afford 0.32 g (98%) of compound 43 as a black solid. $^1$H NMR (DMSO-d6) δ 13.0 (br s, 1H), 8.54 (d, J=1.5 Hz, 1H), 7.99 (skewed dd, J$_1$=8.7 Hz, J$_2$=1.5 Hz, 1H), 7.93 (skewed d, J=8.7 Hz, 1H), 7.47 (s, 2H), 3.43 (t, J=6 Hz, 4H), 2.77 (t, J=6 Hz, 4H), 1.90 (m, 4H).

Pentafluorophenyl 2-[(E)-2,3,6,7-tetrahydro-1H,5H-pyrido[3,2,1-ij]quinolin-9-yldiazenyl]-1,3-benzothiazole-6-carboxylate (44)

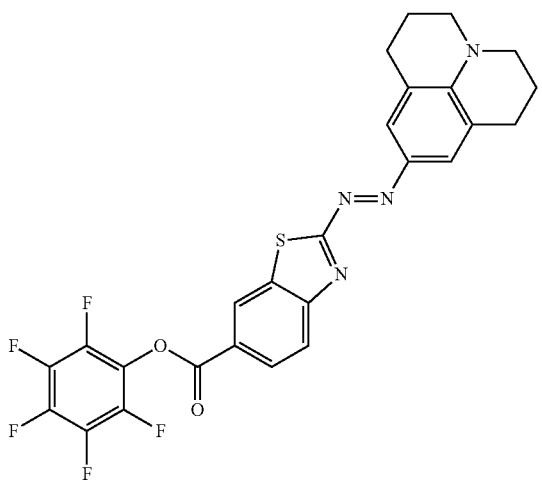 [SMILES: O=C(Oc1c(F)c(F)c(F)c(F)c1F)c1ccc2nc(/N=N/c3cc4c5c(c3)CCCN5CCC4)sc2c1]

To a solution of 43 (0.32 g, 0.84 mmol) and triethylamine (0.5 mL) in 10 mL of anhydrous DMF was added PFP-TFA in several portions over the course of 3 hours until no more starting material was found by HPLC analysis. A total of 0.5 mL (2.9 mmol) of PFP-TFA was added. The reaction was concentrated under reduced pressure and the residue chromatographed on silica eluting with a gradient of ethyl acetate in hexane. Concentration of the pure product fractions afforded 0.13 g (28%) of PFP ester 44 as a dark purple solid. $^1$H NMR (DMSO-d6) δ 8.86 (d, J=1.8 Hz, 1H), 8.18 (skewed dd, $J_1$=8.4 Hz, $J_2$=1.8 Hz, 1H), 8.05 (skewed d, J=8.4 Hz, 1H), 7.52 (s, 2H), 3.47 (t, J=6 Hz, 4H), 2.79 (t, J=6 Hz, 4H), 1.92 (m, 4H).

3,6,7,8-Tetrahydro-6-[[3,6,7,8-tetrahydro-6[(2-[(E)-2,3,6,7-tetrahydro-1H,5H-pyrido[3,2,1-ij]quinolin-9-yldiazenyl]-1,3-benzothiazol-6-yl)carbonyl]benzo[1,2-b:4,3-b']dipyrrol-2-yl]carbonyl]benzo[1,2-b:4,3-b']dipyrrole-2-carboxylic acid (45)

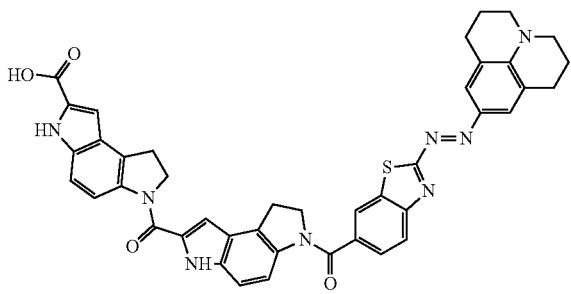 [SMILES: O=C(O)c1cc2c3c(ccc2[nH]1)N(C(=O)c1cc2c4c(ccc2[nH]1)N(C(=O)c1ccc2nc(/N=N/c5cc6c7c(c5)CCCN7CCC6)sc2c1)CC4)CC3]

To a solution of 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (0.24 mmol) in 2 mL of anhydrous DMF was added 0.2 mL of triethylamine followed by 0.13 g (0.24 mmol) of PFP ester 44. After being stirred at 50° C. for 6 h the reaction was concentrated under reduced pressure to yield a dark purple residue. To isolate the product the residue was resuspended in MeOH (10 mL), the precipitated material was collected by filtration, washed with MeOH (2×5 mL) and dried to afford 0.181 g (100%) of compound 45 as a dark purple solid. $^1$H NMR (DMSO-d6) δ 12.9 (br s, 1H), 11.84 (s, 1H), 11.76 (s, 1H), 8.4-8.1 (m, 3H), 7.98 (d, J=8.4 Hz, 1H), 7.68 (br d, J=7.8 Hz, 1H), 7.48 (s, 2H), 7.3 (m, 2H), 7.07 (d, J=1.5 Hz, 1H), 7.05 (d, J=1.5 Hz, 1H), 4.63 (t, J=7.8 Hz, 2H), 4.20 (t, J=7.5 Hz, 2H), 3.4 (m, 6H), 3.27 (m, 2H), 2.78 (t, J=6 Hz, 4H), 1.91 (m, 4H).

Pentafluorophenyl 3,6,7,8-tetrahydro-6-[[3,6,7,8-tetrahydro-6[(2-[(E)-2,3,6,7-tetrahydro-1H,5H-pyrido[3,2,1-ij]quinolin-9-yldiazenyl]-1,3-benzothiazol-6-yl)carbonyl]benzo[1,2-b:4,3-b']dipyrrol-2-yl]carbonyl]benzo[1,2-b:4,3-b']dipyrrole-2-carboxylic acid (46)

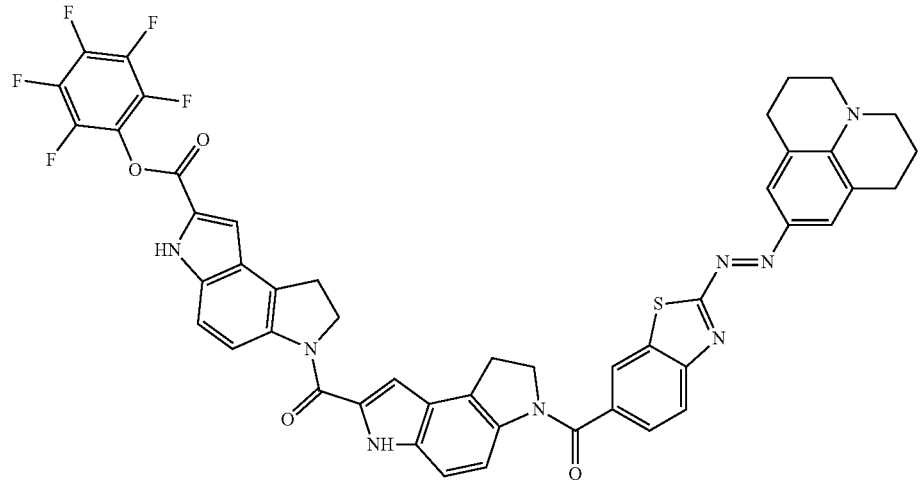 [SMILES: O=C(Oc1c(F)c(F)c(F)c(F)c1F)c1cc2c3c(ccc2[nH]1)N(C(=O)c1cc2c4c(ccc2[nH]1)N(C(=O)c1ccc2nc(/N=N/c5cc6c7c(c5)CCCN7CCC6)sc2c1)CC4)CC3]

To a suspension of 45 (0.175 g, 0.23 mmol) in DMF (2.5 mL) was added triethylamine (0.2 mL) followed by two 0.1 mL portions of PFP-TFA over the course of 3 hours. DMF was removed under reduces pressure and the residue triturated with 2-propanol (5 mL). The resultant insoluble material was collected by filtration, washed with 2-propanol (2×5 mL) and dried under reduced pressure to afford 0.20 g (95%) of PFP ester 46 as a dark purple solid. $^1$H NMR (DMSO-d6) δ 12.53 (s, 1H), 11.78 (s, 1H), 8.6-7.0 (aromatic protons, 11H), 4.66 (t, J=7.8 Hz, 2H), 4.20 (t, J=7.5 Hz, 2H), 3.9-3.0 (m, 8H), 3.27 (m, 2H), 2.77 (m, 4H), 1.90 (m, 4H).

Ethyl 6-{(E)-[2-(pyrrolidin-1-yl)-1,3-thiazol-5-yl]diazenyl}-1,3-benzothiazole-2-carboxylate (47)

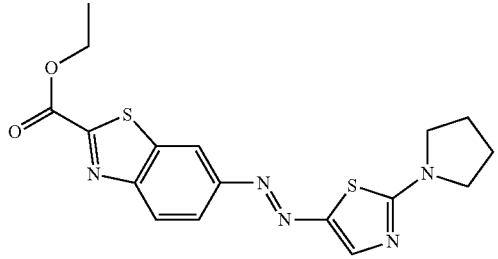 [SMILES: CCOC(=O)c1nc2ccc(/N=N/c3cnc(N4CCCC4)s3)cc2s1]

To a suspension of ethyl 5-amino-1,3-benzothiazole-2-carboxylate (prepared by Fe/NH$_4$Cl/water/EtOH reduction of ethyl 5-nitro-1,3-benzothiazole-2-carboxylate (U.S. Pat. No. 8,586,759)) (0.9 g, 3.57 mmol) in water (20 mL) was added conc. HCl (0.625 mL). The mixture was stirred at room temperature for 5 min and then cooled to 0-4° C. A solution of NaNO$_2$ (0.246 g) in water (5 mL) was added with stirring over the course of 5 min. The reaction was stirred for 10 min and then warmed to room temperature and stirred for another 10 min. To the resultant solution of diazonium salt was added a solution of 2-(pyrrolidin-1-yl)-1,3-thiazole (0.66 g, 4.28 mmol) in 10 mL of methanol followed by solid sodium acetate, trihydrate (1.35 g). The reaction was stirred at room temperature for 2 h to give a thick orange suspension. The precipitated material was collected by filtration, washed with water and dried to give crude product, which was then re-crystallized from ethyl acetate to afford 0.91 g (66%) of dye 47 as an orange solid. $^1$H NMR (DMSO-d6) δ 8.45 (d, J=1.8 Hz, 1H), 8.26 (s, 1H), 8.24 (d, J=9 Hz, 1H), 7.92 (dd, J$_1$=9 Hz, J$_2$=1.8 Hz, 1H), 4.44 (q, J=6.9 Hz, 2H), 3.56 (br s, 4H), 2.14 (m, 4H), 1.34 (t, J=6.9 Hz, 3H).

6-{(E)-[2-(pyrrolidin-1-yl)-1,3-thiazol-5-yl]diazenyl}-1,3-benzothiazole-2-carboxylic acid (48)

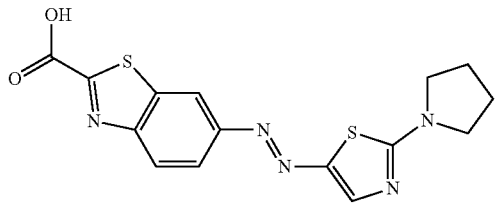 [SMILES: O=C(O)c1nc2ccc(/N=N/c3cnc(N4CCCC4)s3)cc2s1]

To a solution of 47 (0.90 g, 2.32 mmol) in a mixture of THF (48 mL) and MeOH (32 mL) was added 16 mL of 1N NaOH. The reaction was stirred at 50° C. for 1.5 h then cooled, neutralized with 1N HCl (16 mL) and concentrated under reduced pressure to about 30 mL. The resulting precipitate was collected by filtration, washed with water and dried to afford 0.81 g (97%) of compound 48 as a black solid. $^1$H NMR (DMSO-d6) δ 8.40 (s, 1H), 8.22 (s, 1H), 8.19 (d, J=8.4 Hz, 1H), 7.88 (d, J=8.4 Hz, 1H), 3.55 (br s, 4H), 2.01 (br s, 4H).

Pentafluorophenyl 6-{(E)-[2-(pyrrolidin-1-yl)-1,3-thiazol-5-yl]diazenyl}-1,3-benzothiazole-2-carboxylate (49)

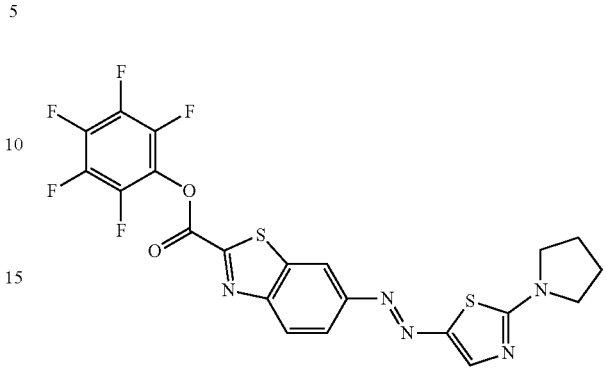

Prior to reaction starting acid 48 (0.8 g, 2.22 mmol) was dried by co-evaporation with anhydrous DMF (10 mL) supplemented with 0.5 mL of triethylamine and then re-dissolved in a fresh portion of DMF (10 mL). To this solution was added triethylamine (0.5 mL) followed by PFP-TFA (0.4 mL, 2.3 mmol). Within minutes a thick suspension was obtained. The reaction was agitated on an orbital shaker for 1 h, then concentrated under reduced pressure and the resultant residue chromatographed on silica eluting with ethyl acetate. Concentration of the product-containing fractions and re-crystallization from ethyl acetate afforded 0.803 g (69%) of PFP ester 49 as a red solid. $^1$H NMR (CDCl$_3$) δ 8.34 (d, J=1.8 Hz, 1H), 8.32 (d, J=9 Hz, 1H), 8.14 (s, 1H), 8.07 (dd, J$_1$=9 Hz, J$_2$=1.8 Hz, 1H), 3.67 (br s, 4H), 2.03 (m, 4H).

3,6,7,8-Tetrahydro-6-[(6-{(E)-[2-(pyrrolidin-1-yl)-1,3-thiazol-5-yl]diazenyl}-1,3-benzothiazol-2-yl)carbonyl]benzo[1,2-b:4,3-b']dipyrrole-2-carboxylic acid (50)

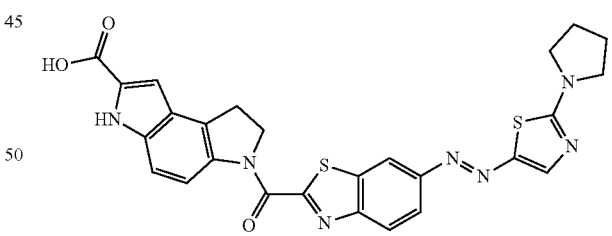

To a solution of 3,6,7,8-tetrahydro-benzo[1,2-b:4,3-b']dipyrrole-2-carboxylic acid (0.69 mmol) and 0.45 mL of triethylamine in 4.5 mL of DMF was added 0.35 g (0.67 mmol) of PFP ester 49. The reaction was stirred for 2 hours at 50° C. and cooled to room temperature. The precipitated material was collected by filtration, washed with DMF (2 mL), acetone (3×15 mL), methanol (2×10 ml) and dried to give 0.375 g (100%) of compound 50 as a brick-red solid. $^1$H NMR (DMSO-d6) δ 11.70 (s, 1H), 8.39 (s, 1H), 8.28 (d, J=9.3 Hz, 1H), 8.22 (s, 1H), 8.17 (d, J=9 Hz, 1H), 7.87 (d, J=9 Hz, 1H), 7.32 (d, J=9.3 Hz, 1H), 6.93 (s, 1H), 4.89 (m, 2H), 3.7-3.3 (m, 6H), 2.01 (br s, 4H).

Pentafluorophenyl 3,6,7,8-tetrahydro-6-[(6-{(E)-[2-(pyrrolidin-1-yl)-1,3-thiazol-5-yl]diazenyl}-1,3-benzothiazol-2-yl)carbonyl]benzo[1,2-b:4,3-b']dipyrrole-2-carboxylate (51)

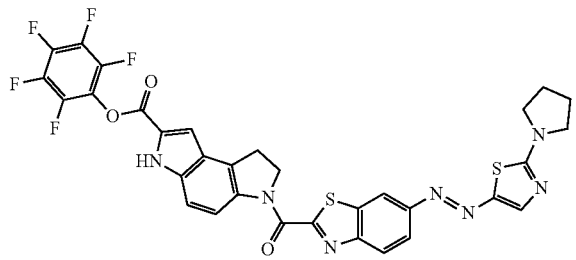 [SMILES: O=C(Oc1c(F)c(F)c(F)c(F)c1F)c1cc2c3c(ccc2[nH]1)N(C(=O)c1nc2ccc(/N=N/c4cnc(N5CCCC5)s4)cc2s1)CC3]

PFP-TFA (a total of 0.35 mL, 1.63 mmol) was added in several portions over the course of 20 h to a suspension of 50 (0.36 g, 0.66 mmol) and triethylamine (0.4 mL) in 5 mL of anhydrous DMF until no more starting material was found by HPLC analysis. The reaction was concentrated under reduced pressure and the obtained semi-solid residue resuspended in methanol (25 mL). The resulting solid was collected by centrifugation at 4,000 rpm for 10 min, methanol decanted and the procedure was repeated two more times. Drying under reduced pressure afforded 0.340 g (72%) of PFP ester 51 as a brick-red solid. $^1$H NMR (DMSO-d6) δ 12.62 (s, 1H), 8.48 (8.46 (d, J=9 Hz, 1H), 8.44 (d, J=1.5 Hz, 1H), 8.25 (s, 1H), 8.21 (d, J=9 Hz, 1H), 7.90 (dd, $J_1$=9 Hz, $J_2$=1.5 Hz, 1H), 7.62 (s, 1H), 7.46 (d, J=9 Hz, 1H), 4.95 (t, J=8.1 Hz, 2H), 3.55 (br s, 4H), 3.50 (t, J=8.4 Hz, 2H), 2.03 (m, 4H).

4-Phenyl-2-(pyrrolidin-1-yl)-1,3-thiazole (52)

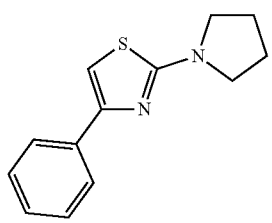 [SMILES: c1ccc(-c2csc(N3CCCC3)n2)cc1]

A mixture of 2-Bromo-4-phenyl-1,3-thiazole (5.4 g, 22.5 mmol) and pyrrolidine (5 mL, 60 mmol) was heated at 80° C. for 2.5 h, then cooled and concentrated. The resultant semi-solid was resuspended in 1:2 ethyl-acetate-hexane and the precipitate pyrrolidinium bromide removed by filtration. The filtrate was concentrated and the residue chromatographed on silica eluting with 1:2 ethyl acetate-hexane to afford 5.15 g of compound 52 as a colorless crystalline solid. $^1$H NMR (CDCl$_3$) δ 7.86 (m, 1H), 7.83 (m, 1H), 7.36 (dt, $J_1$=6 Hz, $J_2$=1.5 Hz, 2H), 7.26 (skewed dt, $J_1$=6 Hz, $J_2$=1.5 Hz, 1H), 6.66 (s, 1H), 3.51 (m, 4H), 2.04 (m, 4H).

Ethyl 5-{(E)-[4-phenyl-2-(pyrrolidin-1-yl)-1,3-thiazol-5-yl]diazenyl}-1H-indole-2-carboxylate (53)

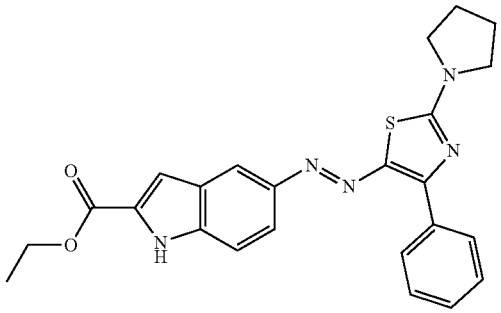 [SMILES: CCOC(=O)c1cc2cc(/N=N/c3sc(N4CCCC4)nc3-c3ccccc3)ccc2[nH]1]

To a suspension of ethyl 5-aminoindole-2-carboxylate (0.75 g, 3.67 mmol) in 20 mL of water was added 0.625 mL of conc. HCl. The stirred suspension was cooled in ice/water bath to 0-4° C. and treated with a solution of NaNO$_2$ (0.275 g, 3.98 mmol) in 5 mL of water over the course of 5 min. The reaction was stirred at 0-4° C. for 30 min then warmed to room temperature and stirred for another 30 min. To this solution was added a solution of 52 (1.1 g, 4.85 mmol) in 16 mL of methanol followed by sodium acetate, trihydrate (1.35 g) and stirring was continued for 5 h. The resultant precipitated was collected by filtration, washed with water, resuspended in 20 mL of MeOH and dried. The crude dye was re-crystallized from methanol to afford 1.42 g (87%) of dye 53 as an orange-red solid. $^1$H NMR (CDCl$_3$) δ 8.96 (br s, 1H), 8.34 (dd, $J_1$=8.1 Hz, $J_2$=1.5 Hz, 2H), 8.07 (d, J=1.8 Hz, 1H), 7.85 (dd, $J_1$=9 Hz, $J_2$=1.8 Hz, 1H), 7.55-7.35 (m, 4H), 7.30 (s, 1H), 4.42 (q, J=6.9 Hz, 2H), 3.66 (br s, 4H), 2.10 (m, 4H), 1.43 (t, J=6.9 Hz, 3H).

5-{(E)-[4-Phenyl-2-(pyrrolidin-1-yl)-1,3-thiazol-5-yl]diazenyl}-1H-indole-2-carboxylic acid (54)

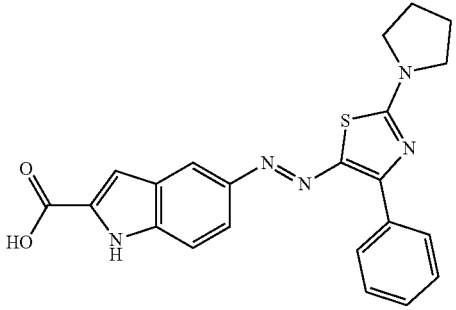 [SMILES: O=C(O)c1cc2cc(/N=N/c3sc(N4CCCC4)nc3-c3ccccc3)ccc2[nH]1]

A suspension of 53 (1.3 g, 2.92 mmol) in a mixture of THF (60 mL) and methanol (40 mL) was added 1N NaOH (20 mL). The reaction was stirred at 50° C. for 1.5 h, then cooled, neutralized with 1N HCl (20 mL) and concentrated to approx. 40 mL. The precipitated material was collected by filtration, washed with water and dried to afford 1.22 g (100%) of acid 54 as a dark brown solid. $^1$H NMR (DMSO-d6) δ 12.03 (s, 1H), 8.29 (d, J=8.7 Hz, 2H), 7.98 (d, J=1.5 Hz, 1H), 7.69 (dd, $J_1$=9 Hz, $J_2$=1.8 Hz, 1H), 7.6-7.4 (m, 4H), 7.20 (d, J=1.5 Hz, 1H), 3.59 (br s, 4H), 2.04 (br s, 4H).

Pentafluorophenyl 5-{(E)-[4-phenyl-2-(pyrrolidin-1-yl)-1,3-thiazol-5-yl]diazenyl}-1H-indole-2-carboxylate (55)

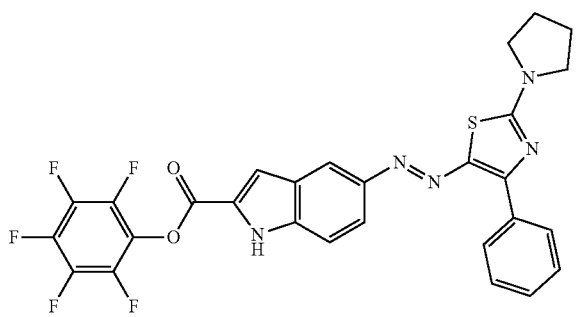 [SMILES: O=C(Oc1c(F)c(F)c(F)c(F)c1F)c1cc2cc(/N=N/c3sc(N4CCCC4)nc3-c3ccccc3)ccc2[nH]1]

Acid 54 (1.22 g, 2.92 mmol) was first dried by co-evaporation with anhydrous DMF (15 mL) then re-dissolved in fresh portion of DMF (15 mL) and treated with triethylamine (1 mL) and PFP-TFA (0.57 mL, 3.3 mmol). After being stirred at room temperature for 3 h the reaction was concentrated under reduced pressure and the resultant sold resuspended in methanol (15 mL). The insoluble material was collected by filtration, washed with methanol (2×5 mL) and dried to afford 1.71 g (87% as a DMF adduct) of PFP ester 55 as an orange solid. $^1$H NMR (CDCl$_3$) δ 9.09 (br s, 1H), 8.34 (m, 2H), 8.11 (d, J=1.8 Hz, 1H), 8.02 (br s, 1H, DMF), 7.94 (dd, J$_1$=9 Hz, J$_2$=1.8 Hz, 1H), 7.62 (d, J=1.8 Hz, 1H), 7.55-7.35 (m, 4H), 3.67 (br s, 4H), 2.96 (s, 3H, DMF), 2.89 (s, 3H, DMF), 2.12 (m, 4H).

3,6,7,8-Tetrahydro-6-[(5-{(E)-[4-phenyl-2-(pyrrolidin-1-yl)-1,3-thiazol-5-yl]diazenyl}-1H-indol-2-yl)carbonyl]benzo[1,2-b:4,3-b']dipyrrole-2-carboxylic acid (56)

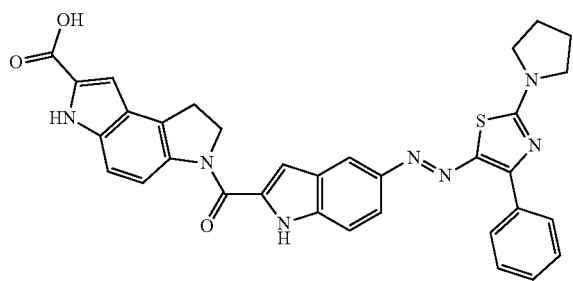 [SMILES: O=C(O)c1cc2c3c(ccc2[nH]1)N(C(=O)c1cc2cc(/N=N/c4sc(N5CCCC5)nc4-c4ccccc4)ccc2[nH]1)CC3]

To a solution of 3,6,7,8-tetrahydro-benzo[1,2-b:4,3-b']dipyrrole-2-carboxylic acid (0.79 mmol) in 5 mL of DMF was added 0.5 mL of triethylamine followed by 0.53 g (0.79 mmol) of PFP ester 55. The mixture was stirred for a few minutes to give an almost complete solution before product precipitation began. The suspension was heated at 50° C. for 2 h and then diluted with methanol (10 mL). The precipitate was collected by filtration, washed with methanol (3×10 mL) and dried to afford 0.545 g (100% as triethylammonium salt) of compound 56 as an orange-red solid. $^1$H NMR (DMSO-d6) δ 11.95 (s, 1H), 11.56 (s, 1H), 8.31 (m, 2H), 8.22 (br d, J=8.4 Hz, 1H), 7.99 (d, J=1.5 Hz, 1H), 7.69 (dd, J$_1$=9 Hz, J$_2$=1.8 Hz, 1H), 7.6-7.4 (m, 4H), 7.29 (d, J=9 Hz, 1H), 7.26 (s, 1H), 6.89 (s, 1H), 4.65 (t, J=8.1 Hz, 2H), 3.60 (br s, 4H), 3.41 (t, J=8.4 Hz, 2H), 2.67 (q, J=6.9 Hz, 6H), 2.04 (m, 4H), 1.03 (t, J=7.2 Hz, 9H).

Pentafluorophenyl 3,6,7,8-tetrahydro-6-[(5-{(E)-[4-phenyl-2-(pyrrolidin-1-yl)-1,3-thiazol-5-yl]diazenyl}-1H-indol-2-yl)carbonyl]benzo[1,2-b:4,3-b']dipyrrole-2-carboxylate (57)

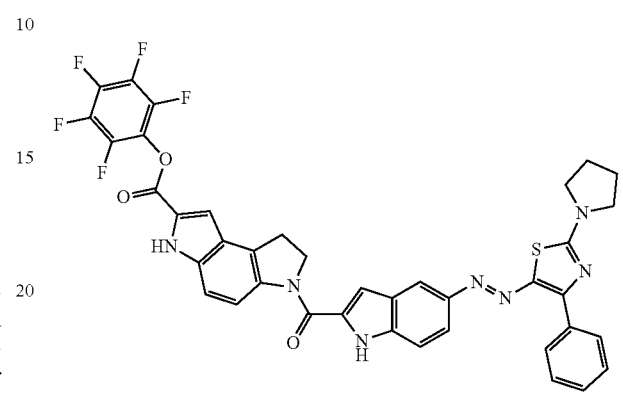

Before starting the reaction, acid 56 (0.545 g, 0.79 mmol) was dried by co-evaporation with anhydrous DMF (20 mL), then re-dissolved in fresh portion of DMF (6 mL) and treated with triethylamine (0.5 mL). PFP-TFA was added in several 0.1 mL portions over the period of 9 h until no more starting acid 56 was found by HPLC analysis. A total of 0.8 mL (4.66 mmol) of PFP-TFA was added. The resultant suspension was concentrated and the residue triturated in methanol (10 mL). The solid was collected by filtration, washed with methanol and dried to afford 0.6 g (99%) of PFP ester 57 as a red-orange solid. This product was partially TFA-blocked at the indole NH groups. $^1$H NMR (DMSO-d6) δ 12.55 (s, 0.4H), 11.98 (s, 1H), 8.33 (m, 2H), 8.00 (s, 1H), 7.8-7.2 (aromatic protons, approx. 9H), 4.70 (t, J=8.4 Hz, 2H), 3.60 (br s, 4H), 5.52 (m obscured by water signal, 2H), 2.05 (br s, 4H).

3,6,7,8-Tetrahydro-6-[[6-acetyl-3,6,7,8-tetrahydrobenzo[1,2-b:4,3-b']dipyrrol-2-yl]carbonyl]benzo[1,2-b:4,3-b']dipyrrole-2-carboxylic acid (58)

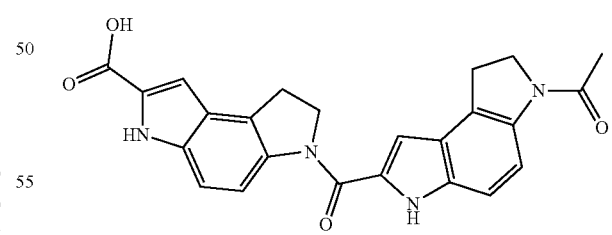

Acetic anhydride (0.12 mL, 1.27 mmol) was added to a solution of 3,6,7,8-tetrahydro-6-[(3,6,7,8-tetra hydrobenzo[1,2-b:4,3-b']dipyrrol-2-yl)carbonyl]benzo[1,2-b:4,3-b']dipyrrole]-2-carboxylic acid (1.0 mmol) and 0.4 mL of triethylamine in 10 mL of DMF. Precipitation of the product started within minutes after the addition. Reaction was allowed to continue for 15 h, the precipitated material was collected by filtration, washed with acetone (3×15 mL) and dried to afforded 0.36 g (84%) of 58 as an off-white solid.

¹H NMR (DMSO-d6) δ 13.0 (br s, 1H), 11.85 (d, J=1.8 Hz, 1H), 11.70 (d, J=1.8 Hz), 8.28 (br d, J=8.7 Hz, 1H), 8.17 (d, J=8.7 Hz, 1H), 7.33 (d, J=9.3 Hz, 1H), 7.29 (d, J=8.4 Hz, 1H), 7.07 (d, J=1.2 Hz, 1H), 7.05 (d, J=1.5 Hz, 1H), 4.65 (t, J=8.1 Hz, 2H), 4.22 (t, J=8.4 Hz, 2H), 3.43 (t, 8.1 Hz, 2H), 3.39 (m partially obscured by the water signal, 2H), 2.18 (s, 3H).

Pentafluorophenyl 3,6,7,8-tetrahydro-6-[[6-acetyl-3,6,7,8-tetrahydrobenzo[1,2-b:4,3-b']dipyrrol-2-yl]carbonyl]benzo[1,2-b:4,3-b']dipyrrole-2-carboxylate (59)

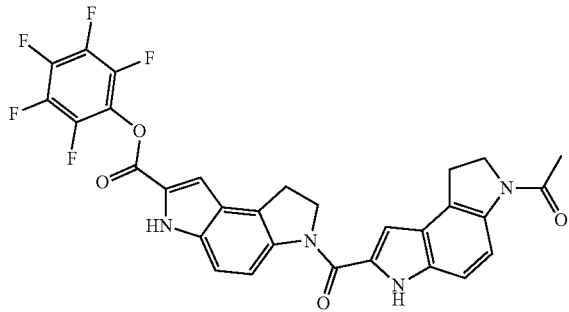 [SMILES: CC(=O)N1CCc2c1ccc1[nH]c(C(=O)N3CCc4c3ccc3[nH]c(C(=O)Oc5c(F)c(F)c(F)c(F)c5F)cc43)cc21]

PFP-TFA was added in several portions (0.04-0.12 mL each) with stirring over the period of 20 h to a solution of 58 (0.35 g, 0.82 mmol) and triethylamine (0.4 mL) in 10 mL of anhydrous DMF until no more starting material was found by HPLC analysis. DMF was removed under reduced pressure and the residue resuspended in acetone (10 mL). The insoluble material was collected by filtration, washed with acetone and dried to afford 0.46 g (94%) of 59 as an off-white solid. ¹H NMR (DMSO-d6) δ 12.56 (d, J=1.8 Hz, 1H), 11.73 (d, J=1.5 Hz), 8.44 (br d, J=9.3 Hz, 1H), 8.19 (d, J=9 Hz, 1H), 7.97 (s, 1H), 7.61 (d, J=1.5 Hz, 1H), 7.45 (d, J=9 Hz, 1H), 7.31 (d, 9 Hz, 1H), 7.08 (d, J=1.5 Hz, 1H), 4.69 (t, J=8.4 Hz, 2H), 4.22 (t, J=8.4 Hz, 2H), 3.49 (t, 8.4 Hz, 2H), 3.39 (m partially obscured by the water signal, 2H), 2.19 (s, 3H).

Example 2. Preparation of DSQ-Modified 6-aminohexane-1,2-diol Synthesis Solid Supports (6-N-(Fluorenylmethoxycarbonyl)amino-1-(4,4'-dimethoxytriphenylmethoxy)hex-2-yl)oxy-4-oxobutanoyl Polystyrene Support (ID #349 PS)

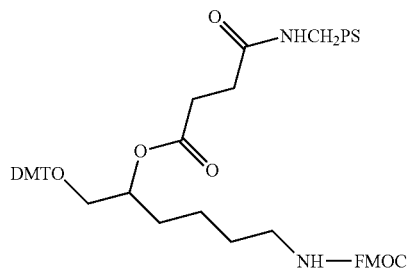

(6-N-(Fluorenylmethoxycarbonyl)amino-1-(4,4'-dimethoxytriphenylmethoxy)hex-2-yl)oxy-4-oxobutanoyl Polystyrene Support (ID #349 PS) (DMT loading 20 μmol/g) was prepared in the same manner as the CPG support described in U.S. Pat. No. 6,492,346 starting from aminomethyl polystyrene support (33 mmol/g, Applied Biosystems PN 360865C).

Example 3. Preparation of Polystyrene Supports

General Procedure for the Preparation of Polystyrene Supports ID #473, 474-477, 479, 481-488

Step 1. FMOC Deprotection

Polystyrene support (ID #349 PS) (2.0 g) was resuspended in 15 mL of 0.2 M solution of 1,8-diazabicyclo[5.4.0]undec-7-ene (DBU) in DMF and agitated on an orbit shaker for 10 min. DMF was removed by filtration and the procedure was repeated two more times. The polystyrene support was then washed with either DMF or N-Methyl-2-pyrrolidone (NMP) (3×50 mL), depending on the choice of solvent in the next step, and immediately reacted with a PFP ester as described below.

Step 2. PFP Ester Coupling

A solution of one of the PFP ester(50 μmop synthesized as described above in Example 1 (complete list of PFP esters used in this reaction is shown in Table 3) and triethylamine (0.2 mL) in 8.5 mL of a solvent indicated in Table 3 was combined with the polystyrene support from Step 1. The suspension was agitated for the period of time indicated in Table 3 then filtered, washed with the same solvent (3×50 mL) and immediately taken to the next step.

TABLE 3

| Step 2 PFP ester | Step 2 reaction time (h) | Solvent | Resultant Polystyrene Support ID # |
| --- | --- | --- | --- |
| 5 | 18 | DMF | 473 |
| 10 | 18 | NMP | 475 |
| 20 | 18 | NMP | 476 |
| 15 | 18 | NMP | 477 |
| 25 | 12 | NMP | 479 |
| 30 | 16 | NMP | 481 |
| 59 | 20 | NMP | 482 |
| 41 | 12 | DMF | 483 |
| 35 | 20 | NMP | 484 |
| 37 | 24 | NMP | 485 |
| 46 | 20 | DMF | 486 |
| 51 | 22 | NMP | 487 |
| 49 | 24 | NMP | 488 |
| 33 | 24 | NMP | 489 |
| 57 | 15 | NMP | 490 |

Step 3. Blocking Unreacted Amino Groups

The support from step 2 was resuspended in 18 mL of pyridine and treated with 2 mL of acetic anhydride. The suspension was agitated for 30 min, then filtered, washed with DMF (3×50 mL) and acetone (3×50 mL) and dried under reduced pressure.

Example 4. Preparation of Polystyrene Support ID #478

Ethyl 2-[(E)-{4-[(6-acetyloxyhexyl)(methyl)amino]phenyl}diazenyl]-1,3-benzothiazole-6-carboxylate (60)

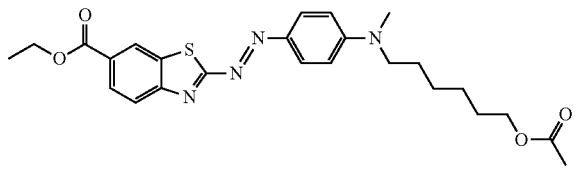 [SMILES: CCOC(=O)c1ccc2nc(/N=N/c3ccc(N(C)CCCCCCOC(C)=O)cc3)sc2c1]

To a cold (0-4° C.) suspension of ethyl 2-amino-1,3-benzothiazole-6-carboxylate (0.444 g, 2.0 mmol) in a mixture of acetic (5 mL) and propionic (5 mL) acids was added dropwise 0.62 mL of 40% nitrosylsulfuric acid with stirring. After being stirred for 3 h an almost clear yellow-orange solution was obtained which was immediately used in the next step. The solution of diazonium salt was added in several portions to a cold (0-4° C.) mixture prepared by combining a solution of 6-[methyl(phenyl)amino]hexyl acetate (WO 2008008481) (0.6 g, 2.4 mmol) in 2.5 mL of MeOH and a solution of sulfamic acid (0.060 g) in 20 mL of water. The reaction was stirred at 0-4° C. for 2 hours, neutralized by adding saturated NaHCO$_3$ in several portions and the precipitated material extracted with ethyl acetate. The extract was concentrated under reduced pressure and the obtained residue triturated with 4:1 hexane-ethyl acetate (30 mL). The resulting solid was collected by filtration, washed with MeOH (15 mL) and dried to afford 0.415 g (42%) of azo-dye 60 as a black solid. $^1$H NMR (CDCl$_3$) δ 8.55 (s, 1H), 8.13 (skewed dd, J$_1$=8.4 Hz, J$_2$=1.2 Hz, 1H), 8.07 (skewed d, J=8.4 Hz, 1H), 8.00 (d, J=9.3 Hz, 2H), 6.76 (d, J=9.3 Hz, 2H), 4.43 (q, J=7.2 Hz, 2H), 4.07 (t, J=6.6 Hz, 2H), 3.49 (t, J=7.5 Hz, 2H), 3.14 (s, 3H), 2.05 (s, 3H), 1.66 (m, 4H), 1.44 (m, 7H).

2-[(E)-{4-[(6-hydroxyhexyl)(methyl)amino]phenyl}diazenyl]-1,3-benzothiazole-6-carboxylic acid (61)

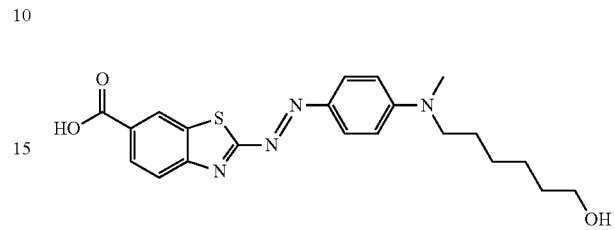

1N NaOH (6 mL) was added to a solution of azo-dye 60 (0.415 g, 0.86 mmol) in a mixture of THF (18 mL) and MeOH (12 mL). The reaction was heated at 50° C. with stirring for 1.5 h, then cooled to room temperature, neutralized with 1 N HCl (6 mL) and concentrated under reduced pressure to about 10 mL. The resulting precipitate was collected by filtration, washed with water and dried to yield 0.356 g (100%) of compound 61 as a black solid. $^1$H NMR (DMSO-d6) δ 13.08 (s, 1H), 8.58 (s, 1H), 7.99 (s, 2H), 7.83 (d, J=9.3 Hz, 2H), 6.92 (d, J=9.3 Hz, 2H), 4.32 (br s, 1H), 3.51 (t, J=6.9 Hz, 2H), 3.35 (m, 2H), 3.12 (s, 3H), 1.56 (m, 2H), 1.36 (m, 2H), 1.29 (m, 4H).

Pentafluorophenyl 2-[(E)-{4-[(6-(bis-(4-methoxyphenyl))(phenyl)methoxyhexyl)(methyl)amino]phenyl}diazenyl]-1,3-benzothiazole-6-carboxylate (62)

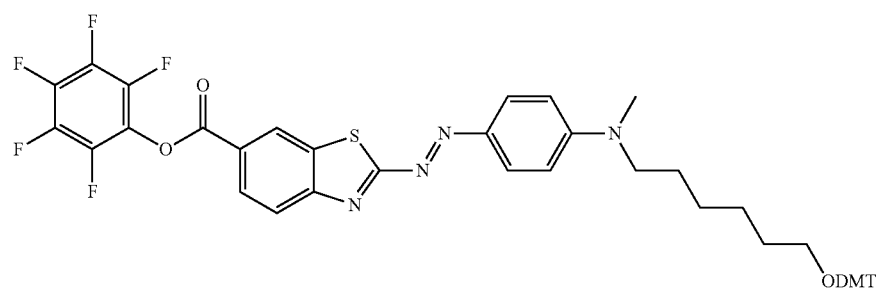

Compound 61 (0.355 g, 0.86 mmol) was dried by co-evaporation with anhydrous pyridine (25 mL) and then re-dissolved in a fresh portion of pyridine (10 mL). Dimethoxytrityl chloride (0.336 g, 1.0 mmol) was added, the reaction was stirred for 3 h and treated with PFP-TFA (0.4 mL, 2.3 mmol) and allowed to react for another 3 h. Pyridine was removed under reduced pressure and the residue partitioned between ethyl acetate and 10% citric acid. The organic phase was dried over Na$_2$SO$_4$, concentrated and the resulting material chromatographed on silica eluting with a gradient of ethyl acetate in hexane (30 to 50%). Fractions containing the desired product were concentrated to give 0.45 g (59%) of PFP ester 62 as an amorphous dark purple solid. This material was sufficiently pure for subsequent use.

3,6,7,8-Tetrahydro-6-[[3,6,7,8-tetrahydro-6[(2-[(E)-{4-[(6-(bis-(4-methoxyphenyl))(phenyl)methoxy-hexyl)(methyl)amino]phenyl}diazenyl]-1,3-benzo-thiazol-6-yl)carbonyl]benzo[1,2-b:4,3-b']dipyrrol-2-yl]carbonyl]benzo[1,2-b:4,3-b']dipyrrole-2-carboxylic acid (63)

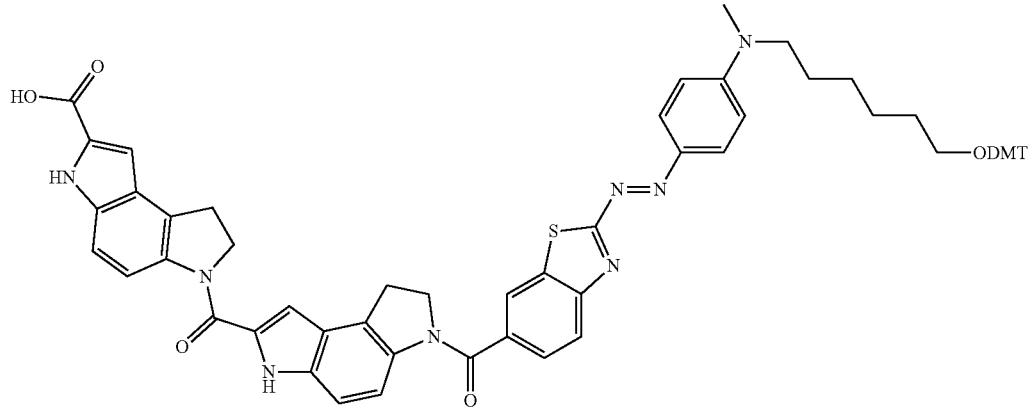

To a solution of 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (0.45 mmol) in 8 mL of anhydrous DMF was added 0.5 mL of triethylamine followed by 0.4 g (0.45 mmol) of PFP ester 62. After being stirred at room temperature for 20 h the reaction was concentrated under reduced pressure. The obtained residue was resuspended in acetone (10 mL), the precipitated material was collected by filtration, washed with more acetone (2×5 mL) and dried to afford 0.41 g (84%) of compound 63 as a black solid. $^1$H NMR (DMSO-d6) δ 11.85 (s, 1H), 11.78 (s, 1H), 8.5-6.9 (aromatic protons, 26H), 4.64 (m, 2H), 4.21 (m, 2H), 3.74 (s, 6H), 3.6-3.2 (m, 8H), 3.13 (s, 3H), 1.58 (m, 4H), 1.36 (m, 2H), 1.28 (m, 2H).

Pentafluorophenyl 3,6,7,8-tetrahydro-6-[[3,6,7,8-tetrahydro-6[(2-[(E)-{4-[(6-(bis-(4-methoxyphenyl))(phenyl)methoxyhexyl)(methyl)amino]phenyl}diazenyl]-1,3-benzothiazol-6-yl)carbonyl]benzo[1,2-b:4,3-b']dipyrrol-2-yl]carbonyl]benzo[1,2-b:4,3-b']dipyrrole-2-carboxylate (64)

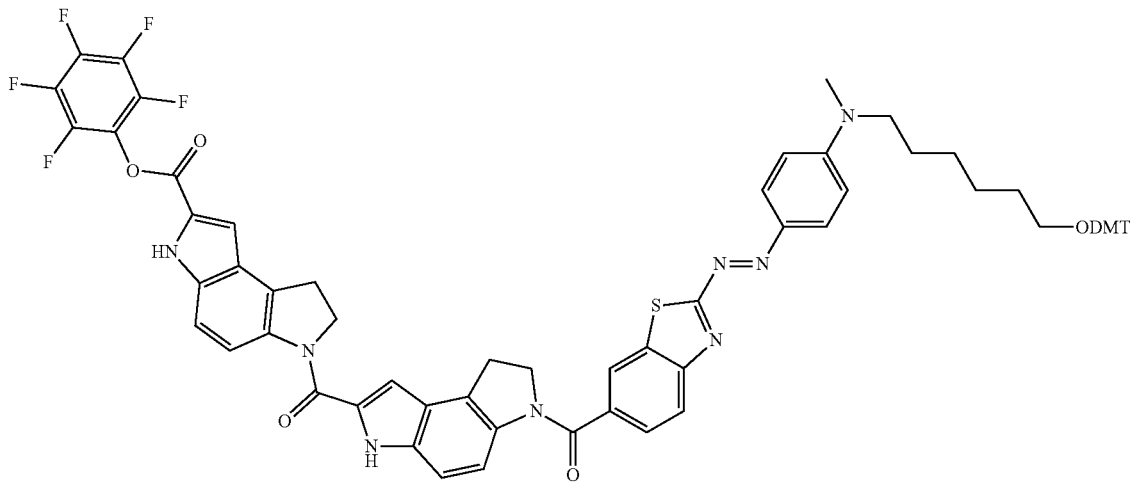

To a suspension of 63 (0.285 g, 0.26 mmol) in DMF (4 mL) was added triethylamine (0.2 mL) followed PFP-TFA (0.1 mL). After being stirred for 1 h the reaction was concentrated and the resulting residue resuspended in acetone (10 mL). The solid material was collected by filtration, washed with acetone (2×5 mL) and dried under reduced pressure to afford 0.25 g (77%) of PFP ester 64 as a dark brawn solid. $^1$H NMR (DMSO-d6) δ 12.54 (s, 1H), 11.80 (s, 1H), 8.5-6.9 (aromatic protons, 26H), 4.68 (m, 2H), 4.22 (m, 2H), 3.74 (s, 6H), 3.6-3.2 (m, 8H), 3.13 (s, 3H), 1.58 (m, 4H), 1.36 (m, 2H), 1.28 (m, 2H).

Preparation of Polystyrene Support ID #478

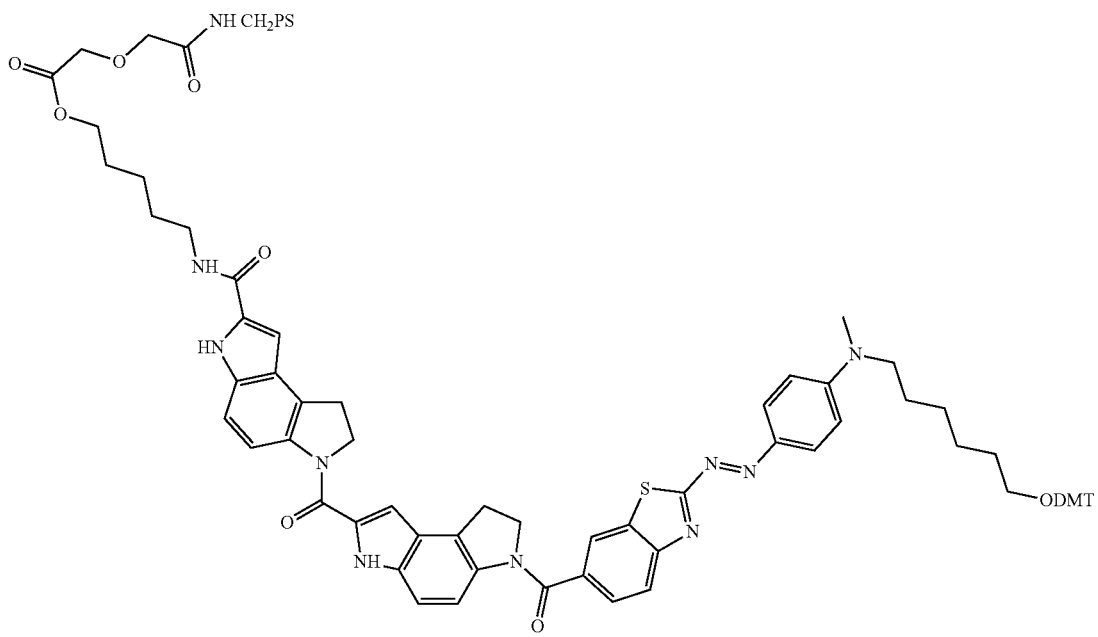

(N-MMT-5-aminopentyl)glycolate polystyrene support (U.S. Pat. No. 7,381,818) (5.0 g, 20 umol/g MMT loading) was deprotected by suspending in 30 mL of 3% trichloactetic acid in CH$_2$Cl$_2$ and filtration. The procedure was repeated approx. 10 times until no more yellow color was observed. The support then was washed with CH$_2$Cl$_2$, 10% triethylamine/CH$_2$Cl$_2$ and N-methylpyrrolidinone (NMP) before being resuspended in a solution of 64 (0.156 g, 0.12 mmol, 25 umol/g offering) and triethylamine (0.2 mL) in 25 mL of NMP. The suspension was swirled on an orbital shaker for 18 h then filtered and washed with NMP. To block unreacted aminogroups the support was suspended in pyridine (22.5 mL), treated with acetic anhydride (2.5 mL) and swirled for 30 min. The blocking reagents were removed by filtration and the support was washed with several 50 mL portions of NMP and acetone followed by drying under reduced pressure to afford polystyrene support ID #478 as a light purple solid. DMT loading was 19.0 μmol/g according to a colorimetric acid cleavage test.

Example 5. Preparation of Polystyrene Support ID #480

3-[Methyl(phenyl)amino]propyl acetate (65)

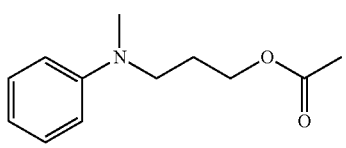

A mixture of N-methylaniline (23.6 mL, 0.218 mol), 3-chloropropylacetate (32.4 ml, 0.266 mol), diisopropylethylamine (46.4 mL, 0.267 mol) and sodium iodide (2.2 g, 14.7 mmol) was heated at 120° C. with stirring for 7 h before being cooled and partioned between water (500 mL) and ethyl acetate (200 mL). The organic phase was washed with brine, dried over Na$_2$SO$_4$ and concentrated. The resultant crude product was purified by vacuum distillation at 1 mmHg with the desired product distilling at approx. 110° C. yielding 35.8 g (80%) of 3-[methyl(phenyl)amino]propyl acetate (65) as a pale yellow liquid. $^1$H NMR (CDCl$_3$) δ 7.7 (m, 2H), 6.7 (m, 3H), 4.11 (t, J=6.3 Hz, 2H), 3.42 (t, J=6.9 Hz, 2H), 2.93 (s, 3H), 2.07 (s, 3H), 1.91 (p, J=6.6 Hz, 2H).

2-[(E)-(4-{[3-(Acetyloxy)propyl](methyl)amino}phenyl)diazenyl]-1,3-benzothiazole-6-carboxylic acid (66)

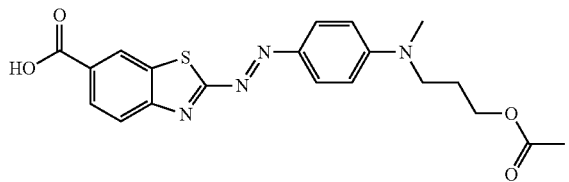 [SMILES: CC(=O)OCCCN(C)c1ccc(/N=N/c2nc3ccc(C(=O)O)cc3s2)cc1]

To a cold (0-4° C.) suspension of 2-amino-1,3-benzothiazole-6-carboxylic acid (1.25 g, 6.25 mmol) in a mixture of acetic (16 mL) and propionic (16 mL) acids was added dropwise 40% nitrosylsulfuric acid (2.0 mL) over the course of 5 min. The reaction was stirred at 0-4° C. for 2 h and then at room temperature for 2 h to give a light yellow suspension. This suspension was added slowly (approx. 5 min) to a cold (0-4° C.) mixture prepared by combining a solution of 3-[methyl(phenyl)amino]propyl acetate (65) (1.6 g, 7.7 mmol) in methanol (8 mL) and a solution of sulfamic acid (0.2 g) in water (65 mL). After being stirred for 1 h, the reaction was neutralized by adding 65 mL of triethylamine and diluted with water (500 mL). The precipitated solid was collected by filtration, washed with water and dried. The crude dye was triturated with 4:1 hexane-ethyl acetate (20 mL) and the solid was collected by filtration. Drying under reduced pressure afforded 1.66 g (64%) of sufficiently pure azo-dye 66 as a black solid. $^1$H NMR (DMSO-d6) δ 8.62 (s, 1H), 8.04 (s, 2H), 7.89 (d, J=9 HZ, 2H), 6.98 (d, J=9 Hz, 2H), 4.07 (t, J=6 Hz, 2H), 3.66 (t, J=6.6 Hz, 2H), 3.16 (s, 3H), 2.04 (s, 3H), 1.93 (p, J=6.3 Hz, 2H).

Pentafluorophenyl 2-[(E)-(4-{[3-(acetyloxy)propyl](methyl)amino}phenyl)diazenyl]-1,3-benzothiazole-6-carboxylate (67)

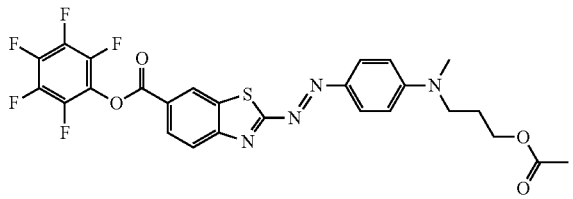 [SMILES: CC(=O)OCCCN(C)c1ccc(/N=N/c2nc3ccc(C(=O)Oc4c(F)c(F)c(F)c(F)c4F)cc3s2)cc1]

To a solution of 66 (1.66 g, 4.0 mmol) and triethylamine (0.5 mL) in 10 mL of anhydrous $CH_2Cl_2$ was added PFP-TFA in two portions over the course of 3 hours until no more starting material was found by HPLC analysis. A total of 1.1 mL (6.4 mmol) of PFP-TFA was added. The reaction was concentrated under reduced pressure and the residue resuspended in 20 mL of methanol. The precipitate was collected by filtration, washed with methanol and dried to afford 1.88 g (81%) of PFP ester 67 as dark purple solid. $^1$H NMR ($CDCl_3$) δ 8.72 (s, 1H), 8.27 (skewed dd, $J_1$=8.4 Hz, $J_2$=1.2 Hz, 1H), 8.16 (d, J=8.7 Hz, 1H), 8.03 (d, J=9 Hz, 2H), 6.79 (d, J=9 Hz, 2H), 4.16 (t, J=6 Hz, 2H), 3.63 (t, J=7.2 Hz, 2H), 3.18 (s, 3H), 2.11 (s, 3H), 2.03 (m, 2H).

3,6,7,8-Tetrahydro-6-[[3,6,7,8-tetrahydro-6[(2-[(E)-(4-{[3-(acetyloxy)propyl](methyl)amino}phenyl)diazenyl]-1,3-benzothiazol-6-yl)carbonyl]benzo[1,2-b:4,3-b']dipyrrol-2-yl]carbonyl]benzo[1,2-b:4,3-b']dipyrrole-2-carboxylic acid (68)

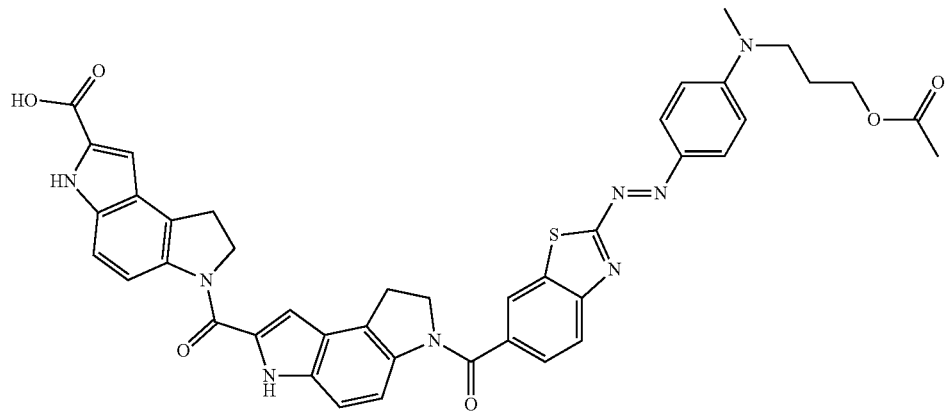 [SMILES: CC(=O)OCCCN(C)c1ccc(/N=N/c2nc3ccc(C(=O)N4CCc5c4ccc4[nH]c(C(=O)N6CCc7c6ccc6[nH]c(C(=O)O)cc76)cc54)cc3s2)cc1]

To a solution of 3,6,7,8-tetrahydro-6-[(3,6,7,8-tetrahydrobenzo[1,2-b:4,3-b']dipyrrol-2-yl)carbonyl]benzo[1,2-b:4,3-b']dipyrrole]-2-carboxylic acid (3.05 mmol) in 20 mL of anhydrous DMF was added 2 mL of triethylamine followed by 1.8 g (3.11 mmol) of PFP ester 67. The reaction was stirred at 50° C. for 3 h and then concentrated. The obtained dark residue was triturated with acetone (30 mL), the resultant solid was collected by filtration, washed with acetone (2×10 mL) and dried to afford 2.55 g (107% due to a partial triethylammonium salt form) of compound 68 as a dark brown-purple solid. $^1$H NMR (DMSO-d6) δ 11.77 (s, 1H), 11.62 (s, 1H), 8.32 (s, 1H), 8.2 (m, 2H), 8.07 (d, J=8.4 Hz, 1H), 7.89 (d, J=9 Hz, 2H), 7.74 (br d, J=8.1 Hz, 1H), 7.35 (br s, 1H), 7.29 (d, J=9 Hz, 1H), 7.08 (s, 1H), 6.98 (d, J=9.3 Hz, 2H), 6.92 (s, 1H), 4.63 (t, J=7.5 Hz, 2H), 4.21 (t, 2H), 4.07 (t, J=6 Hz, 2H), 3.66 (t, J=6.3 Hz, 2H), 3.40 (t, J=7.5 Hz, 2H), 3.31 (t, J=7.5 Hz, 2H), 3.16 (s, 3H), 2.73 (m, 5H, $Et_3NH^+$), 2.04 (s, 3H), 1.95 (m, 2H), 1.05 (t, J=7.2 Hz, 8H, $Et_3NH^+$).

Pentafluorophenyl 3,6,7,8-tetrahydro-6-[[3,6,7,8-tetrahydro-6[(2-[(E)-(4-{[3-(acetyloxy)propyl](methyl)amino}phenyl)diazenyl]-1,3-benzothiazol-6-yl)carbonyl]benzo[1,2-b:4,3-b']dipyrrol-2-yl]carbonyl]benzo[1,2-b:4,3-b']dipyrrole-2-carboxylate (69)

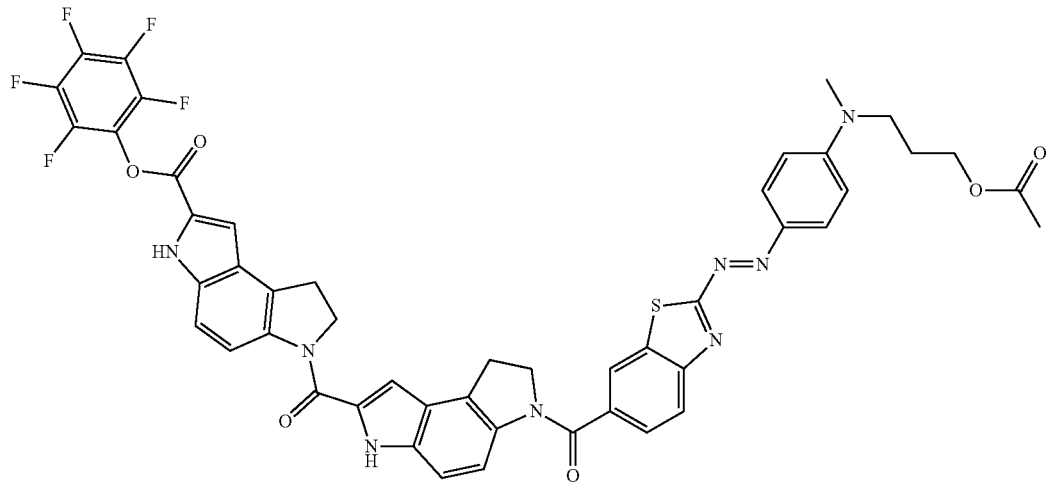 [SMILES: CC(=O)OCCCN(C)c1ccc(/N=N/c2nc3ccc(C(=O)N4CCc5c4ccc4[nH]c(C(=O)N6CCc7c6ccc6[nH]c(C(=O)Oc8c(F)c(F)c(F)c(F)c8F)cc76)cc54)cc3s2)cc1]

To a suspension of 68 (2.55 g g, 2.67 mmol) in 25 mL of anhydrous DMF was added triethylamine (1 mL) followed by PFP-TFA in several portions over the course of 4 hours until no more starting material was found by HPLC analysis. A total of 0.91 mL (5.3 mmol) of PFP-TFA was added. The precipitate was collected by filtration, washed with acetone (3×20 mL) and dried to afford 2.40 g (95%) of PFP ester 69 as a red-purple solid. $^1$H NMR (DMSO-d6) δ 12.54 (s, 1H), 11.80 (s, 1H), 8.5-8.2 (m, 3H), 8.07 (d, J=8.7 Hz, 1H), 7.89 (d, J=9 Hz, 2H), 7.74 (br d, J=8.1 Hz, 1H), 7.59 (s, 1H), 7.43 (d, J=8.7 Hz, 1H), 7.37 (br s, 1H), 7.11 (s, 1H), 6.98 (d, J=9.3 Hz, 2H), 4.68 (t, J=7.5 Hz, 2H), 4.22 (t, J=6.3 Hz, 2H), 4.07 (t, J=6.3 Hz, 2H), 3.66 (t, J=6.2 Hz, 2H), 3.48 (t, J=7.2 Hz, 2H), 3.31 (t, J=7.5 Hz, 2H), 3.16 (s, 3H), 2.04 (s, 3H), 1.93 (m, 2H).

N-(6-(bis-(4-methoxyphenyl))(phenyl)methoxyhex-1-yl)-3,6,7,8-tetrahydro-6-[3,6,7,8-tetrahydro-6[(2-[(E)-(4-{[3-(acetyloxy)propyl](methyl)amino}phenyl)diazenyl]-1,3-benzothiazol-6-yl)carbonyl]benzo[1,2-b:4,3-b']dipyrrol-2-yl]carbonyl]benzo[1,2-b:4,3-b']dipyrrole-2-carboxamide (70)

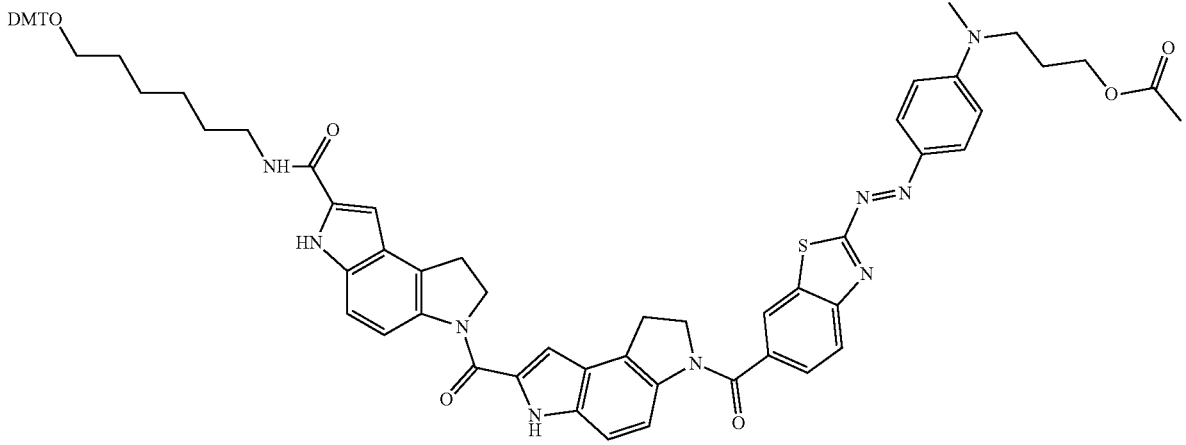

A solution of O-DMT-, N-Fmoc-protected 6-aminohexan-1-ol (S. Mahajan (2006)) (0.55 g, 0.86 mmol) in a mixture of DMF (6 mL) and triethylamine (6 mL) was heated at 80° C. for 1 h, then concentrated and re-dissolved in a fresh portion of DMF (30 mL) supplemented with triethyllamine (0.45 mL). To this solution was added 0.74 g (0.78 mmol) of 69 and the reaction was stirred at 50° C. for 5 h and then at room temperature for 18 h. DMF was removed under reduced pressure and the resultant residue triturated with methanol. Filtration of the obtained solid followed by washing with methanol and drying yielded 0.885 g (87%) of compound 70 as a purple solid. ¹H NMR (DMSO-d6) δ 11.78 (s, 1H), 11.64 (s, 1H), 8.45 (br t, 1H), 8.33 (s, 1H), 8.20 (m, 2H), 8.08 (d, J=8.4 Hz, 1H), 7.90 (d, J=9.3 Hz, 2H), 7.75 (br d, J=6.9 Hz, 1H), 7.4-7.25 (m, 11H), 7.08 (s, 2H), 6.98 (d, J=9.3 Hz, 2H), 6.89 (d, J=9 Hz, 4H), 4.65 (t, J=7.5 Hz, 2H), 4.22 (t, J=6.3 Hz, 2H), 4.07 (t, J=6 Hz, 2H), 3.73 (s, 6H), 3.66 (t, J=6.2 Hz, 2H), 3.43 (t, J=7.2 Hz, 2H), 3.28 (m, 4H), 3.16 (s, 3H), 2.96 (t, J=6 Hz, 2H), 2.04 (s, 3H), 1.94 (m, 2H), 1.55 (m, 4H), 1.32 (m, 4H).

N-(6-(bis-(4-methoxyphenyl))(phenyl)methoxyhex-1-yl)-3,6,7,8-tetrahydro-6-[[3,6,7,8-tetrahydro-6[(2-[(E)-(4-{[3-hydroxypropyl](methyl)amino}phenyl)diazenyl]-1,3-benzothiazol-6-yl)carbonyl]benzo[1,2-b:4,3-b']dipyrrol-2-yl]carbonyl]benzo[1,2-b:4,3-b']dipyrrole-2-carboxamide (71)

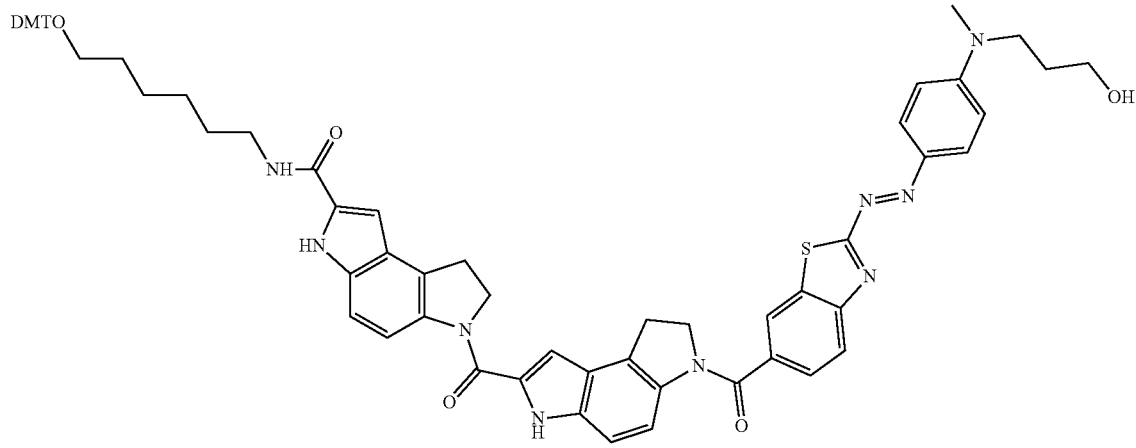

To a solution of 70 (0.61 g, 0.52 mmol) in 20 mL of DMF was added 10 mL of ethanol followed by 5 mL of 1 N NaOH. The reaction was heated at 50° C. with stirring for 30 min, then concentrated and the resultant residue resuspended in methanol (30 mL). The obtained solid was collected by filtration, washed with methanol (2×30 mL) and dried to afford 0.562 g (95%) of 71 as a purple solid. ¹H NMR (DMSO-d6) δ 11.77 (s, 1H), 11.64 (s, 1H), 8.45 (br t, 1H), 8.31 (s, 1H), 8.20 (m, 2H), 8.08 (d, J=8.4 Hz, 1H), 7.88 (d, J=9 Hz, 2H), 7.72 (br d, J=6.9 Hz, 1H), 7.4-7.25 (m, 11H), 7.07 (s, 2H), 6.97 (d, J=9.3 Hz, 2H), 6.87 (d, J=8.7 Hz, 4H), 4.65 (t, J=7.5 Hz, 2H), 4.21 (t, J=6.3 Hz, 2H), 3.71 (s, 6H), 3.62 (t, J=6.3 Hz, 2H), 3.49 (m, 2H), 3.39 (t, J=7.2 Hz, 2H), 3.27 (m, 4H), 3.16 (s, 3H), 2.92 (t, J=6 Hz, 2H), 1.76 (m, 2H), 1.54 (m, 4H), 1.31 (m, 4H).

N-(6-(bis-(4-methoxyphenyl))(phenyl)methoxyhex-1-yl)-3,6,7,8-tetrahydro-6-[[3,6,7,8-tetrahydro-6-[(2-[(E)-(4-{[3-{[4-oxo-4-(pentafluorophenoxy)butanoyl]oxy}propyl](methyl)amino}phenyl)diazenyl]-1,3-benzothiazol-6-yl)carbonyl]benzo[1,2-b:4,3-b']dipyrrol-2-yl]carbonyl]benzo[1,2-b:4,3-b']dipyrrole-2-carboxamide (72)

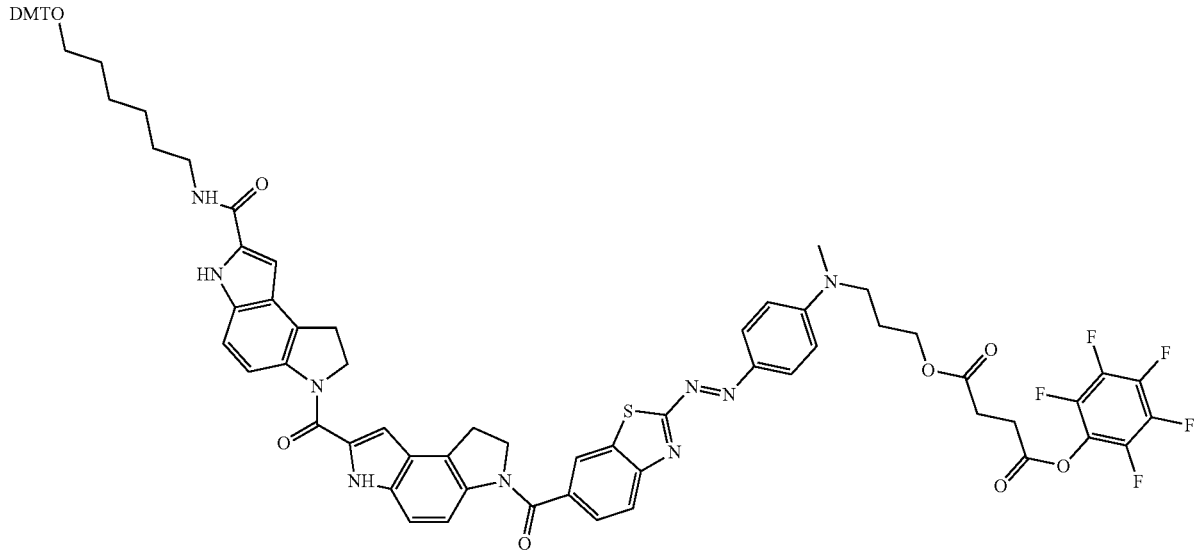

Compound 71 (0.56 g, 0.49 mmol) was dried by co-evaporation with anhydrous DMF and then re-dissolved in a fresh portion (10 mL) of DMF. Triethylamine (0.3 mL), N-methylimidazole (0.1 mL) and succinic anhydride (0.10 g, 1.0 mmol) were added and the reaction was stirred at 50° C. for 7 h until no starting material was found by HPLC analysis. The reaction was cooled and treated with triethylamine (0.2 mL) and PFP-TFA (0.21 mL, 1.22 mmol). After being stirred for 2 h the reaction was concentrated under reduced pressure and the resultant semi-solid resuspended in cold methanol (50 mL). The insoluble material was collected by filtration, washed with methanol (3×10 mL) and dried to afford 0.642 g (93%) of PFP ester 72 as a red-purple solid.

$^1$H NMR (DMSO-d6) δ 11.78 (s, 1H), 11.64 (s, 1H), 8.45 (br t, 1H), 8.32 (s, 1H), 8.20 (m, 2H), 8.08 (d, J=8.4 Hz, 1H), 7.86 (d, J=9 Hz, 2H), 7.76 (br d, J=6.9 Hz, 1H), 7.4-7.25 (m, 11H), 7.08 (s, 2H), 6.97 (d, J=9.3 Hz, 2H), 6.88 (d, J=8.4 Hz, 4H), 4.65 (t, J=7.5 Hz, 2H), 4.22 (t, J=6.3 Hz, 2H), 4.14 (t, J=5.4 Hz, 2H), 3.72 (s, 6H), 3.67 (m, 2H), 3.40 (m, 2H), 3.28 (m, 4H), 3.15 (s, 3H), 3.07 (t, J=6 Hz, 2H), 2.96 (t, J=6 Hz, 2H), 2.79 (t, J=6 Hz, 2H), 1.95 (m, 2H), 1.54 (m, 4H), 1.33 (m, 4H).

Preparation of Polystyrene Support ID #480

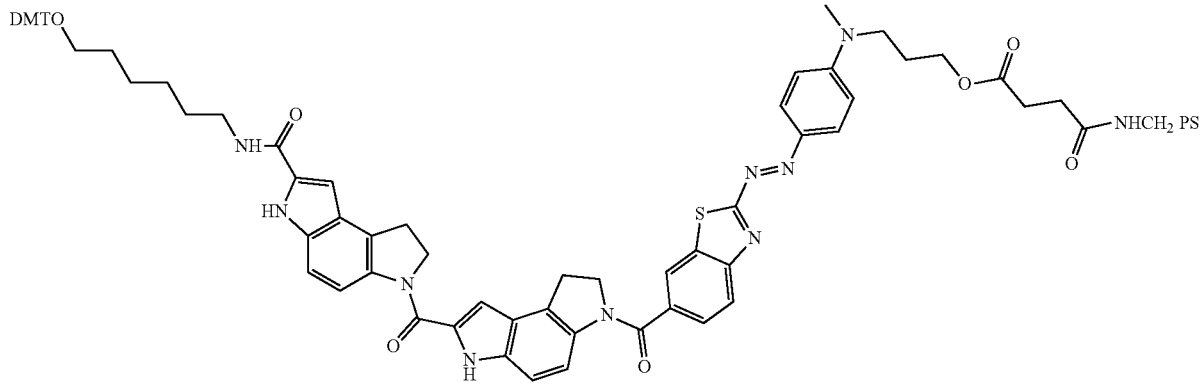

Aminomethyl-polystyrene support (33 umol/g amine capacity, Applied Biosystems, PN 360865C) (5.0 g) was added to a solution of 72 (0.12 g, 0.14 mmol, 17 umol/g offering) and triethylamine (0.5 mL) in 25 ml of DMF. The suspension was swirled on an orbital shaker for 22 h then filtered and washed with DMF. To block unreacted amino-groups the support was suspended in pyridine (22.5 mL), treated with acetic anhydride (2.5 mL) and swirled for 30 min. The blocking reagents were removed by filtration and the support was washed with several 50 mL portions of DMF and acetone followed by drying under reduced pressure to afford polystyrene support ID #480 as a light purple solid. DMT loading was 16.1 µmol/g according to a colorimetric acid cleavage test.

Example 6. Preparation of a DSQ-phosphoramidite

N-ethoxycarbonyl-N-(6-(bis-(4-methoxyphenyl)) (phenyl)methoxyhex-1-yl)-3-(ethoxycarbonyl)-3,6,7, 8-tetrahydro-6-[[3-(ethoxycarbonyl)-3,6,7,8-tetra-hydro-6[(2-[(E)-(4-{[3-(acetyloxy)propyl](methyl) amino}phenyl)diazenyl]-1,3-benzothiazol-6-yl) carbonyl]benzo[1,2-b:4,3-b']dipyrrol-2-yl]carbonyl] benzo[1,2-b:4,3-b']dipyrrole-2-carboxamide (73)

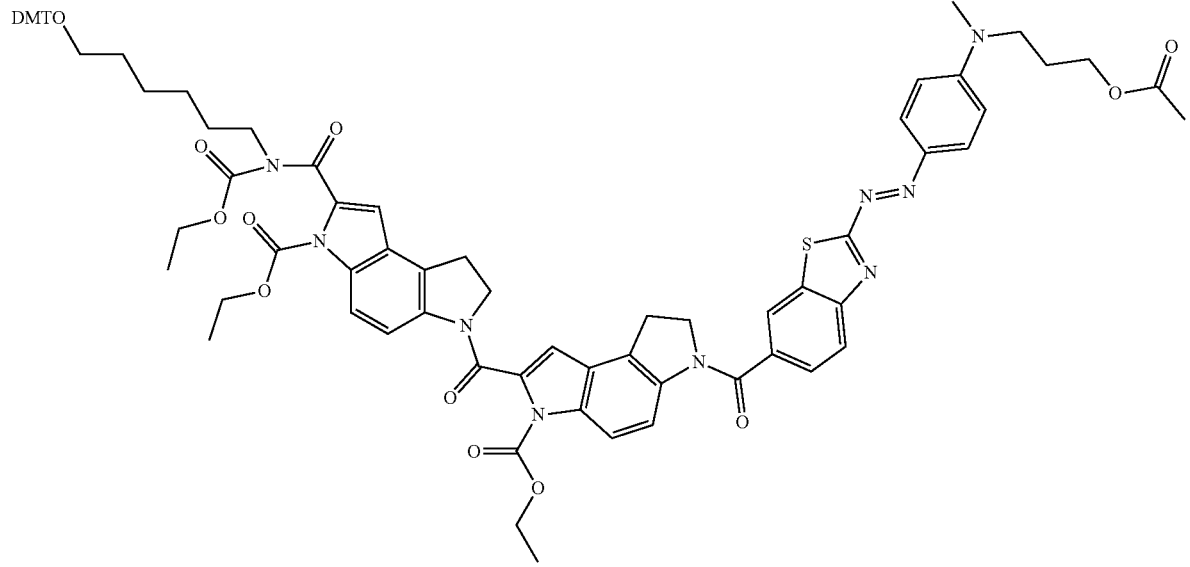

To a suspension of compound 70 (0.88 g, 0.74 mmol) in a solution of triethylamine (1 mL) and N,N-dimethylaminopyridine (0.054 g) in 13 mL of anhydrous DMF was added with stirring at 50° C. 1 mL of diethylpyrocarbonate. Five more portions of diethylpyrocarbonate totaling 6 mL were added over the course of 6 h. The reaction was allowed to proceed at room temperature for 2 more days then concentrated and partitioned between $CH_2Cl_2$ and water. The organic phase was dried over $Na_2SO_4$ and concentrated. The obtained residue was chromatographed on silica eluting with acetone in ethyl acetate (0-5%). Concentration of the main product fractions afforded 0.7 g of a purple amorphous solid. $^1$H NMR analysis indicated the presence of two compounds, one likely to be the desired triethoxycabonyl-protected compound 73 (approx. 66%) and the other one being the dioxoimidazo cyclization product (approx. 33%) as shown in FIG. 9. This mixture was taken to the next step without additional purification.

N-ethoxycarbonyl-N-(6-hydroxyhex-1-yl)-3-
(ethoxycarbonyl)-3,6,7,8-tetrahydro-6-[[3-(ethoxy-
carbonyl)-3,6,7,8-tetrahydro-6[(2-[(E)-(4-{[3-(acety-
loxy)propyl](methyl)amino}phenyl)diazenyl]-1,3-
benzothiazol-6-yl)carbonyl]benzo[1,2-b:4,3-b']
dipyrrol-2-yl]carbonyl]benzo[1,2-b:4,3-b']dipyrrole-
2-carboxamide (74)

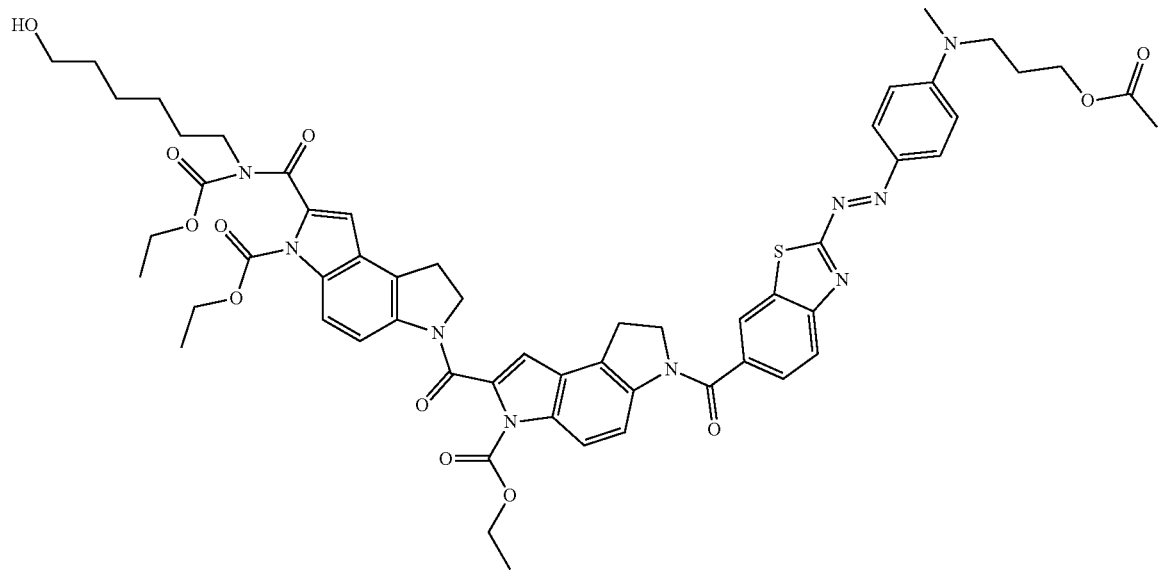 [SMILES: CCOC(=O)N(CCCCCCO)C(=O)c1cc2c3c(ccc2n1C(=O)OCC)N(C(=O)c1cc2c4c(ccc2n1C(=O)OCC)N(C(=O)c1ccc2nc(/N=N/c5ccc(N(C)CCCOC(C)=O)cc5)sc2c1)CC4)CC3]

Methanol (3 mL) and water (0.06 mL) were added to a solution of 73 (0.7 g, 0.52 mmol) in CH$_2$Cl$_2$ (12 mL) followed by trifluoroacetic acid (0.12 mL). After being kept at room temperature for 10 min the reaction was quenched by adding 0.24 mL of triethylamine and then concentrated. The obtained residue was chromatographed on silica eluting with 3:4 acetone-ethyl acetate. Concentration of the main product fractions afforded 0.52 g of a dark purple amorphous solid. $^1$H NMR spectrum was consistent with the product being a mixture of the desired 74 and the dioxoimidazo analog (FIG. 9). This mixture was taken to the next step without additional purification.

N-ethoxycarbonyl-N-(6-{(cyanomethoxy)[di(pro-
pan-2-yl)amino]phosphanyl}oxyhex-1-yl)-3-
(ethoxycarbonyl)-3,6,7,8-tetrahydro-6-[[3-(ethoxy-
carbonyl)-3,6,7,8-tetrahydro-6[(2-[(E)-(4-{[3-
(acetyloxy)propyl](methyl)amino}phenyl)diazenyl]-
1,3-benzothiazol-6-yl)carbonyl]benzo[1,2-b:4,3-b']
dipyrrol-2-yl]carbonyl]benzo[1,2-b:4,3-b']dipyrrole-
2-carboxamide (75)

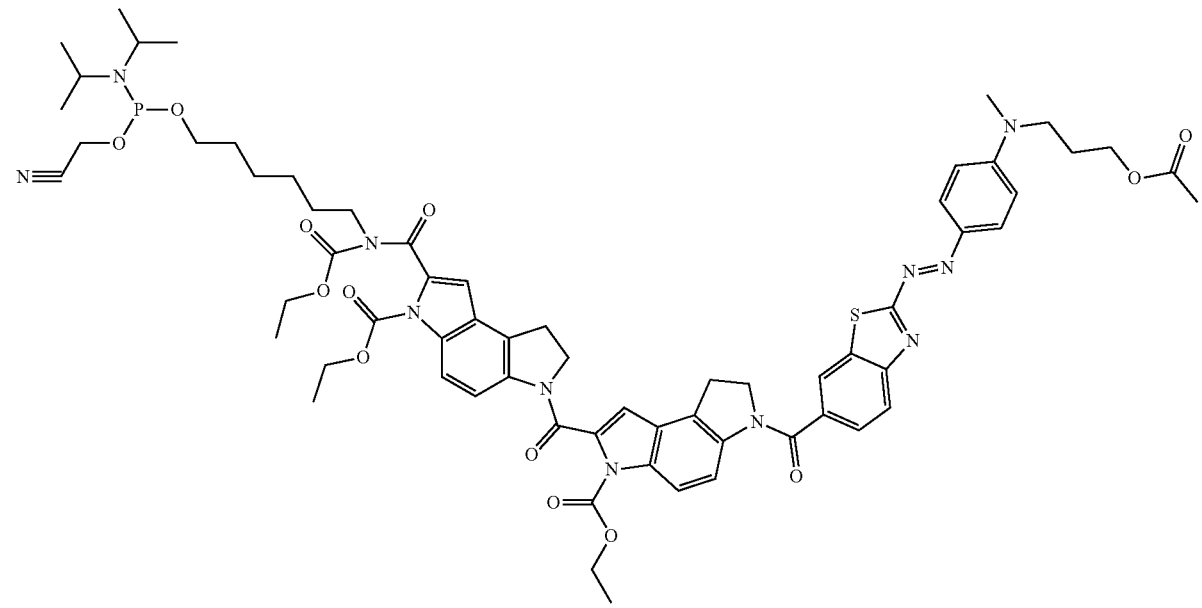 [SMILES: CCOC(=O)N(CCCCCCOP(OCC#N)N(C(C)C)C(C)C)C(=O)c1cc2c3c(ccc2n1C(=O)OCC)N(C(=O)c1cc2c4c(ccc2n1C(=O)OCC)N(C(=O)c1ccc2nc(/N=N/c5ccc(N(C)CCCOC(C)=O)cc5)sc2c1)CC4)CC3]

To a solution of 74 (0.51 g, 0.5 mmol) in 10 mL of anhydrous CH$_2$Cl$_2$ was added diisopropylammonium tetrazolide (0.077 g) followed by 0.21 g (0.66 mmol) of 2-cyanoethyl N,N,N',N'-tetraisopropylphosphorodiamidite. The reaction was stirred for 3 h then diluted with CH$_2$Cl$_2$ (100 mL) and extracted with 50 mL of saturated NaHCO$_3$. The organic phase was washed with brine and dried over MgSO$_4$. Concentration of the extract gave an amorphous solid foam which was then re-dissolved in small amount (approx. 6 mL) ethyl acetate followed by diluting with hexane (100 mL). The resultant precipitate was collected by filtration, washed with hexane and dried to afford 0.56 g of phosphoramidite 75 as a mixture with the dioxoimidazo analog shown in FIG. 9. $^{31}$P NMR (DMSO-d6) δ 145.90, 145.87.

Example 7. Preparation of Oligonucleotide Conjugates by Post-Synthetic Modification of Amine-Tailed Oligonucleotides 2-{(E)-[4-Phenyl-2-(pyrrolidin-1-yl)-1,3-thiazol-5-yl]diazenyl}-1,3-benzothiazole-6-carboxylic acid (76)

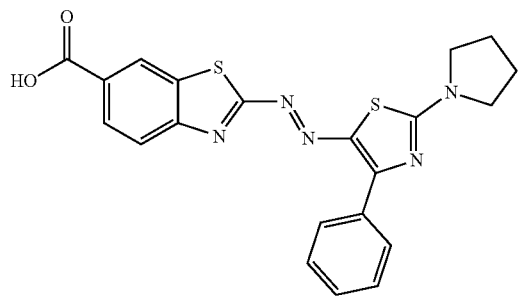 [SMILES: O=C(O)c1ccc2nc(/N=N/c3sc(N4CCCC4)nc3-c3ccccc3)sc2c1]

40% Nitrosylsulfuric acid (0.8 mL) was added over the course of 1 min to a stirred suspension of 2-amino-1,3-benzothiazole-6-carboxylic acid (0.625 g, 3.22 mmol) in a mixture of acetic (8 mL) and propionic (8 mL) acids at approx. 5° C. The reaction was then stirred at room temperature for 2 h before being used in the next step. A solution of sulfamic acid (0.1 g) in water (30 mL) was combined with a solution of 52 (0.89 g, 3.87 mmol) in methanol (30 mL). The resultant emulsion was cooled to approx. 5° C. and then slowly (approx. 2 min) added to the diazonium salt from the first step. The obtained purple mixture was stirred at 0-4° C. for 2 h, at room temperature for 1 h, then diluted with water (300 mL) and filtered to collect the precipitated product. The precipitate was washed with water and dried to afford 0.69 g (49%) of crude dye 76 as a black solid. $^1$H NMR (DMSO-d6) δ 12.25 (br s, 1H), 8.54 (s, 1H), 8.32 (m, 2H), 7.98 (skewed d, J=8.7 Hz, 1H), 7.87 (skewed d, J=8.7 Hz, 1H), 7.63 (m, 3H), 3.95 (m, 2H), 3.63 (m, 2H), 2.09 (m, 4H).

Pentafluorophenyl 2-{(E)-[4-Phenyl-2-(pyrrolidin-1-yl)-1,3-thiazol-5-yl]diazenyl}-1,3-benzothiazole-6-carboxylate (77)

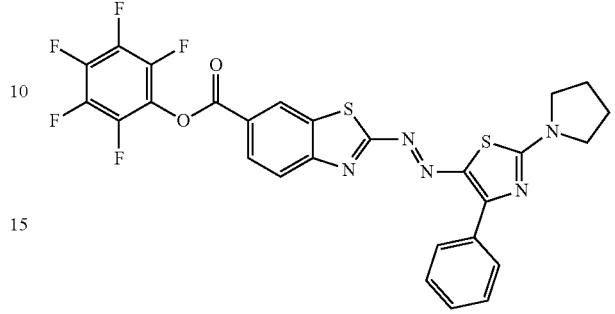

Acid 76 (0.69 g, 1.58 mmol) was first dried by co-evaporation with DMF (20 mL) supplemented with triethylamine (0.5 mL) then re-dissolved in a mixture of CH$_2$Cl$_2$ (20 mL) and triethylamine (0.5 mL). PFP-TFA (0.4 mL, 2.33 mmol) was added in one portion. The reaction was stirred for 1 h then concentrated and the obtained solid re-suspended in cold methanol (20 mL). The resultant precipitate was collected by filtration, washed with methanol (2×5 mL) and dried under reduced pressure to afford 0.76 g (80%) of PFP ester 77 as a black solid. $^1$H NMR (CDCl$_3$) δ 8.65 (s, 1H), 8.40 (m, 2H), 8.21 (skewed d, J=8.4 Hz, 1H), 8.03 (skewed d, J=8.4 Hz, 1H), 7.55 (m, 3H), 4.00 (m, 2H), 3.57 (m, 2H), 2.18 (m, 4H).

3,6,7,8-Tetrahydro-6-[(2-{(E)-[4-phenyl-2-(pyrrolidin-1-yl)-1,3-thiazol-5-yl]diazenyl}-1,3-benzothiazol-6-yl)carbonyl]benzo[1,2-b:4,3-b']dipyrrole-2-carboxylic acid (78)

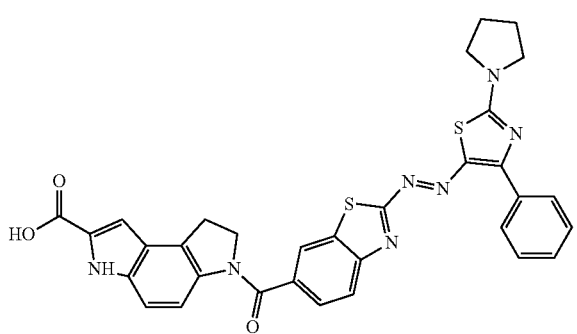 [SMILES: O=C(O)c1cc2c3c(ccc2[nH]1)N(C(=O)c1ccc2nc(/N=N/c4sc(N5CCCC5)nc4-c4ccccc4)sc2c1)CC3]

To a solution of 3,6,7,8-tetrahydro-benzo[1,2-b:4,3-b']dipyrrole-2-carboxylic acid (0.25 mmol) in 2 mL of DMF was added 0.5 mL of triethylamine followed by 0.15 g (0.25 mmol) of PFP ester 77. The mixture was stirred for a few minutes to give an almost complete solution before product precipitation began. The suspension was stirred at room temperature for 3 h, then concentrated on a rotary evaporator and the resultant black residue was re-suspended in methanol (7 mL). The obtained precipitate was collected by filtration, washed with methanol (2×2 mL) and dried under reduced pressure to afford 0.158 g (100%) of compound 78 (partial triethylammonium salt) as a black solid. $^1$H NMR (DMSO-d6) δ 11.69 (br s, 1H), 8.32 (m, 2H), 8.23 (s, 1H), 7.92 (d, J=8.4 Hz, 1H), 7.61 (m, 4H), 7.27 (br s, 1H), 6.93 (s, 1H), 4.17 (t, J=7.8 Hz, 2H), 3.92 (m, 2H), 3.61 (m, 2H), 3.25 (t, J=8.1 Hz, 2H), 2.76 (m, 2.5H, Et$_3$NH$^+$), 2.08 (m, 4H), 1.06 (t, J=7.2 Hz, 4.1H, Et$_3$NH$^+$).

Pentafluorophenyl 3,6,7,8-tetrahydro-6-[(2-{(E)-[4-phenyl-2-(pyrrolidin-1-yl)-1,3-thiazol-5-yl]diazenyl}-1,3-benzothiazol-6-yl)carbonyl]benzo[1,2-b:4,3-b']dipyrrole-2-carboxylate (79)

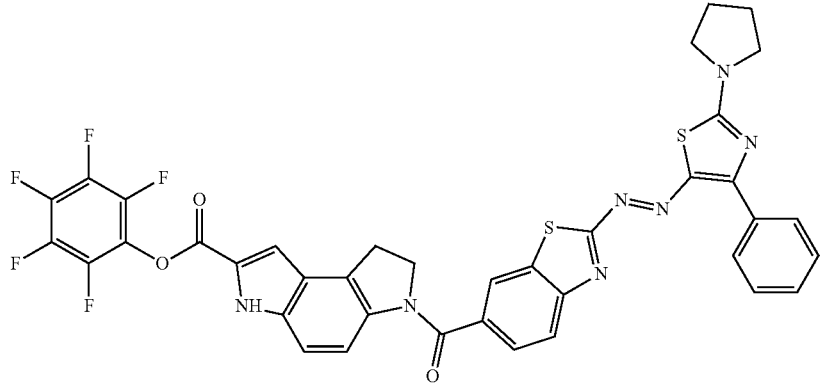 [SMILES: O=C(Oc1c(F)c(F)c(F)c(F)c1F)c1cc2c3c(ccc2[nH]1)N(C(=O)c1ccc2nc(/N=N/c4sc(N5CCCC5)nc4-c4ccccc4)sc2c1)CC3]

PFP-TFA was added in two, 0.05 mL portions over the period of 2 h to a solution of 78 (0.154 g, 0.25 mmol) and triethylamine (0.1 mL) in 5 mL of anhydrous DMF. The initial solution turned into a suspension by the end of this time. The suspension was cooled on ice, the insoluble material was cooled by filtration, washed with methanol and dried to afford 0.15 (76%) of PFP ester 79 as a black metallic solid. $^1$H NMR (DMSO-d6) δ 12.52 (s, 1H), 8.32 (m, 2H), 8.26 (s, 1H), 7.94 (d, J=8.1 Hz, 1H), 7.68 (d, J=8.1 Hz, 1H), 7.61 (m, 3H), 7.55 (s, 1H), 7.38 (br s, 1H), 4.22 (t, J=7.8 Hz, 2H), 3.93 (m, 2H), 3.62 (m, 2H), 3.25 (t obscured by water signal, J=8.1 Hz, 2H), 2.08 (m, 4H).

Post-Synthetic Conjugation of DSQ Groups by Reaction of the 6-amino-2-hydroxyhexyl-Modified Octadeoxythymidylate with PFP Esters 44, 77, 79 and Dabcyl To a solution of 3'-(6-amino-2-hydroxyhexyl)-octadeoxythymidylate (approx. 60 nmol), which had been prepared by oligonucleotide synthesis starting from the PS support ID #394 (Example 2) followed by C18 HPLC purification using triethylammonium bicarbonate buffer, in 20 μL of DMSO was added 0.7 mg (1.1 μmol) of PFP ester 44, 77 or 79 and 0.5 μL of triethylamine. After being kept at room temperature (55° C. in case of PFP ester 79) for 20 h the reaction was diluted with 1×HPLC buffer, centrifuged to spin down unreacted PFP ester and chromatographed on a C18 HPLC column eluting with a gradient of CH$_3$CN in 0.1 M triethylammonium bicarbonate buffer (pH ~9). The product peak was collected and dried in a SpeedVac vacuum concentrator under reduced pressure. Dabcyl conjugation using Quencher-470 PFP ester (ELITechGroup Inc., product #M830572) was performed analogously. The identities and purity of the products were confirmed by ESI mass-spectrometry.

Example 8. Absorption Spectra of Exemplary Octadeoxythymidylate Conjugates of the Disclosure Absorption spectra of various compounds in accordance with preferred embodiments of the present disclosure conjugated to octadeoxythymidylate, as shown in FIG. 11, were obtained using the instrumentation and measurement conditions described in Table 4 below.

TABLE 4

| Instrumentation and measurement conditions | |
|---|---|
| Instrument | PE Lambda 2S UV-VIS spectrophotometer |
| Conc. (mM) | 0.01-0.03 |
| Diluent | 50 mM Tris-HCl pH 8.5 |
| Temperature (° C.) | Ambient |

FIG. 11A-11C show UV-VIS absorption spectra of representative oligonucleotide conjugates in accordance with preferred embodiments.

Example 9. Oligonucleotide Synthesis

All oligonucleotides and oligonucleotide conjugates used in Examples 10-14 were synthesized using the instrumentation, synthesis and purification conditions described in Table 5 below.

TABLE 5

| Instrumentation and synthesis conditions | |
|---|---|
| Instrument | ABI 3900 DNA synthesizer |
| Scale | 200 nmol |
| Deblocking | 3% TCA |
| Amidite conc. | 100 mM (double coupling for all dye and quencher amidites) |
| Activator | 5-Ethylthiotetrazole |
| Oxidation | I$_2$/Pyridine/Water |
| Capping | Ac$_2$O/Pyridine/MeIm |
| Deprotection | conc. NH$_4$OH, 25% EtOH (70° C., 2 h) |
| Purification | 4.6 × 250 mm Luna C18 RP HPLC (2mL/min, gradient of CH$_3$CN, triethylammonium bicarbonate buffer, pH ~9) |
| Mass spectroscopy | Thermo Scientific, LCQ Fleet, ESI (TEA-HFIPA buffer) |

The mass spectrometry for the d(T$_8$)-3'-DSQ conjugates is listed in Table 6 below.

TABLE 6

Summary of ESI mass-spectroscopy of the d(T$_8$)-3'-DSQ conjugates

| Conjugate Name | DSQ ID # | MW Calc. (Da) | MW Observed (Da) | Purity (%) |
|---|---|---|---|---|
| T8-473 | 473 | 3225.5 | 3225.3 | 95.97 |
| T8-475 | 475 | 3311.5 | 3311.5 | 97.47 |
| T8-476 | 476 | 3329.6 | 3329.4 | 100 |
| T8-477 | 477 | 3243.5 | 3243.2 | 100 |
| T8-478 | 478 | 3299.6 | 3299.3 | 100 |
| T8-479 | 479 | 3306.9 | 3306.6 | 98.23 |
| T8-480 | 480 | 3271.6 | 3271.3 | 100 |
| T8-481 | 481 | 3350.6 | 3350.8 | 95.67 |
| T8-482 | 482 | 2977.2 | 2977.0 | 100 |
| T8-483 | 483 | 3275.5 | 3275.4 | 100 |
| T8-484 | 484 | 3074.3 | 3074.0 | 100 |
| T8-485 | 485 | 3257.5 | 3258.4 | 95.09 |
| T8-486 | 486 | 3295.57 | 3295.6 | 98.92 |
| T8-487 | 487 | 3092.35 | 3092.0 | 100 |
| T8-488 | 488 | 2908.16 | 2907.8 | 99.02 |
| T8-489 | 489 | 2890.12 | 2896.9 | 100 |
| T8-490 | 490 | 3150.41 | 3150.3 | 98.57 |
| T8-77 | 77 | 2984.25 | 2983.7 | 100 |
| T8-79 | 79 | 3168.45 | 3168.2 | 98.50 |
| T8-44 | 44 | 2927.18 | 2927.2 | 96.79 |
| T8-Dabcyl | Dabcyl | 2818.03 | 2817.9 | 100 |

Example 10. Thermal Denaturation of DSQ-Labeled TaqMan Probes

To evaluate duplex-stabilizing and fluorescence quenching properties of new DSQ derivatives, two TaqMan probes labeled with FAM or AP525 were investigated. The probes (200 nM) FAM-5'-G*CAGGTTCCGGTTTTG-DSQ (SEQ ID NO:1) or AP525-5'-G*ACCACGTACCGCATTG-DSQ (SEQ ID NO:2) probes were hybridized in a PCR buffer with 1 µM of the respective complement (FAM complement: 5'-TCAAAACCGGAACCTGCT (SEQ ID NO:3); AP525 complement: TCAATGCGGTACGTGGTCT (SEQ ID NO:4) by briefly heating the solution to 80° C., cooling to 20° C., then ramping to 90° C. while monitoring fluorescence. Background fluorescence was measured at 90° C., temperature at which all duplexes have been completely denatured. Instrumentation and measurement conditions were as shown in Table 7 below. Results are summarized in FIGS. 12 and 13.

TABLE 7

Instrumentation and experimental conditions

Instrumentation and measurement conditions

| Instrument | Varian Cary Eclipse Fluorimeter |
|---|---|
| Data mode | Fluorescence |
| Scan mode | Emission |
| X Mode | Wavelength (nm) |
| Ex. Wavelength (nm) | 496 (FAM), 527 (AP525) |
| Em. Wavelength (nm) | 517 (FAM), 549 (AP525) |
| Ex. Slit (nm) | 5 |
| Em. Slit (nm) | 5 |
| Measurement temperature (° C.) | 20.0–90.0, 1° C./min ramp |
| 1X PCR buffer | 40 mM NaCl, 10 mM Tris, 5 mM MgCl$_2$, pH 8.9 |

Figure 12:
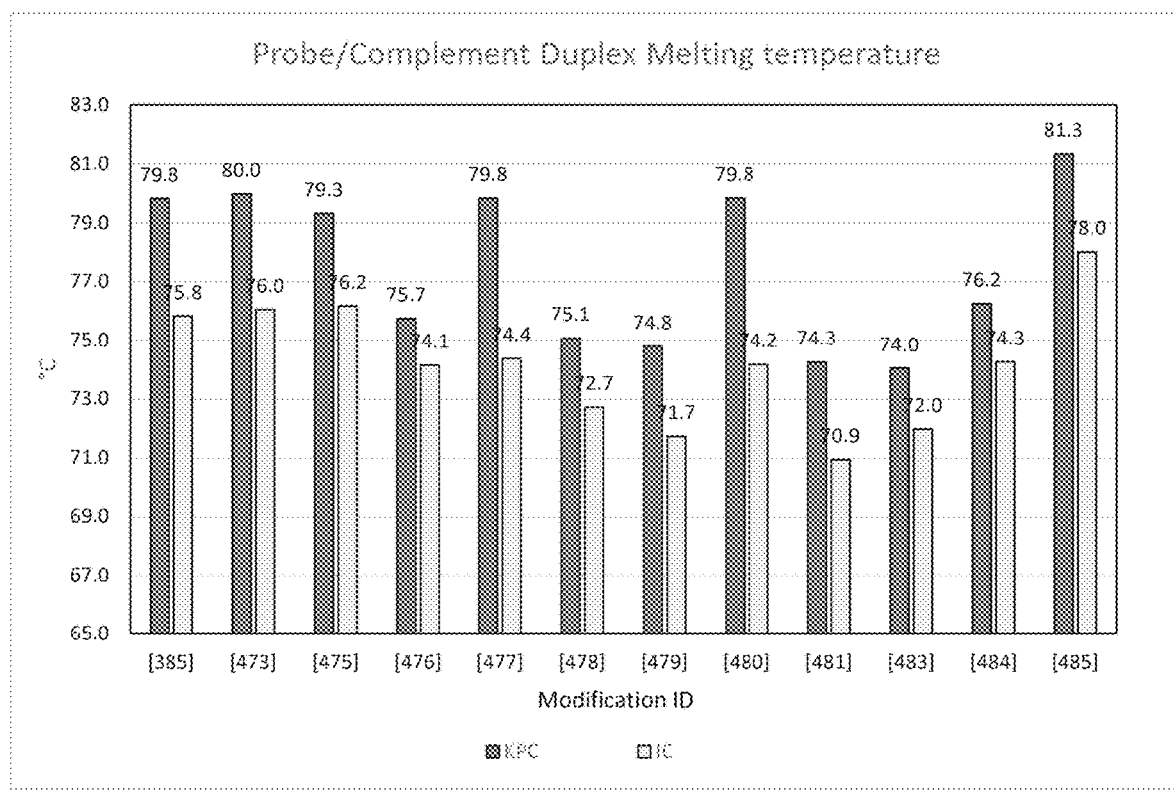
FIG. 12 shows melting temperatures of (KPC+KPC–C) and (IC+IC–C) duplexes and corresponding sequences.
Figure 18:
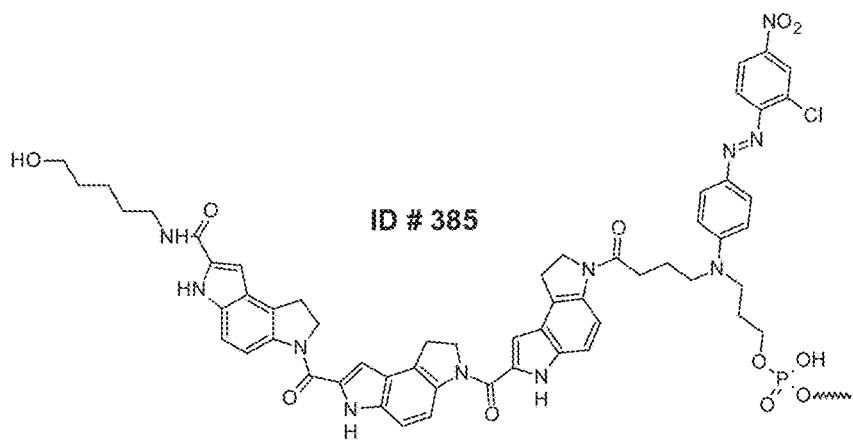
FIG. 18 shows the structures of MGB-Quencher (ID #385), $CDPI_3$ (ID #391), AP525, AP593 and AP639 dyes, with a wavy bond indicating the attachment point to an oligonucleotide.
Figure 18:
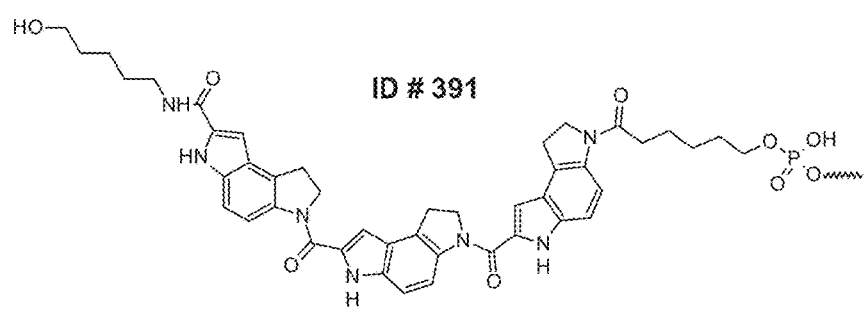
Figure 18:
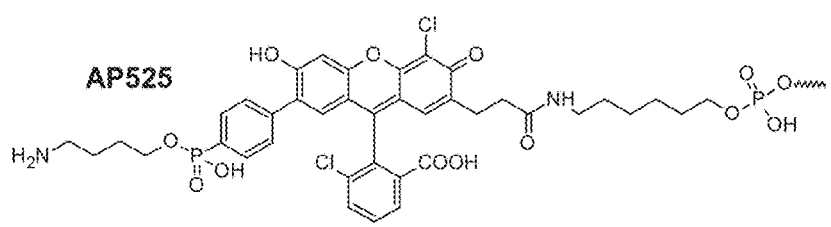
Figure 18:
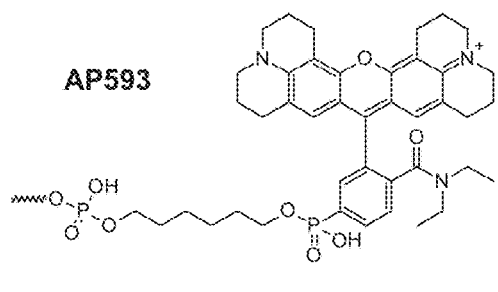
Figure 18:
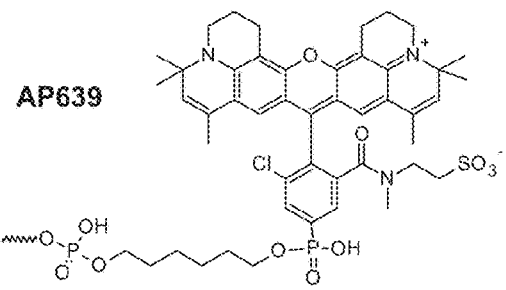

FIG. 12 shows a melting temperature comparison for duplexes formed between two DNA probes and their respective complementary targets. The probes are labeled with various exemplary DSQ derivatives at the 3' end and one of the fluorophores, FAM or AP 525, at the 5' end. For reference purposes, probes (ID #385), which have the traditional structure of both the MGB and the quencher (CDPl$_3$+Eclipse quencher, FIG. 18), are also included in the comparison. It is clear that probes with certain DSQ derivatives (e.g. modification ID #473, 477, 480, 485) have melting temperatures that are equal or exceed the values of the reference probes. This confirms that the truncated MGB (CDPl$_2$ in this case) can regain its full duplex-stabilizing ability when extended with certain types of diaryl-azo derivatives of Formula I. Notably, the probes labeled with DSQ ID #485 outperform the reference probes (ID #385) indicating that, at least in this particular sequence context, the diaryl-azo groups bring more to duplex stability than the displaced CDPl unit. The least efficient duplex-stabilizing DSQ derivatives (ID #479, 481, 483) contained either a 1,4-substituted phenyl or an 2,4-substituted-N-methylpyrrol ring as the Ar$^1$ group of formula III. The latter result is unexpected in view of the report by Ong et al. (2012) on the properties 4-(1-methylpyrrol-2-yl)azo-1-methylpyrrole-2-carboxylates.

Figure 13:
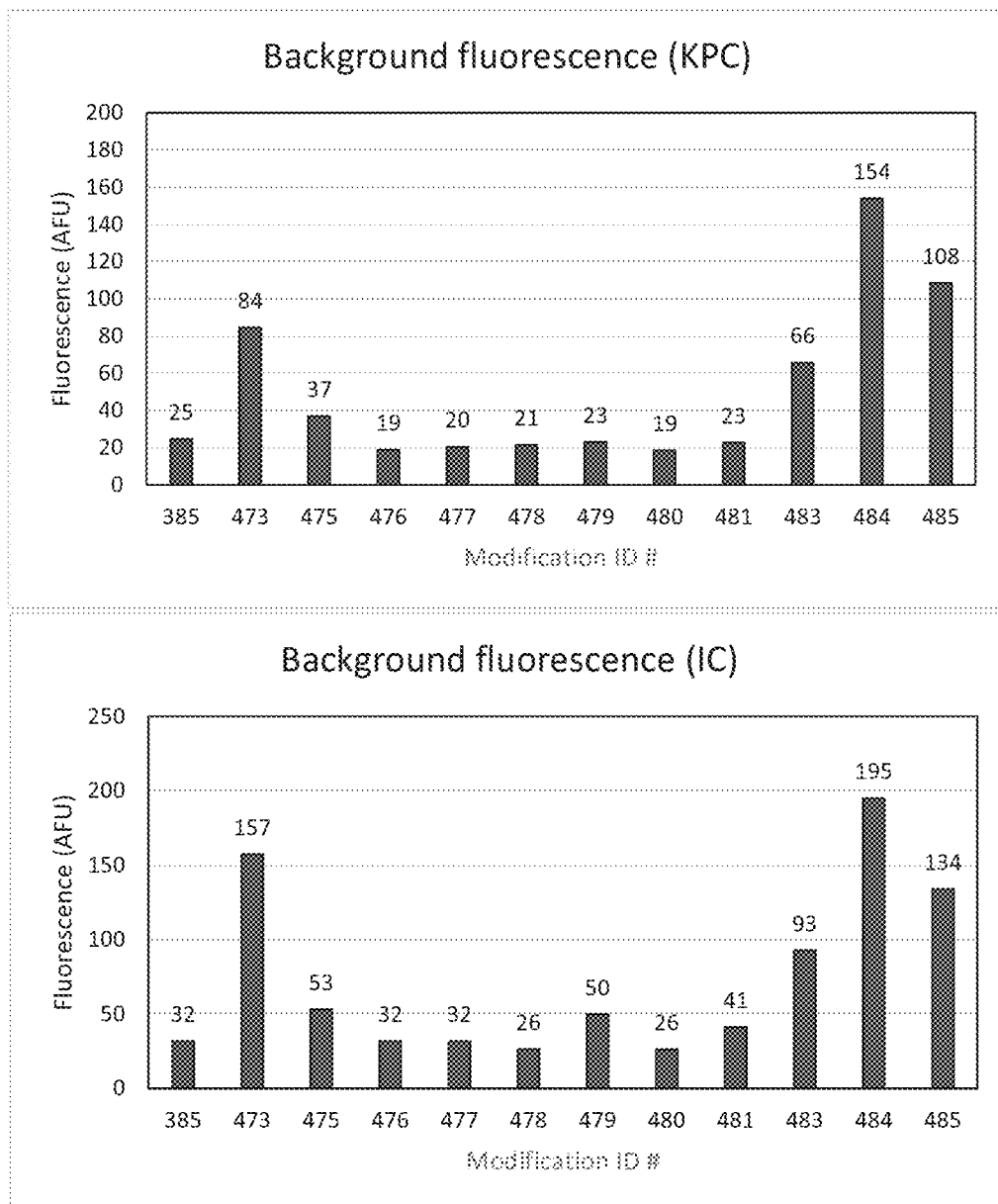
FIG. 13 shows background fluorescence (90° C.) of KPC and IC oligonucleotide probes labeled with representative 3'-DSQ derivatives, where the probes were also labeled with 5'-FAM (KPC) or 5'-AP525 (IC).

FIG. 13 addresses the fluorescence quenching properties of preferred embodiments of the DSQ derivatives. In this test, background fluorescence of unhybridized probes is the measure of quenching efficiency. As expected, the derivatives with the best spectral overlap between fluorophore's emission (FAM emission maximum—515 nm, AP525 emission maximum—549 nm) and quencher's absorption (FIG. 11) demonstrate the lowest background fluorescence thus confirming that the main quenching occurs via the FRET mechanism (Didenko (2001)). Some DSQ analogs (e.g. SDQ ID #476, 477, 478 and 480) have the background fluorescence as low or lower as the reference Eclipse quencher (part of modification ID #385). These results confirm that the general quenching properties of aryl-azo compounds are not affected by the incorporation into the DSQ structure according to the statements of this specification.

Example 11. Fluorescence Melting Analysis of d(T$_8$)-DSQ/FAM-d(A$_8$CC) Duplexes To evaluate duplex stabilizing effect of representative DSQ derivatives in an ALT-rich sequence context, a short d(T$_8$)/d(A$_8$CC) duplex was investigated by fluorescence melting analysis. 3'-DSQ-TTTTTTTT (d(T$_8$)-DSQ) conjugates were combined with complement (5'-FAM-AAAAAAAACC (SEQ ID NO:5)) in the buffer specified in Table 8 and the solution equilibrated to 10° C., and dissociation curves acquired by monitoring fluorescence from 10-70° C. at a ramp of 1°/min. Duplex denaturation was monitored by detecting fluorescence change over a thermal ramp. Melting temperature (Tm) was calculated by finding second derivative maximum of the raw melt curve. Instrumentation and measurement conditions were as shown in Table 8 below. Results are summarized in Table 9 and FIG. 14.

TABLE 8

Instrumentation and experimental conditions

Instrumentation and measurement conditions

| Instrument | Varian Cary Eclipse Fluorimeter |
|---|---|
| Data mode | Fluorescence |
| Ex. Wavelength (nm) | 496 (FAM), 527 (AP525) |
| Em. Wavelength (nm) | 517 (FAM), 549 (AP525) |

TABLE 8-continued

Instrumentation and experimental conditions

Instrumentation and measurement conditions

| | |
|---|---|
| Ex. Slit (nm) | 5 |
| Em. Slit (nm) | 5 |
| Measurement temperature (° C.) | 10-70° C., 1° C./min |
| Buffer | 100 mM NaCl, 10 mM MgCl$_2$, 10 mM Na$_2$-PIPES, pH 7.0 |
| T8 conjugate Concentration | 0.2 μM |
| Complement Concentration | 0.1 μM |

TABLE 9

Tm data

General DSQ Structure: (CDPI)$_n$—(O=)C—Ar$^1$—N=N—Ar$^2$

| Name | DSQ ID # | Tm (° C.) | ΔTm relative to T8-Dabcyl | n | —(O=)C—Ar$^1$— | —Ar$^2$ |
|---|---|---|---|---|---|---|
| T8-473 | 473 | 45.6 | 30.0 | 2 | Indolyl | (Dimethylamino) phenyl |
| T8-475 | 475 | 44.3 | 28.7 | 2 | Indolyl | (Pyrrolidino,dimethoxy) phenyl |
| T8-476 | 476 | 21.9 | 6.3 | 2 | Benzothiazolyl | (Pyrrolidino,dimethoxy) phenyl |
| T8-477 | 477 | 45.5 | 29.9 | 2 | Benzothiazolyl | (Dimethylamino) phenyl |
| T8-478 | 478 | 44.2 | 28.6 | 2 | Benzothiazolyl | (Dimethylamino) phenyl |
| T8-479 | 479 | 34.7 | 19.1 | 2 | Phenyl | (Pyrrolidino,dimethoxy) phenyl |
| T8-480 | 480 | 45.3 | 29.7 | 2 | Benzothiazolyl | (Dimethylamino) phenyl |
| T8-481 | 481 | 26.7 | 11.1 | 2 | Phenyl | (Dimethylamino) phenyl-azo-phenyl |
| T8-482 | 482 | 26.7 | 11.1 | 2 | N/A | N/A |
| T8-483 | 483 | 35.6 | 20.0 | 2 | pyrrolyl | (Pyrrolidino,dimethoxy) phenyl |
| T8-484 | 484 | 28.8 | 13.2 | 1 | Indolyl | Pyrrolidinothiazolyl |
| T8-485 | 485 | 44.8 | 29.2 | 2 | Indolyl | Pyrrolidinothiazolyl |
| T8-486 | 486 | 47.6 | 32.0 | 2 | Benzothiazolyl | Julolidinyl |
| T8-487 | 487 | 16.6 | 1.0 | 1 | Benzothiazolyl | Pyrrolidinothiazolyl |
| T8-488 | 488 | 19.3 | 3.7 | 0 | Benzothiazolyl | Pyrrolidinothiazolyl |
| T8-489 | 489 | 18.4 | 2.8 | 0 | Indolyl | Pyrrolidinothiazolyl |
| T8-490 | 490 | 23.2 | 7.6 | 1 | Indolyl | (Pyrrolidino) phenylthiazolyl |
| T8-77 | 77 | 23.9 | 8.3 | 0 | Benzothiazolyl | (Pyrrolidino) phenylthiazolyl |
| T8-79 | 79 | 20.7 | 5.1 | 1 | Benzothiazolyl | (Pyrrolidino) phenylthiazolyl |
| T8-44 | 44 | 16.5 | 0.9 | 0 | Benzothiazolyl | Julolidinyl |
| T8-dabcyl | Dabcyl | 15.6 | 0.0 | 0 | Phenyl | (Dimethylamino) phenyl |

FIG. 14A shows the effects of various DSQ ligands on the d(T$_8$)/d(A$_8$) duplex stability and FIG. 14B shows the effects of various DSQ ligands on the d(T$_8$)/d(A$_8$) duplex melting temperature, another demonstration of duplex-stabilizing properties of new DSQ derivatives. In this example, a short d(T$_8$)/d(A$_8$CC) duplex is used to enhance the differences between the derivatives. As a control, a CDPI$_2$-labeled d(T$_8$) oligonucleotide is also included. The d(A$_8$CC) complement is labeled with a fluorescein group at the 5'-end, which is quenched in the duplex form and unquenched upon duplex denaturation allowing for fluorescence-based melting detection. It can be seen that the DSQ analogs, composed of certain aryl-azo moieties and two CDPl units (e.g. DSQ ID #473, 475, 477, 478, 479, 480, 483, 485 and 486), outperform the control CDPI$_2$-conjugate thus confirming that the aryl-azo moiety effectively contributes to the duplex stabilization according to the statements of this specification. In one example, the DSQ ID #484 conjugate, which has a diaryl-azo moiety coupled to a single CDPl unit, outperforms the control CDPl$_2$-conjugates showing that this particular structure has especially high affinity for DNA duplex.

Example 12. Evaluation of Sequence Effect on Duplex Stabilization by DSQ ID #477

To establish the stabilizing contribution of the DSQ (ID #477) moiety to the duplex, sequences (Table 11) with varying G/C content in the inferred binding region of the DSQ moiety were evaluated. For comparison, CDPl$_2$ (ID #482), CDPl$_3$ (ID #391), MGB-Quencher (ID #385)-labeled and unmodified oligonucleotides were also tested. Duplexes were heated briefly to 80° C., equilibrated at 20° C., and then ramped to 70 or 90° C. while monitoring UV absorbance. Instrumentation and measurement conditions were as shown in Table 10 below. Results are summarized in Table 11 and FIG. 15.

TABLE 10

Instrumentation and experimental conditions

Instrumentation and measurement conditions

| | |
|---|---|
| Instrument | Cary Bio 400 |
| Wavelength monitor | 260 nm |
| Measurement temperature (° C.) | 20-70 or 20.0-90.0, 1° C./min ramp |
| Buffer 1 | 20 mM Na$_2$-PIPES, pH 8 |
| Buffer 2 | 10 mM Na$_2$-PIPES, 100 mM NaCl, 10 mM MgCl$_2$, pH 7 |
| Test Oligo Concentration | 3 μM |
| Complement Concentration | 6 μM |

TABLE 11

| SEQ. ID NO: | Sequence (5'-3') | Tm (° C.) 5'-none [482] | 5'-[391] | 5'-[385] | 5'-[477] |
|---|---|---|---|---|---|
| 6 | ACACAAGC-TACA | 56.85 60.38 | 73.05 | 65.56 | 71.00 |
| 7 | TTATATGC-CACG | 53.50 61.37 | 73.89 | 68.87 | 63.61 |

TABLE 11-continued

| SEQ. ID NO: | Sequence (5'-3') | Tm (° C.) 5'- none [482] | 5'-[391] | 5'-[385] | 5'-[477] |
|---|---|---|---|---|---|
| 8 | TACACTGGA-CAT | 55.75 61.44 | 66.18 | 60.40 | 66.80 |
| 9 | CAGAGCTTA-CAT | 53.75 58.77 | 70.51 | 64.68 | 53.78 |
| 10 | GCTCTGT-TAAGT | 50.27 52.19 | 57.69 | 56.53 | 54.20 |
| 11 | GAAAACACCGTC | 56.96 62.75 | 73.99 | 69.36 | 69.91 |
| 12 | TCCTGAGT-CAAC | 55.29 60.56 | 61.66 | 61.15 | 53.42 |
| 13 | CGCTAAATCCTG | 55.91 61.83 | 75.16 | 67.17 | 71.78 |
| 14 | TGTTC-TACCGAG | 54.95 62.52 | 73.78 | 68.68 | 68.94 |
| 15 | CGAAATACCCTG | 53.93 63.58 | 76.78 | 70.64 | 72.02 |

Figure 15:
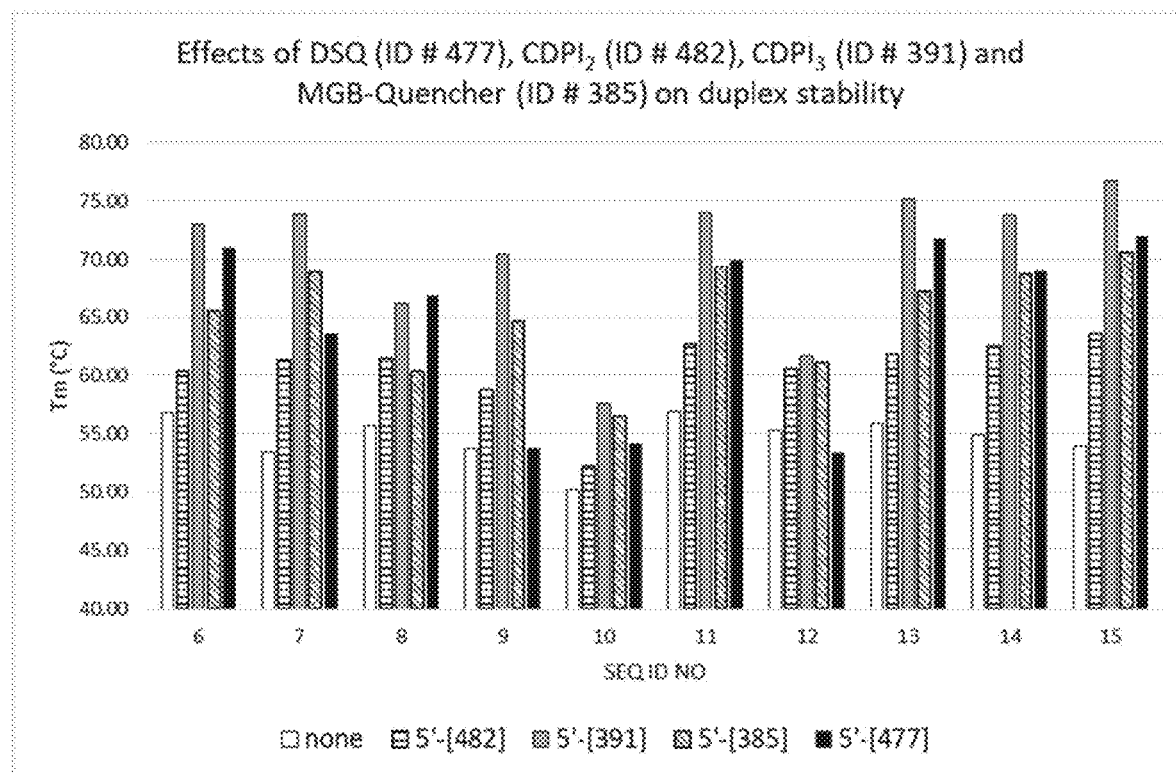
FIG. 15 shows a comparison of duplex-stabilizing effects of $CDPI_2$, $CDPI_3$ (ID #391), MGB-Quencher (ID #385) and DSQ (ID #477) in different sequence context, and corresponding sequences.

In order to demonstrate that new DSQ moieties can stabilize DNA duplexes with different sequence context, the test shown in FIG. 15 and Table 10 was performed. A set of DSQ (ID #477)-oligonucleotide conjugates with different G/C content in the putative DSQ-binding region was prepared. For comparison, CDPl$_2$ (ID #482), CDPl$_3$ (ID #391), MGB-Quencher (ID #385)-labeled and unmodified oligonucleotides were also tested. In all but two cases, the DSQ ligand outperformed the control CDPl$_2$ moiety by up to 10° C. thus confirming the earlier results with the T8 conjugates (Example 11). The two sequences (SEQ ID NO:9 and SEQ ID NO:12) with lower than the control CDPl$_2$ melting temperatures had a significant internal secondary structure, over-stabilized by the presence of the DSQ moiety, as shown in FIG. 15 This type of MGB-stabilized secondary structure is expected and should be avoided by thorough sequence analysis. Aside the two outliers, the obtained results confirm that the new DSQ derivatives are suitable for DNA duplex stabilization of various sequences and G/C content.

Example 13. Real-Time PCR Using DSQ-Labeled TaqMan Probes

To evaluate PCR performance of new DSQ derivatives, PCR was conducted using two DSQ-labeled TaqMan probes (TaqMan assay). PCR Monoreagent formulation and PCR conditions are shown in Table 12. Result are summarized in Table 13 and FIG. 16.

TABLE 12

| PCR formulation and PCR conditions | |
|---|---|
| Instrument | ELITe InGenius |
| KPC primers | AATAAATCATAAGCAGACTGGGCAGTCGG (SEQ ID NO: 18) AATAAATCATGTCATTTGCCGTGCCATAC (SEQ ID NO: 19) |
| IC2 primers | CTCATTTTTCTACCGGAGATCTTGT (SEQ ID NO: 20) CTGCACGGACCAGTTACTTTACG (SEQ ID NO: 21) |
| KPC probe | FAM-G*CAGGTTCCGGTTTTG-MGBQ (SEQ ID NO: 22) |
| IC2 probe | AP525-G*ACCACGTACCGCATTG-MGBQ (SEQ ID NO: 23) |
| Primer concentration (nM) | 500 nM |
| Probe concentration (nM) | 100 nM |
| Magnesium concentration (mM) | 3 |
| Enzyme concentration | 3 U/reaction |
| Thermocycling | Precycle: 95° C., 240 sec 40 cycles of PCR: Denature: 95° C., 10 sec Anneal: 56° C., 30 sec Extend: 73° C., 15 sec |
| KPC target concentration | 1000 copies/PCR reaction |
| IC2 target concentration | 1000 copies/PCR reaction |

TABLE 13

Summary of PCR data

| DSQ ID # | Ct KPC* (Fluorophore) | IC * (AP525) | Signal at cycle #45 KPC* | IC* | Background KPC* | IC * | Signal/Background KPC * | IC * |
|---|---|---|---|---|---|---|---|---|
| 385 | 28.6 (FAM) | 30.3 | 6306 | 4551 | 1237 | 543 | 5.1 | 8.4 |
| 473 | 28.4 (FAM) | 29.7 | 7469 | 9960 | 2329 | 3829 | 3.2 | 2.6 |
| 475 | 28.5 (FAM) | 29.8 | 6914 | 7653 | 1564 | 1719 | 4.4 | 4.5 |
| 476 | 29.2 (FAM) | 30.1 | 5525 | 5650 | 1038 | 479 | 5.3 | 11.8 |
| 477 | 28.7 (FAM) | 30.4 | 5772 | 6289 | 909 | 438 | 6.4 | 14.4 |
| 477 | 29.7(AP593) | 27.9 | 3335 | 6994 | 329 | 724 | 10.1 | 9.7 |
| 477 | 28.3(AP639) | 27.7 | 18984 | 7360 | 1665 | 828 | 11.4 | 8.9 |
| 478 | 29.2 (FAM) | 30.8 | 6125 | 5169 | 1030 | 447 | 5.9 | 11.6 |
| 479 | 29.3 (FAM) | 30.8 | 5145 | 5252 | 1014 | 857 | 5.1 | 6.1 |
| 480 | 28.9 (FAM) | 30.8 | 5428 | 5119 | 832 | 374 | 6.5 | 13.7 |
| 481 | 29.8 (FAM) | 31.4 | 4526 | 4969 | 993 | 773 | 4.6 | 6.4 |

* All values are averages of three or more replicates

FIG. 16 shows PCR performance of representative conjugates of the disclosure. Two TaqMan probes, one (KPC) labeled with FAM and the other one (IC2) with AP525 at the 5'-end (FIG. 12), were synthesized using the DNA synthesis supports described in this specification. As a control, the same two probes were also synthesized using the traditional MGB-Quencher reagent (modification ID #385). Target DNAs amplification was performed in the presence of the probes, target-specific primers and Taq polymerase. To evaluate the performance, threshold cycle (Ct), baseline fluorescence (background), fluorescence signal (fluorescence at cycle 45) and signal-to-background ratio were compared as summarized in Table 12 and FIG. 16. Based on the Ct values, the new probes provided similar amplification efficiency and overall test sensitivity as the control probe with Ct values generally varying within one amplification cycle. Background fluorescence, with the exception of the DSQ ID 473 and 475 were same as or lower than the background of the control probe. As a consequence of the low background, some of the new DSQ probes demonstrated improved Signal-to-Background ratios (e.g DSQ ID #476, 477, 478 and 480). These results demonstrate that the new DSQ derivatives are suitable for PCR applications with their performance comparable or better than the traditional technology.

Simultaneous amplification and detection of multiple targets is an essential requirement for multiplex PCR applications. This can only be enabled if multiple fluorophores with wide range of emission spectra are combined in one PCR reaction. In order to demonstrate that new DSQ derivatives are also suitable for PCR applications with red-shifted fluorophores an experiment was performed in which, the KPC probe was labeled either with AP593 (emission maximum 613 nm) or AP639 (emission maximum 655 nm) dye at the 5'-end and the DSQ ID #477 at the 3'-end. The obtained results (summarized in Table 12) confirmed that the KPC target was successfully amplified and efficiently detected with Ct values, background fluorescence and signal-to-background ratios similar or better to those of the FAM-labeled probe.

Example 14. Evaluation of Hybridization-Triggered Fluorescence of DSQ-Labeled Probes To evaluate fluorogenic properties of oligonucleotides of Formula VII, the duplex fluorescence at 50° C. (Signal), single strand fluorescence at 50° C. (Background) and Signal-to-background ratio (S/B) of two oligonucleotides labeled at the 5'-end with DSQ ID #473 and either FAM-HEG (ELITechGroup Inc., product #M830100) or AP525-HEG (ELITechGroup Inc., product #M100104) were synthesized and tested. To generate a fluorescent signal the DSQ-FAM (or AP525)-5'-TAAAAGGTGTAC (SEQ ID NO:24) (200 nM) were hybridized in a PCR buffer with 1 µM of the complement (TTGTACACCTTTTATT (SEQ ID NO:25)) by briefly heating the solution to 80° C., cooling to 20° C., then ramping to 90° C. while monitoring fluorescence. Background was measured in the absence of complement. Instrumentation and measurement conditions were as shown in Table 14 below. Results are summarized in Table 15 and FIG. 17A-17B.

TABLE 14

Instrumentation and measurement conditions

| | |
|---|---|
| Instrument | Varian Cary Eclipse Fluorimeter |
| Data mode | Fluorescence |
| Scan mode | Emission |
| X Mode | Wavelength (nm) |
| Ex. Wavelength (nm) | 496 (FAM), 527 (AP525) |
| Em. Wavelength (nm) | 517 (FAM), 549 (AP525) |
| Ex. Slit (nm) | 5 |
| Em. Slit (nm) | 5 |
| Measurement temperature (° C.) | 20.0-90.0, 1° C./min ramp |
| 1X PCR buffer | 40 mM NaCl, 10 mM Tris, 5 mM MgCl$_2$, pH 8.9 |

TABLE 15

| | Background | Signal | S/B |
|---|---|---|---|
| FAM | 21.5 | 128.7 | 6.0 |
| AP525 | 45.4 | 629.5 | 13.9 |

Figure 17A:
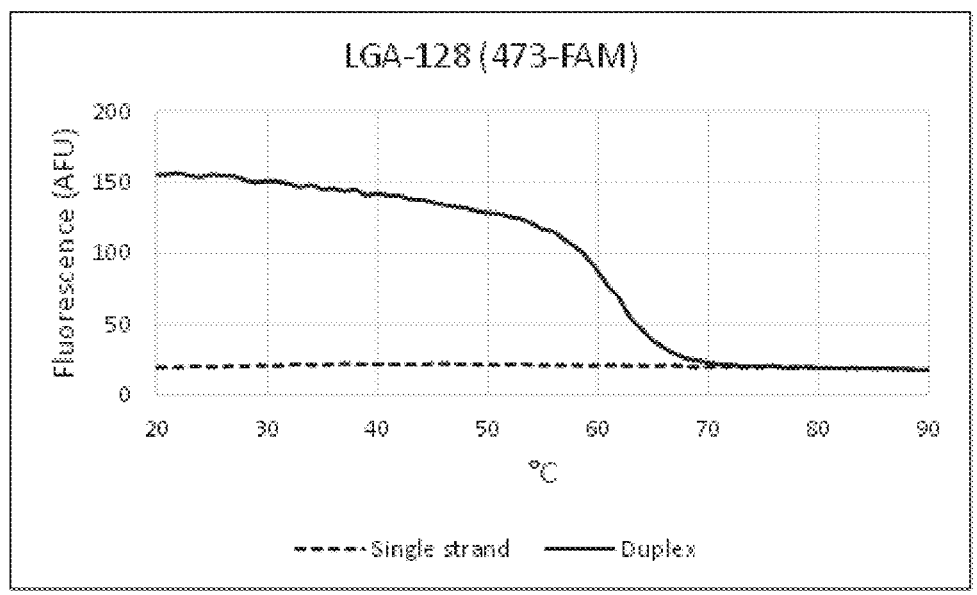
FIG. 17A shows duplex and single strand fluorescence temperature profile of an oligonucleotide conjugate labeled with 5'-DSQ ID #473 and 5'-FAM.
Figure 17B:
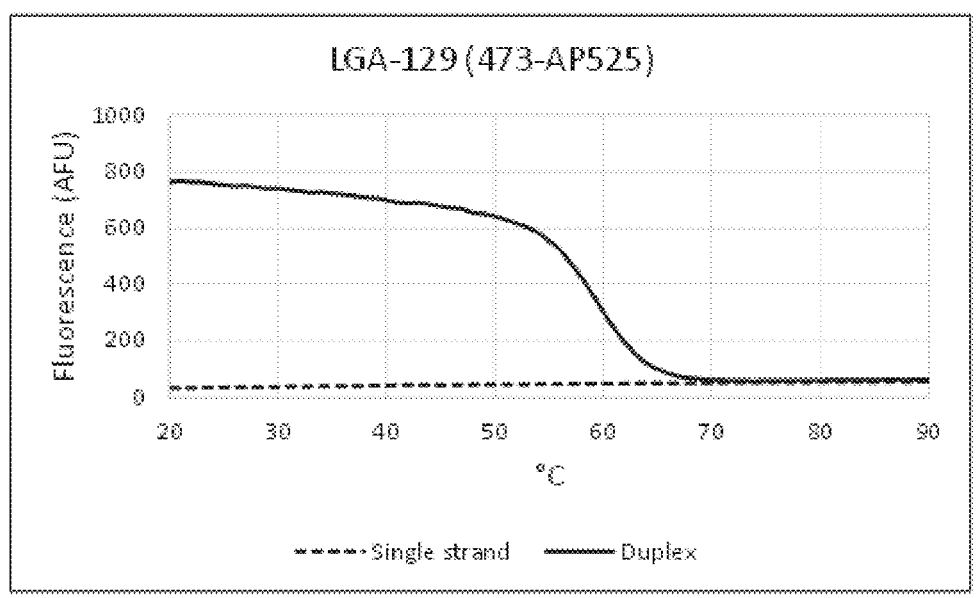
FIG. 17B shows duplex and single strand fluorescence temperature profile of an oligonucleotide conjugate labeled with 5'-DSQ ID #473 and 5'-AP525.

The new DSQ derivatives can also be used for the preparation of hybridization probes and primers, which rely on spatial separation between the quenching and fluorescent moieties upon hybridization to target to generate fluorescent signal. In one particular configuration, the DSQ and fluorophore moieties are positioned at the same end of an oligonucleotide. In such configuration, spatial separation between the quencher and fluorophore is achieved via the DSQ binding within the duplex minor groove. Such conjugates can be synthesized starting from a DSQ synthesis support followed by a fluorophore phosphoramidite that is suitable for internal incorporation (for example FAM-HEG and AP525-HEG phosphoramidites available from ELITechGroup Inc.), and then an oligonucleotide sequence. FIGS. 17A and 17B show results of a thermal melting experiment involving such fluorogenic oligonucleotide labeled with the DSQ ID #473 in combination with either FAM or AP525 fluorophore. Due to its blue-shifted absorption spectrum (FIG. 11), this DSQ mostly relies on the contact quenching ((U.S. Pat. No. 6,150,097) in its single stranded state. The quenching is eliminated upon DSQ's confinement in the minor groove. As a result such oligonucleotides demonstrate good fluorescence signal and signal-to-background ratios (Table 14) and are useful as fluorogenic primers or probes depending on whether the 3'-hydroxyl is present or blocked.

REFERENCES CITED

The following documents and publications are hereby incorporated by reference.

U.S. and Foreign Patent Documents

References Cited

The following documents and publications are hereby incorporated by reference.
U.S. and Foreign Patent Documents
EP Patent No. 1384789
US Patent Appl. Nos.
20140335515
20130030166F
U.S. Pat. Nos.
RE 38,416
3,996,345

5,419,966
5,512,667
5,585,481
5,696,251
5,736,626
5,801,155
5,942,610
6,150,097
6,312,894
6,323,337
6,399,392
6,492,346
6,699,661
6,699,975
6,727,356
6,790,945
6,821,727
6,972,339
7,019,129
7,166,715
7,205,105
7,262,007
7,381,818
7,439,341
7,564,567
7,582,739
7,767,834
7,759,470
7,803,536
7,879,986
7,790,385
8,163,910
8,586,759
8,637,658
9,056,887

Non-Patent References

Ausubel, et al., CURRENT PROTOCOLS IN MOLECULAR BIOLOGY, John Wiley & Sons (1987, 1988, 1989, 1990, 1991, 1992, 1993, 1994, 1995, 1996)
Berge, S. M., et al., Journal of Pharmaceutical Science, 66: 1-19 (1977).
Boga, C. et al., Org. Biomol. Chem. 14: 7061-7068 (2016)
Bonnet et al., Proc. Natl. Acd. Sci. USA, 96: 6171-6176 (1999)
Crisalli and Kool, Bioconjug Chem., 22: 2345-54 (2011)
Demidov and Frank-Kamenetskii TRENDS in Biochemical Sciences, 29: 62-71 (2004)
Eckstein (ed.), OLIGONUCLEOTIDES AND ANALOGUES: A PRACTICAL APPROACH, IRL Press (1991).
Edmonds et al. in Modern Carbonyl Olefination. Ed. T. Takeda, Wiley-VCH Verlag GmbH & Co. KGaA, Weinheim 2004
Gait (ed.), OLIGONUCLEOTIDE SYNTHESIS: A PRACTICAL APPROACH, IRL Press (1984)
T. W. Greene and P. G. Wuts, Greene's Protective Groups in Organic Chemistry, Wiley, 4nd ed. 2007
Harrison and Harrison et al., Compendium of Synthetic Organic Methods, Vols. 1-8, John Wiley and Sons. 1971-1996
Heid et al., Genome Res. 6: 986-994 (2009)
Hermanson, Bioconjugate Techniques, Elsevier, 1996, pages 139-140 and 274-275, Hymas W C, Hillyard D R J Virol Methods. 156:124-8 (2009)
Johansson et al. J. Am. Chem. Soc., 124: 6950-6956 (2002)
Knemeyer and Marme, DNA & Gene Sequences. 1, No. 2: 145-157 (2007)
Kutyavin et al. Nucl. Acids Res. 28: 655-661(2000)
Lakowicz, Principles of Fluorescence Spectroscopy, Third Edition, Springer 2007, pages 368-394
Lukhtanov et al. Bioconjugate Chemistry, 6: 418-426 (1995)
Lukhtanov et al., Bioconjug Chemistry, 7:564-567 (1996)
Lukhtanov et al., Nucl. Acids Res., 35: e30 (2007)
Mahajan, S. et al. Analytical Biochemistry, 351(2), 273-281 (2006)
Malicka, J. M. et al. Chemistry—A European Journal, 19: 12991-13001 (2013)
March J. in Advanced Organic Chemistry, Chapter 4", 4th edition John Wiley and Sons, New York, 1992 pages 71-124
Maniatis, Fritsch & Sambrook, MOLECULAR CLONING: A LABORATORY MANUAL, Cold Spring Harbor Laboratory Press (1982)
Matayoshi et al., Science., 247:954-958 (1990)
Morrison et al. Anal. Biochem., 183: 231-244 (1998)
Ong et al. Org. Biomol. Chem., 10: 1040-1046 (2012)
Paris et al. Nucleic Acids Res., 38(7): e95 (2010)
Reddy, et al. (1999), Pharmacol. Therap., 84:1-111 (1999).
Sambrook, Fritsch & Maniatis, MOLECULAR CLONING: A LABORATORY MANUAL, Second Edition, Cold Spring Harbor Laboratory Press (1989)
Sedlak and Jerome, Diagn Microbiol Infect Dis. 75(1):1-4 (2013).
Smith, March. Advanced Organic Chemistry 6th ed. 2007 by John Wiley & Sons, Inc. (pages 501-502)
Tolstrup et al. Nucl. Acids. Res., 31:3758-3762 (2003)
Tyagi et al. Nat Biotechnol., 14; 303-8 (1996)
Tyagi et al. Nat Biotechnol., 16: 49-53 (1998)
Walker et al., Biopolymers, 44: 323-334 (1997)
Wemmer, D. E., and Dervan P. B., Current Opinon in Structural Biology, 7:355-361 (1997)
Zimmer, C & Wahnert, U., Prog. Biophys. Molec. Bio. 47: 31-112 (1986)

What is claimed is:

1. An oligonucleotide conjugate comprising a fluorescence quenching compound and having the formula:

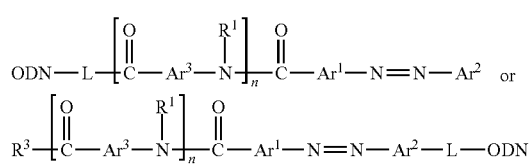

wherein ODN is an oligonucleotide;
L is a linking group;
$R^1$ is H, alkyl, or alkyl covalently connected to $Ar^3$
$Ar^1$ and $Ar^2$ are aromatic or hetero-aromatic moieties;
$Ar^3$ is an aromatic moiety selected from substituted or unsubstituted indole, benzofuran, benzothiophene and benzoselenophene;
$R^3$ is hydroxyl, a linking group, or a blocking group; and
n is from 1 to 5.

2. The oligonucleotide conjugate of claim 1, wherein the oligonucleotide comprises a fluorophore connected to the oligonucleotide.

3. The oligonucleotide conjugate of claim 2, wherein the fluorophore is FAM, AP525, AP559, AP593 or AP662.

4. The oligonucleotide conjugate of claim 1, wherein the oligonucleotide comprises a minor groove binder connected to the oligonucleotide.

5. The oligonucleotide conjugate of claim 1, wherein the oligonucleotide comprises one or more modified nucleobases or modified bases.

6. The oligonucleotide conjugate of claim 1, wherein L is connected to the oligonucleotide at a 3'-end.

7. The oligonucleotide conjugate of claim 1, wherein L is connected to the oligonucleotide at a 5'-end.

8. The oligonucleotide conjugate of claim 1, wherein L is connected to the oligonucleotide at a position other than a 3'- or 5'-end.

9. The oligonucleotide conjugate of claim 1 having the formula:

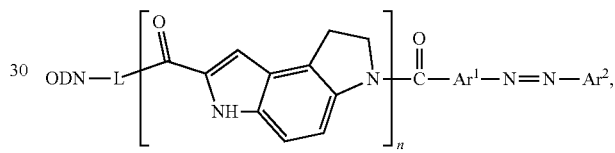

wherein n is 1, 2, or 3.

10. The oligonucleotide conjugate of claim 1 having the formula:

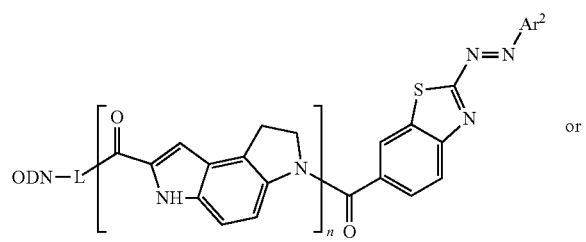

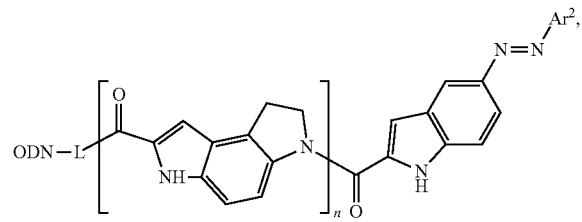

wherein n is 1, 2, or 3.

* * * * *